(12) United States Patent
Devani

(10) Patent No.: US 12,274,500 B2
(45) Date of Patent: Apr. 15, 2025

(54) METHOD AND SYSTEM FOR MEASURING PUPILLARY LIGHT REFLEX WITH A MOBILE PHONE

(71) Applicant: BioTrillion, Inc., San Francisco, CA (US)

(72) Inventor: Savan R. Devani, San Francisco, CA (US)

(73) Assignee: BioTrillion, Inc., San Francisco, CA (US)

( * ) Notice: Subject to any disclaimer, the term of this patent is extended or adjusted under 35 U.S.C. 154(b) by 672 days.

(21) Appl. No.: 17/438,628

(22) PCT Filed: Mar. 12, 2020

(86) PCT No.: PCT/US2020/022431
§ 371 (c)(1),
(2) Date: Sep. 13, 2021

(87) PCT Pub. No.: WO2020/190648
PCT Pub. Date: Sep. 24, 2020

(65) Prior Publication Data
US 2022/0218198 A1    Jul. 14, 2022

Related U.S. Application Data

(60) Provisional application No. 62/889,366, filed on Aug. 20, 2019, provisional application No. 62/819,287, filed on Mar. 15, 2019.

(51) Int. Cl.
*A61B 3/11* (2006.01)
*A61B 3/00* (2006.01)
(Continued)

(52) U.S. Cl.
CPC ............ *A61B 3/112* (2013.01); *A61B 3/0008* (2013.01); *A61B 3/0041* (2013.01); *A61B 3/14* (2013.01);
(Continued)

(58) Field of Classification Search
CPC ..... A61B 3/112; A61B 3/0008; A61B 3/0041; A61B 3/14; A61B 5/4088; A61B 5/4585;
(Continued)

(56) References Cited

U.S. PATENT DOCUMENTS

| | | | |
|---|---|---|---|
| 5,109,161 A | * | 4/1992 | Horiuchi ................. G01S 17/08 356/3.08 |
| 2006/0077348 A1 | * | 4/2006 | Gorin ................... A61B 3/0008 351/205 |

(Continued)

FOREIGN PATENT DOCUMENTS

WO    WO-2015120438 A1 * 8/2015 ........... A61B 3/0025

OTHER PUBLICATIONS

International Search Report and Written Opinion in International Patent Application No. PCT/US2020/022431, mailed Jul. 20, 2020 (10 pages).

*Primary Examiner* — Sharrief I Broome
(74) *Attorney, Agent, or Firm* — Nixon Peabody LLP

(57) ABSTRACT

Systems and methods are disclosed for measuring pupillary light reflex and detecting diseases based on eyes features and trends in pupillary and other eye related features. In one example, disclosed is a system for evaluating pupillary features includes a device, a camera, a distance detector, a memory, and a control system. Image data corresponding to an eye of a user is received from the camera. Distance data associated with the eye of the user is received from the distance detector. The distance data is processed to determine a distance of the at least one eye of the user from the
(Continued)

distance detector. The image data and the distance are processed to determine at least one pupillary feature. Based on the at least one pupillary feature, a health status associated with the user is determined.

20 Claims, 25 Drawing Sheets

(51) Int. Cl.
*A61B 3/14* (2006.01)
*A61B 5/00* (2006.01)
*G06T 5/92* (2024.01)
*G06T 7/00* (2017.01)
*G06T 7/521* (2017.01)
*G06T 7/62* (2017.01)
*G16H 50/30* (2018.01)

(52) U.S. Cl.
CPC .......... *A61B 5/4088* (2013.01); *A61B 5/4845* (2013.01); *G06T 5/92* (2024.01); *G06T 7/0012* (2013.01); *G06T 7/521* (2017.01); *G06T 7/62* (2017.01); *G16H 50/30* (2018.01); *G06T 2207/10028* (2013.01); *G06T 2207/30041* (2013.01)

(58) Field of Classification Search
CPC .. G06T 7/62; G06T 7/521; G06T 5/92; G06T 7/0012; G06T 2207/10028; G06T 2207/30041; G16H 50/30
USPC .......................................................... 351/206
See application file for complete search history.

(56) References Cited

U.S. PATENT DOCUMENTS

| | | | | |
|---|---|---|---|---|
| 2011/0172555 | A1* | 7/2011 | Kolanko | A61B 3/11 600/558 |
| 2012/0268715 | A1* | 10/2012 | Stark | A61B 5/163 351/205 |
| 2012/0293772 | A1* | 11/2012 | Vogler | G06V 40/19 351/210 |
| 2013/0002722 | A1* | 1/2013 | Krimon | G06F 3/012 345/661 |
| 2013/0222589 | A1* | 8/2013 | Lalonde | G08G 1/165 348/148 |
| 2015/0199559 | A1* | 7/2015 | Sztuk | G06F 3/013 348/78 |
| 2016/0045108 | A1* | 2/2016 | Wu | A61B 3/14 351/209 |
| 2016/0338640 | A1* | 11/2016 | Chan | A61B 5/352 |
| 2018/0121608 | A1* | 5/2018 | Gross | G16H 20/30 |
| 2018/0199810 | A1* | 7/2018 | Li | G06T 7/60 |
| 2018/0296086 | A1* | 10/2018 | Korb | A61B 3/0041 |
| 2019/0012784 | A1* | 1/2019 | Wiley | G06T 7/0012 |

* cited by examiner

METHOD AND SYSTEM FOR MEASURING PUPILLARY LIGHT REFLEX WITH A MOBILE PHONE

CROSS-REFERENCE TO RELATED APPLICATIONS

This application is a U.S. National Stage of International Application No. PCT/US2020/022431, filed Mar. 12, 2020 which claims priority to and the benefit of U.S. Provisional Pat. Appl. No. 62/819,287, filed Mar. 15, 2019, and of U.S. Provisional Pat. Appl. No. 62/889,366, filed Aug. 20, 2019, each of which is hereby incorporated by reference herein in their entireties.

TECHNICAL FIELD

This disclosure relates generally to systems and methods for measuring pupillary response, and more particularly, to systems and methods for measuring pupillary light reflex with a mobile phone.

BACKGROUND OF THE INVENTION

Currently, the healthcare industry focuses on solutions to diseases in the form of goods and services across key phases in the health-time continuum. These phases include a prevention phase and an intervention phase. The prevention phase involves maintaining wellness in a consumer's daily life. The intervention phase involves the diagnosis and treatment of developed disease(s) in a medical setting. Further, detection of issues associated with an individual's health are typically limited to routine physical examination or appointments scheduled by the individual after the onset of symptoms. In order to diagnose diseases or disorders, healthcare professionals generally rely on the individual to first present with symptoms.

Signs and symptoms are abnormalities that can indicate a potential medical condition. A symptom is subjective and can be apparent only to a patient, for example, back pain or fatigue. A sign is evidence of a disease that can be observed by others, for example, a skin rash or a lump. In some instances, the sign may be subjective and/or objective, and is often accepted as an indicator of the disease. Once the patient presents with symptoms, subjective observation of signs by the medical professional, in combination with objective molecular or imaging diagnostic testing, allows for diagnosis of the disease.

However, sometimes, access to a medical professional can be physically limiting and costly. It is also becoming increasingly limited in interaction time with the medical professional, for each medical appointment. For example, molecular diagnostic tests are expensive, and typically require invasive access to a patient's blood or tissue. Imaging diagnostic tests are similarly expensive, and require the patient to have physical access to specialized equipment, such as magnetic resonance imaging (MRI). Although these methods of diagnosing developed diseases have been the standard paradigm in healthcare, it often results in delayed identification of diseases, and also often too late. Consequently, this standard paradigm often results in decreased quality of life or survival rates and limited interventional treatment options, which may also be more costly, ineffective, or even altogether unavailable.

The present disclosure is directed to solving these problems and addressing other needs.

SUMMARY

According to some implementations of the present disclosure, a system for evaluating pupillary or other eye features includes a device, a camera, a distance detector, a memory, and a control system. The device includes a front and a back. The camera is located on the front of the device. The distance detector is located on the front of the device. The distance detector includes an emitter and a receiver. The memory stores machine-readable instructions. The control system includes one or more processors configured to execute the machine-readable instructions. Image data corresponding to at least one eye of a user is received from the camera. Distance data associated with the at least one eye of the user is received from the distance detector. The distance data is processed to determine a distance of the at least one eye of the user from the distance detector. The image data and the distance are processed to determine at least one pupillary feature. Based at least in part on the at least one pupillary feature, a health status associated with the user is determined.

In some implementations, the at least one pupillary feature includes a diameter of a pupil of the at least one eye of the user. In some implementations, the at least one pupillary feature includes an absolute measurement. In some implementations, the at least one pupillary feature is determined based at least in part on a preexisting measurement of a diameter of a corresponding iris of the at least one eye of the user.

In some implementations, a first field of view of the camera is similar to a second field of view of the distance detector.

In some implementations, a brightness and a contrast of the at least one eye of the user are adjusted relative to a background associated with the user. In some implementations, a brightness and a contrast of the at least one eye of the user and a face of the user are adjusted relative to a background associated with the user.

In some implementations, frames with blinking associated with the at least one eye of the user are removed. In some implementations, aberrations with eye movements associated with the at least one eye of the user are removed.

In some implementations, the health status includes a pupillary light reflex. In some implementations, includes a level of impairment. In some implementations, the level of impairment includes a level of alcohol impairment. In some implementations, the health status includes a progression of Alzheimer's disease.

In some implementations, the receiver of the distance detector includes an image capture assembly. In some implementations, the camera includes the receiver of the distance detector. In some implementations, the camera includes the distance detector. In some implementations, the device includes the camera and the distance detector.

In some implementations, the system further includes a display located on the front of the device. In some implementations, the device further includes a visible light emitter on the front of the device. In some implementations, the device is a mobile device.

In some implementations, the emitter of the distance detector includes a visible light emitter. In some implementations, the emitter of the distance detector includes a light source configured to transilluminate a transparency with optical radiation to project an uncorrelated pattern of spots onto the at least one eye of the user, the transparency containing the uncorrelated pattern of spots.

According to some implementations of the present disclosure, a method for evaluating pupillary features is disclosed. Image data corresponding to at least one eye of a user, the camera being located on a front of a device is received from a camera. Distance data associated with the at least one eye of the user is received from a distance detector. The distance detector is located on the front of the device and includes an emitter and a receiver. The distance data is processed to determine a distance of the at least one eye of the user from the distance detector. The image data and the distance are processed to determine at least one pupillary feature. Based at least in part on the at least one pupillary feature, a health status associated with the user is determined.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1A:
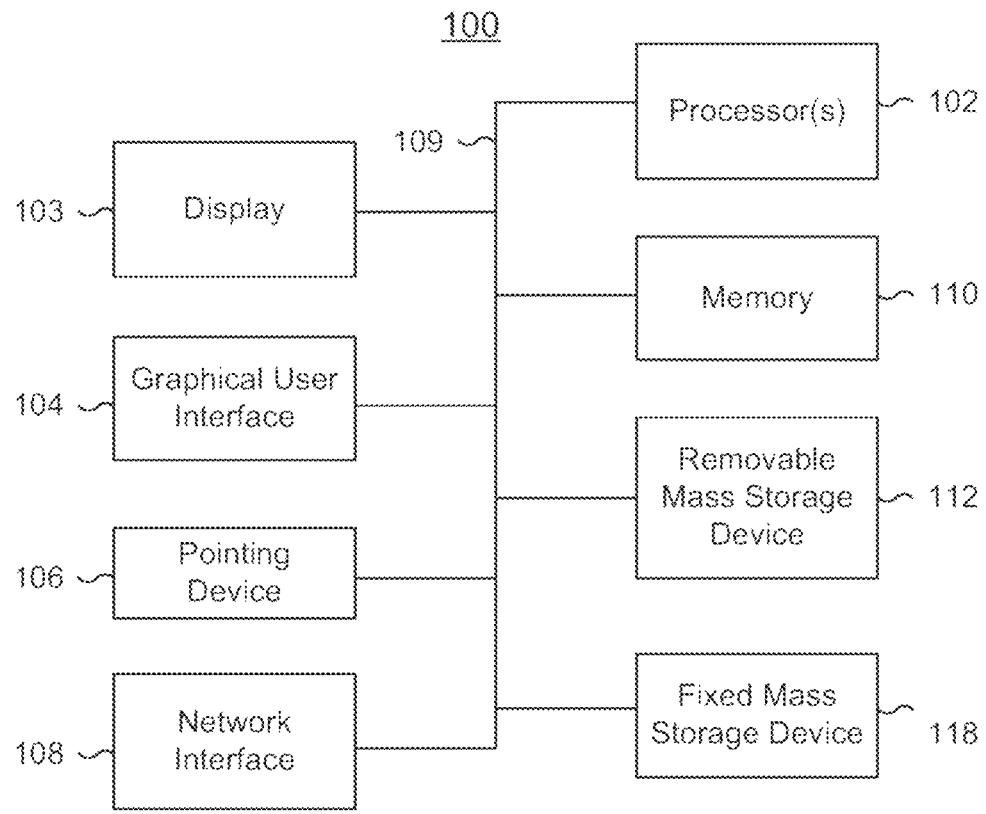
FIG. 1A is a block diagram of a system for detecting developing diseases, disorders, or disease precursors using digital phenotypic data, according to some implementations of the present disclosure.

While the present disclosure is susceptible to various modifications and alternative forms, specific implementations have been shown by way of example in the drawings and will be described in further detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described herein with reference to example applications for illustration.
Introduction The present disclosure can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the present disclosure may take, may be referred to as techniques. In general, the order of the steps of disclosed processes may be altered within the scope of the present disclosure. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more implementations of the present disclosure is provided herein along with accompanying figures that illustrate the principles of the present disclosure. The present disclosure is described in connection with such implementations, but the present disclosure is not limited to any implementation. The scope of the present disclosure is limited only by the claims and the present disclosure encompasses numerous alternatives, modifications and equivalents. Numerous specific details are set forth in the following description in order to provide a thorough understanding of the present disclosure. These details are provided for the purpose of example and the present disclosure may be utilized according to the claims without some or all of these specific details. For the purpose of clarity, technical material that is known in the technical fields related to the present disclosure has not been described in detail so that the present disclosure is not unnecessarily obscured.

A method and system for detecting a developing disease, disorder, or disease precursor are described. Phenotypic data including phenotypic sensor data are received from a client device. The client device includes sensors. The phenotypic sensor data are captured by these sensors. This phenotypic data relates to behavioral and/or an external physiological processes and/or expressions that may be captured by one or more various sensors. Using a processor, it is determined whether a developing disease, disorder, or disease precursor exists based on the phenotypic data. Phenotypic data which correspond to a known developing disease are referred to in aggregate as a digital marker. A detection alert is provided to the client device for a disease corresponding to the digital marker if it is determined that the digital marker exists.

As used herein, phenotypic data are data that is physically perceptible without the use of a molecular measure, such as a blood panel. Molecular measures are distinct from phenotypic measures in part because for the molecular measures to generate data, invasive access to a physical intermediary (such as a molecule or protein from the individual) is required. In contrast, phenotypic data may be more readily captured, easily digitized, and thus may be orders of magnitude more voluminous. Phenotypic data need not be perceptible by humans, but it can be observed and captured by a device through its particular sensing modality. For example, a device such as a smart phone has multi-modality sensors, or sensors which generate data based on multiple types of physical phenomenon. Such multi-modality sensors may include optical sensors (a camera and ambient light sensor), acoustic sensors (microphone), mechanical sensors (accelerometer and gyroscope), physical sensors (touch screen), and infrared sensors.

However, sensors in smart phones are not currently utilized to capture a broad range of phenotypic data. The camera, for example, is primarily used to take photographs and capture video. Similarly, a smart watch includes sensors that can capture traits expressed through multiple physiologic pathways, such as optical sensors, photoplethysmograph (PPG) heart rate sensors (HR), and oxygen saturation level (SpO2) sensors. Further, as used herein, phenotypic signs are typically expressed and generated as data outside of the medical setting, or in the life setting. For example, phenotypic data may be captured at home and while users goes about their daily routines.

The healthcare industry expends significant resources on extracting medical value from the medical data typically generated in a medical setting—where a miniscule amount of a consumer's total time in life is actually spent. Medical data continues to be siloed, unstructured, contextually biased, and intermittently generated, longitudinally in time. Medical settings offer access to tremendous medical experience and clinically validated diagnostics. However, issues still remain in the ability of medical data to adequately assist in maintaining and improving patients' health.

The method and system described herein can be applied outside of the medical setting, from within the life setting. This offers tremendous potential to leverage a significantly larger observation window than in the medical setting. The larger observation window provides access to time a consumer may be expressing signs of a developing disease, but which may otherwise be missed or dismissed by the host of the disease or too subtle for a medical professional to observe.

Life data now has the possibility to be generated in the broader life setting. Life data can quantify a consumer's phenotype, is generated in situ, and provided by devices such as personal computing devices, in particular mobile smart devices. As such, life data includes phenotypic data as described herein. Life data, as well as phenotypic data, can be divided into two subgroups: active data and passive data. Active data includes data that requires active input from the users to be generated. Passive data, such as certain sensor data and device usage patterns, are collected without requiring any active participation from the user.

In contrast to passive phenotypic data, the generation of medical data is inherently only active, typically confined in time and location to a medical setting such as a medical professional's office, hospital, or laboratory and requires active participation from both the consumer and medical professional. The method and system described herein, which utilize phenotypic data, do not require invasive or physical access to biologic molecules for these phenotypic data, allowing such data to be generated orders of magnitude more voluminously, frequently, affordably, conveniently, objectively, and contextually.

The method and system described herein provide a platform in which phenotypic data generated from user smart devices and medical data (e.g., from open-API medical data aggregating services, from data-generating Provider networks, and/or other sources) can be used to objectively and accurately train disease detection models. The medical data, such as diagnostic and other feature-relevant information in patient medical records, allow labeled outcome data to ground-truth information for training the supervised computational learning process model to be generated. For example, such data may encompass those extracted from medical reports, lab tests, medical imaging devices, commercial genetic tests, medical claims data, prescription data, and other medical data generated in a medical setting.

Models ingest a user's passively and actively generated phenotypic data that are captured using smart devices. Labeled endpoints assist in the training of the model to provide a correlative relationship between phenotypic data and molecular medical data during disease expression. Further, medical records and/or medical device data can be used as supplementary inputs for the detection of co-morbidities using a similar learning process. For example, a deep learning model can be trained to use scalar and multidimensional phenotypic data with diagnosis labels provided by the medical data.

Scalar and multidimensional phenotypic data can also be mapped to other medical data. This synthesis of continuously generated phenotypic data with clinically generated medical data under a singular platform yields the ability to computationally train and quantitatively map phenotypic data to clinical outcomes. Using such models or other analytic mechanisms, phenotypic data can be used to detect developing diseases, disorders and/or disease precursors.

Thus, the method and system utilize the large observable window of time outside the medical setting, from within the life setting. Diseases are frequently expressed via subtle and intermittent non-molecular, or phenotypic, signs. Many of these expressions can be digitally captured continuously, conveniently, contextually, and objectively using the same multi-modality sensors within the smart devices that are increasingly populating user's everyday life settings. The method and system generate phenotypic measures of physiologic and behavioral features from the body and the environment around the body (phenotypic data); analyze the phenotypic data in conjunction with aggregated medical data, which is generated in a medical setting such as a doctor's office, hospital, or laboratory; discover "digital markers"; and detects developing diseases, disorders, and disease precursors from a user's life setting. Thus, a user may be led to earlier confirmatory diagnoses in a medical setting, earlier interventional treatment, and improved medical outcomes.

Pupillary Responses

Pupils constrict and dilate in response to various external (e.g., light) and internal (e.g., cognitive/emotional) stimuli. Pupil responses are evaluated for many aspects of physiologic and behavioral health. Some conventional measurement methods use a pupilometer. Pupilometers are expensive, costing as much as $4,500. In addition, pupilometers are mainly used in medical settings, and must be used by a trained clinician. Other conventional measurement methods use a penlight exam, where a clinician directs a penlight towards the patient's eyes and observes the pupils' responses.

The conventional measurement methods may seem simple to perform, but have substantial qualitative drawbacks, including a lack of standardization, a need for deliberate training, variances between different measuring-operators over time, and poor inter-observer reliability or reproducibility. Penlight exams are also conventionally used in emergency first aid situations, where rapid, qualitatively-crude assessments, accessibility, and convenience are prioritized over precision. Furthermore, even semi-automated conventional methods for measuring pupillary response require new or external physical hardware to ensure any or all of (1) proper ambient lighting conditions, (2) proper alignment of face/eyes guided by the front of mobile device display, (3) sufficient stimulus for pupillary response, and/or (4) adequate processing power for performing external image processing/feature extraction.

In addition to the disadvantages of conventional pupillary measurement systems, these devices use visible light as the stimulus source followed by another visible light as the illumination source for image capture; in some implementations, use of the visible light spectrum to measure the pupil post the stimulation phase, may catalyze unintentional pupillary responses, akin to the "observer effect" in physics where the mere observation of a phenomenon inevitably changes that phenomenon—often the result of instruments that, by necessity, alter the state of what they measure in some manner. Furthermore, conventional systems need to (1) provide enough light stimulus to achieve the high levels of contrast required for pupil-iris segmentation, (2) ensure moderately- to well-lit lighting conditions to illuminate the face for adequate image capture.

Lastly, these conventional methods typically may only catch signs of disease occurrence after the disease is acutely symptomatic or has been progressively developed, which may be beyond the most treatable phase of the disease.

Thus, the various examples of the present disclosure are directed towards a system for evaluating pupillary light reflex, such as one or more pupillary features. The system includes a mobile device, a camera, a display, a processor, and a memory. The mobile device includes a front side and a back side; the camera and the display are located on the front side of the mobile device. The memory includes a plurality of code sections executable by the processor. The plurality of code sections include a series of instructions. The instructions provide for emitting at least one visible light stimulus by the display. The instructions then provide for receiving, from the camera, image data corresponding to at least one eye of a user. The instructions then provide for processing the image data to identify at least one pupillary feature. The instructions then provide for determining a health status based on the at least one pupillary feature.

In some implementations, the instructions further provide for outputting the health status at the display. In some implementations, processing the image data to identify at least one pupillary feature includes preprocessing the received image data. In some implementations, identifying at least one pupillary feature based on the received image data includes segmenting the received image data to determine first data portions corresponding to a pupil of the eye and second data portions corresponding to an iris of the eye.

In some implementations, the at least one pupillary feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

In some implementations, determining a health status based on the at least one pupillary feature further includes: (1) determining a difference between each of the at least one pupillary feature and a corresponding healthy pupil measurement, and (2) determining the health status based on the determined difference for each of the at least one pupillary feature and the at least one pupillary feature. For example, the corresponding healthy pupil measurement is retrieved, by the processor, from an external measurement database.

In some implementations, emitting at least one visible light stimulus by the display includes (1) receiving first image data of the eye when no light stimulus is provided by the display, (2) determining an amount of luminous flux to provide based on the first image data, (3) determining an area of the display to output the determined amount of luminous flux, and (4) outputting the determined amount of luminous flux on the determined area of the display. In some implementations, second image data of the eye is received after outputting the luminous flux. In some implementations, the output luminous flux is adjusted based on the second image data.

In some implementations, the instructions further provide for tagging a first pupil response based on the received image data. Second image data is then received. The instructions then provide for determining a change in lighting conditions based on the second image data. A second pupil response is then tagged.

The present disclosure further provides an example method for evaluating pupillary light reflex. The method provides for emitting at least one visible light stimulus by the display. The method then provides for receiving, from the camera, image data corresponding to an eye of a user. The method then provides for processing the image data to identify at least one pupillary feature. The method then provides for determining a health status based on the at least one pupillary feature. Additional examples of this method are as described herein with respect to the example system.

The present disclosure further provides for a non-transitory machine-readable medium comprising machine-executable code. When executed by at least one machine, the machine-executable code causes the machine to emit at least one visible light stimulus by the display. The code then provides for receiving, from the camera, image data corresponding to an eye of a user. The code then provides for processing the image data to identify at least one pupillary feature. The code then provides for determining a health status based on the at least one pupillary feature. Additional examples of this code are as described herein with respect to the example system.

In another example embodiment, the present disclosure provides another system for evaluating pupillary light reflex. The system includes a hardware device, a camera, a display, a processor, and a memory. The hardware device includes a front side and a back side; the camera and the display are located on the front side of the hardware device. The memory includes a plurality of code sections executable by the processor. The code sections include instructions for emitting at least one visual stimulus by the display. The instructions further provide for emitting at least one non-visible light by an infrared emitting device. The instructions then provide for receiving, from the camera or an infrared detector, image data corresponding to an eye of a user. The instructions then provide for processing the image data to identify at least one pupillary feature. The instructions then provide for determining a health status based on the at least one pupillary feature.

In some implementations, the non-visible light emission with a wavelength between 700 nm and 1000 nm. In some implementations, the non-visible light emission includes far infrared wavelengths. In some implementations, the camera is an infrared camera. In some implementations, identifying at least one pupillary feature based on the received image data includes (1) determining image contrast of the received image data, (2) determining that the image contrast is lower than a threshold contrast level, and (3) outputting, on the display, a prompt for the user to provide second image data at a more dimly lit location. For example, the at least one pupillary feature is determined based on the second image data.

In some implementations, the at least one pupillary feature includes at least one of: pupil response latency, constriction latency, maximum constriction velocity, average constriction velocity, minimum pupil diameter, dilation velocity, 75% recovery time, average pupil diameter, maximum pupil diameter, constriction amplitude, constriction percentage, pupil escape, baseline pupil amplitude, post-illumination pupil response, and any combination thereof.

In some implementations, identifying at least one pupillary feature based on the received image data further includes segmenting the received image data to determine data portions corresponding to a pupil of the eye and data portions corresponding to an iris of the eye. In some implementations, the hardware device is a headset. In some implementations, the hardware device is a smartphone.

An example system provides a display and a camera on the same side of a device; the display provides a visible light stimulus to stimulate a user's eye and catalyze a pupillary reflex. In some examples, this is using a light source on a device, or by instructing the user to close their eyes for a predetermined amount of time. The camera then receives image data of the pupillary reflex. Therefore, an example device according to the present disclosure can provide a more scalable (accessible, affordable, and convenient) and more accurate (objective and quantitative) system than current systems and methods, which can be used by the user with or without a health professional or non-health professional. In some examples, either the backward or forward facing camera on a mobile device may be utilized. In some examples, using the backward facing camera and flash on the back of a smartphone has been attempted to be used to measure pupillary light reflex, but a user would be unable to self-measure their PLR using that system, and thus would require dependence on a second measurement-operator and potential longitudinal measurement inconsistencies stemming from multiple measurement-operators.

However, prior systems have not attempted to use the front facing camera because the front of mobile devices do not include a flash and therefore a stimulus could not be generated to initial the pupillary light reflex. Accordingly, the inventors discovered the display on the front of a smart phone or similar device could be utilized to provide the stimulus, based on the methods and features described herein. This is very advantageous, because using a front-facing camera and display allows the users themselves to more accurately and scalably/frequently perform the pupillary light reflex measurement using a smart phone or other related device.

For instance, the user can line up the eyes correctly because the display is also on the front side of the device, without help from another individual. This allows the user to frequently perform the measurement because they do not require another caregiver to perform the measurement. Thus, the system allows the user to collect data more frequently and obtain longitudinal data on their health conditions (whereas single measurements may not be sufficient to identify certain conditions where longitudinal data is required, including for establishing baselines and deviations from baselines).

Additionally, utilizing the display to provide the stimulus will allow the system to have more precise control and variability of the stimulus given the range of intensities and colors that may be displayed. In some examples where the system determines psychosensory pupil response (PPR), the display could be used to provide mental stimulus including providing a mental task or instructions to perform a task that requires mental effort while the camera on the same side as the display evaluates pupillary features and determines PPR. Finally, in some implementations that utilized infrared detection, this system may be particularly advantageous because the infrared detection will allow a sufficient pupillary response to be generated by the eye, because measurement light will not cause a secondary response of the pupils—which is important because the display has a lower maximum intensity than a rear facing flash, and thus a secondary response may prohibit the ability to record a sufficient pupillary light reflex.

In some implementations, the disclosed system includes a smartphone or other handheld computing device. Such a system allows frequent and accurate data collection, which can provide important quantitative data on user health. In some implementations, as discussed further herein, the present disclosure provides for collection of longitudinal health data, which can be used to create baseline pupillary metric measurements for a user. Therefore, the present disclosure provides measurements pre-diagnosis, pre-trauma, and/or pre-disease, which can be used to monitor disease and/or trauma progression and/or establish an individualized longitudinal healthy baseline.

In some implementations, the visible stimulus generates sufficient photonic energy to catalyze a full pupillary reflex. Example methods further include collecting data before the light intensity threshold is reached, and determining pupillary metrics as a function of other factors that affect pupillary response. In some examples, use of a front-facing display and front-facing camera further allows the disclosed system to control the ambient lighting conditions during image capture to ensure that a secondary accidental pupil response is not initiated when measuring the first, intentional pupil response. In some implementations, an example method detects ambient light levels to account for an effect that the ambient light levels had on the detected pupillary metrics. In some implementations, the data collected before the light intensity threshold is reached provides baseline values for a user's pupillary metrics.

Some implementations of the present disclosure further provide for using a visible stimulus to illuminate the face and then using a non-visible emission for image capture. Use of the non-visible avoids unintentionally stimulating reflexes that adulterate the data. Additionally, due to the high level of contrast required between the light stimulus intensity and ambient lighting conditions in order to catalyze pupillary light reflex, performing an assessment in dimly-lit conditions may be beneficial in some implementations. In some implementations, though, performing an assessment in a dimly-lit area poses problem as the darkness of the room may interfere with capturing a high-quality eye image. For example, there is often minimal contrast between the pupil and iris components, particularly in an individual with higher pigmented, or darker irises. Distinguishing between these two features is critical to properly segment the features for extraction and metric computation. An infrared camera or other infrared hardware further provides high-resolution pupil images for effective feature segmentation.

Systems and Methods for Measuring Phenotypic Data

FIG. 1A is a block diagram of a computer system 100 usable in a system for detecting developing diseases, disorders, or disease precursors using digital phenotypic data. Other computer system architectures and configurations can be used for carrying out the processing of the disclosed technique. Computer system 100, made up of various subsystems described herein, includes at least one microprocessor subsystem (also referred to as a central processing unit, or CPU) 102. For example, processor 102 can be implemented by a single-chip processor or by multiple processors. Processor 102 may have multiple cores in some implementations.

In some implementations processor 102 is a general purpose digital processor which controls the operation of the computer system 100. Using instructions retrieved from memory 110, processor 102 controls the reception and manipulation of input data, and the output and display of data on output devices. In some implementations, processor 102 includes and/or is used to provide functions described herein with respect to system 150 of FIG. 2 and methods 200, 210 and 230. In some implementations, processor 102 may be considered to include a neural network or other platform usable in deep learning.

Processor 102 is coupled bi-directionally with memory 110 which can include a first primary storage, typically a random-access memory (RAM), and a second primary storage area, typically a read-only memory (ROM). Primary storage can be used as a general storage area and as scratch-pad memory, and can also be used to store input data and processed data. Primary storage can also store programming instructions and data, in the form of data objects and text objects, in addition to other data and instructions for processes operating on processor 102. Primary storage typically includes basic operating instructions, program code, data and objects used by processor 102 to perform its functions (e.g., programmed instructions). For example, memory 110 may include any suitable computer-readable storage media, described herein, depending on whether, for example, data access needs to be bi-directional or unidirectional. Processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. Storage device 112 may also include computer-readable media such as magnetic tape, flash memory, signals embodied on a carrier wave, PC-CARDS, portable mass storage devices, holographic storage devices, and other storage devices, either local or remote. A fixed mass storage device 118 can also provide additional data storage capacity. The most common example of mass storage is a hard disk drive. Mass storage devices at 112 and 118 generally store additional programming instructions, data, and the like that typically are not in active use by processor 102. It will be appreciated that the information retained within mass storage devices 112 and 118 may be incorporated, if needed, in standard fashion as part of memory 110 (e.g. RAM) as virtual memory.

In addition to providing processor 102 access to storage subsystems, bus 109 can be used to provide access other subsystems and devices as well. In the described implementation, these can include a display 103, a graphical user interface 104, a pointing device 106, and a network interface 108, as well as an auxiliary input/output device interface, a sound card, speakers, and other subsystems as needed. The pointing device 106 may be a mouse, stylus, track ball, or tablet, and is useful for interacting with graphical user interface 104.

The network interface 108 allows processor 102 to be coupled to another computer, computer network, or telecommunications network using a network connection as shown. Through the network interface 108, it is contemplated that the processor 102 can receive information (e.g., data objects or program instructions) from another network, or can output information to another network in the course of performing the above-described method steps. Information, often represented as a sequence of instructions to be executed on a processor, may be received from and outputted to another network, for example, in the form of a computer data signal embodied in a carrier wave. An interface card or similar device and appropriate software implemented by (e.g. executed or performed on) processor 102 can be used to connect computer system 100 to an external network and transfer data according to standard protocols. For example, various process implementations disclosed herein can be executed on processor 102, or can be performed across a network such as the Internet, intranet networks, or local area networks, in conjunction with a remote processor that shares a portion of the processing. Additional mass storage devices (not shown) may also be connected to processor 102 through network interface 108.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, implementations of the disclosed technique further relate to computer storage products with a computer readable medium that contains program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. The computer-readable medium can also be distributed as a data signal embodied in a carrier wave over a network of coupled computer systems so that the computer-readable code is stored and executed in a distributed fashion. Examples of program code include both machine code, as produced, for example, by a compiler, or files containing higher level code that may be executed using an interpreter.

The computer system shown in FIG. 1A is an example of a computer system suitable for use with the various implementations disclosed herein. Other computer systems suitable for such use can include additional or fewer subsystems. In addition, bus 109 is illustrative of any interconnection scheme serving to link the subsystems. Other computer architectures having different configurations of subsystems can also be utilized.

Figure 1B:
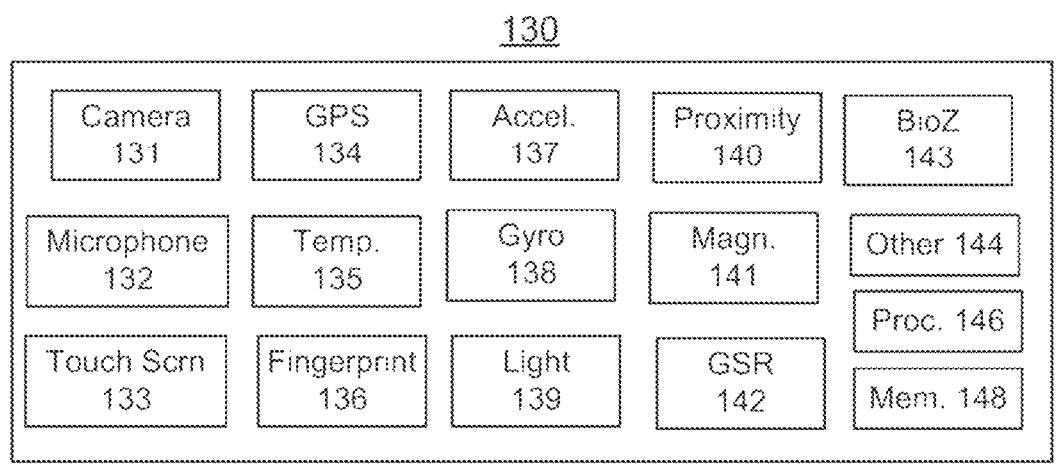
FIG. 1B is a block diagram of a system for detecting developing diseases, disorders, or disease precursors using digital phenotypic data, according to some implementations of the present disclosure.

FIG. 1B is a block diagram of a client device 130 usable in a system for detecting developing diseases, disorders, or disease precursors (also collectively referred to herein as "disease") using digital phenotypic data. Client device 130 may be a mobile or other computing device including one or more sensors. For example, client device 130 may include smart phones; tablets; wearables such as smart watches, or other wearable sensor devices; automobiles; smart home devices such as IoT devices; and/or any other analogous devices capable of receiving and interpreting a physical signal. Client device 130 includes processor(s) 146 and memory 148 that are analogous to processor(s) 102 and memory 110/112, respectively.

In some implementations, client device 130 also incorporates a number of sensors 131 through 144 usable in obtaining phenotypic data. For example, client device 130 may include one or more of camera(s) 131 that may include an ultra-high definition camera, microphone(s) 132, touch screen(s) 133, global positioning satellite (GPS) system(s) 134, temperature sensor(s) 135, fingerprint identity sensor(s) 136, accelerometer(s) 137, gyroscope(s) 138, light sensor(s) 139, proximity sensor(s) 140, magnetometer(s) 141, galvanic skin response (GSR) sensor(s) 142, bioimpedance sensor(s) 143, and other sensors 144.

In some implementations, other sensors 144 cancan include infrared sensor(s), photoplethysmograph (PPG) sensor(s), electrocardiogram (ECG) sensor(s), moisture sensor(s), humidity sensor(s), digital barometric pressure sensor(s) and/or additional sensors not discussed herein. Although sensors 131 through 144 are shown in FIG. 1B, client device 130 may include a subset of sensors 131-144, different sensor(s) and/or additional sensor(s). For example, client device 130 may include a range of sensors and/or devices not explicitly disclosed herein as new devices are released. Sensors 131-144 may be controlled via processor 146 to capture data usable in detecting developing diseases, disorders, or disease precursors.

Figure 2:
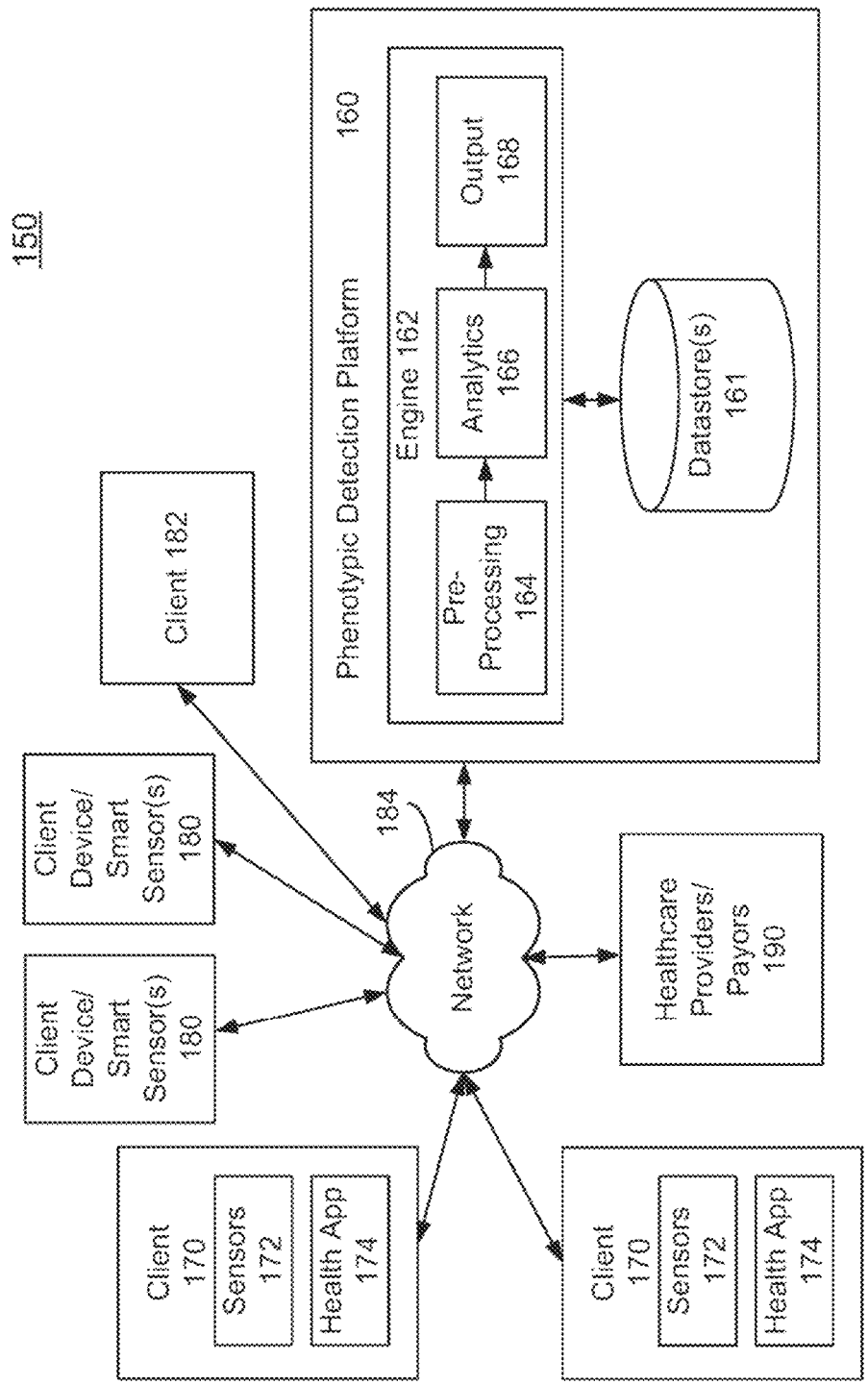
FIG. 2 is a block diagram of a system for detecting developing diseases, disorders, or disease precursors using digital phenotypic data, according to some implementations of the present disclosure.

FIG. 2 is a block diagram of a system 150 for detecting developing diseases, disorders, or disease precursors using digitally-generated phenotypic data. In particular, FIG. 2 illustrates one view of an implementation of phenotypic detection platform 160 and client devices 170, 180, and 182 coupled via network 184. Also shown are healthcare provider/payor systems (hereinafter "provider systems") 190. Network 184 includes one or more networks between devices 170, 180, 182, and 190 and phenotypic detection platform, such as the Internet, intranet networks, or local area networks. For simplicity, only certain portions of phenotypic detection platform 160, client devices 170, 180 and 182 and provider system(s) 190 are shown in FIG. 2. Although only five client devices 170, 180, and 182 are shown as coupled to phenotypic detection platform 160, another number of clients typically utilize phenotypic detection platform 160. Phenotypic detection platform 160 may be implemented using computer system 100.

Client devices 170, 180, and 182 provide phenotypic and other data to phenotypic detection platform 160. Client devices 170 may be implemented using client 130. For example, client devices 170 may include mobile devices such as smart phones or wearables described herein. Client devices 170 include sensor(s) 172 analogous to those described herein. In addition, client devices 170 include health application 174. Health application 174 receives sensor data captured by sensors 172, optionally performs processing on the sensor data and provides phenotypic data to phenotypic detection platform 160. Health application 174 also receives communications from phenotypic detection platform 160 and may be used to perform active tests on a user on client device 170.

The phenotypic data described herein can include active data and/or passive data. Passive data are collected by sensor(s) 172 during regular use of client device 170, without requiring the user to perform any specialized tasks, while the user performs day-to-day activities unrelated to the collection of data. For example, passive data may include data taken by an accelerometer while the user walks, GPS data taken by a GPS system indicating where the user is moving geographically, or heart rate data taken while a user exercises as part of the user's daily routine.

In some implementations, passive data may include sound data taken by a microphone or video/photographic data taken by a camera if the user is not specifically instructed to perform tasks for such data. For example, sound data captured while a user is sleeping (and with the user's permission) is passive data that can be captured by sensor(s) 172. Passive data may be collected continuously or semi-continuously (for example for intervals of at least one hour, a few hours or more) during use of client device 170.

In some implementations, active data includes data for which the user performs particular functions as directed by health application 174 and/or a healthcare provider. Active data can include a video capture of the user's eye if the user is instructed to capture an image of the eye, for example for pupil velocity during constriction of the pupil in response to a light being projected to the user's eye. Active data can include heart rate or position of the user's hand as determined by a gyroscope while the user performs specified tasks with the intent of capturing the respective data as those tasks are performed.

Although active data are generally collected during a short time interval (less than a few minutes), in some cases, active data may be collected for at least an hour, several hours, or more. Passive and/or active sensor data relates to information that is physically observable by sensor(s) 172 and can be captured by sensors 172. This phenotypic data may be directly provided to phenotypic detection platform 160 or may be processed by health application 174 prior to being sent to phenotypic detection platform 160.

In addition to managing active and passive phenotypic data provided to phenotypic detection platform 160, health application 174 may also provide medical, demographic, and/or other data to phenotypic detection platform 160 and/or provider systems 190. In some implementations, the user's identity may be included with the data provided to provider systems 190. In other cases, the user's identifying information may be removed from the data sent to provider systems 190, thereby preserving the user's privacy. For example, upon engaging with health application 174, a user may be prompted to enter their medical history, family history, and/or other information that may be useful in detecting developing diseases, disorders, or disease precursors.

In some implementations, a family or medical history of high cholesterol or heart attacks may be useful in phenotypic detection platform 160 analyzing phenotypic data to determine whether a developing disease, disorder, or disease precursor exists. Health application 174 may also provide data from other health-related devices, including data from molecular measures, which is captured in or out of the medical setting. For example, the user can enter the results from at-home medical devices/trackers (prescribed or over-the-counter).

Such at-home health-related devices can include prescription drug trackers, blood glucose monitors, breath analyzers, thermometers, and the like. In some implementations, such at-home health-related devices may be smart devices. For such smart devices, results can be automatically entered to the health application 174 if such devices are configured to communicate electronically with client device 170. Similarly, health application 172 may also utilize data from consumer-driven medical tests such as private genetic tests. However, such medical data would be used to supplement the phenotypic data captured by client devices 170, 180, and 182.

Health application 174 can also provide other information to a user. For example, a user can connect to family and friends through social features in the health application. Thus, users may be more motivated to utilize health application 174 and achieve the benefits described herein. Health application 174 may also provide a health score in one or more categories such as cardiovascular health, respiratory health, and/or overall health. The score provided is based upon the phenotypic data sent to phenotypic detection platform 160, other data such as medical data and accepted benchmarks for health in these areas. Health application 174 may provide incentives for use, such as scores, rewards, points, a leaderboard based on engagement with health-oriented features within the application, sharing and competing with friends and family, and/or other health-oriented user-engagement incentives. Health application may also display health tips, links to health literature, links to users' physicians' sites, and other useful health information.

Client devices 180 provide data usable as phenotypic data to phenotypic detection platform 160. Client devices 180 may be mobile or stationary and are distinguished from client devices 170 in that client devices 180 are generally not with a user throughout the user's daily routine. For example, client devices 180 can include smart home systems and/or automobiles. The smart home system may provide information on the temperature the user desires to maintain their home via a thermostat, the time a user spends at home, the amount of sleep a user may be getting (based on whether lights are on or off), the user's in-home movement patterns, and/or other information.

An automobile may also provide thermostat data indicating the temperature at which the user maintains the passenger cabin, GPS data indicating the route(s) a user takes, or time at which the user is driving. Other and/or additional data may be provided by these systems or other client devices. The data provided may be via sensors (such as GPS sensors) and/or a log of commands (such as commands to change the temperature in a home or vehicle). Although not shown, client devices 180 can include health application 174 or an analog. In such implementations, client devices 180 may communicate via network 184 to directly provide phenotypic data to phenotypic detection platform 160. In other implementations, client devices 180 communicate with client devices 170, which provide the phenotypic data from client devices 180 to phenotypic detection platform 160.

Client device 182 may be a stationary desktop computer system or analogous system that allows a user to communicate with phenotypic detection platform 160 but which does not utilize sensors for capturing phenotypic data. For example, a user may check their progress, receive updates via email or in another manner, update personal information, or otherwise utilize phenotypic detection platform 160. In some implementations, however, the microphone or camera on such a client 182 may be used to capture some phenotypic data. Moreover, client 182 may utilize a pointing device 106, such as a mouse, whose use by the user could be measured. For example, client 182 may communicate phenotypic detection data regarding the user's mouse movements to phenotypic detection platform 160.

Client devices 170, 180 and 182 may all be associated with the same user. For example, client devices 170 may include a smart phone and a smart watch; client devices 180 may be in a user's car and home; and client device 182 may be a user's desktop or laptop. Thus, multiple client devices 170, 180, and 182 may provide phenotypic data for a single user. Alternatively, client devices 170, 180 and 192 may be for different users. For example, phenotypic data for a user can only be provided through a single client device 170, such as the user's smart phone.

Provider system(s) 190 are optionally connected with phenotypic detection platform 160. Provider system(s) 190 can also be accessible via client device(s) 170, 180, and/or 182. Provider system(s) 190 may be used to provide medical data for users of clients 170 to phenotypic detection platform 160, to receive phenotypic data from clients 170 and 180 and/or phenotypic detection system 160, to pay for health application 174 or other aspects of system 150, and/or to receive an indication of whether developing diseases, disorders, or disease precursors have been detected by phenotypic detection platform 160.

Provider system(s) 190 may also provide to phenotypic detection platform 160 medical data for a larger population and other medical information. For example, provider system(s) 190 may provide to phenotypic detection platform 160 the results of studies, health data for individuals subscribing to a particular health insurance company or visiting a particular hospital, and/or other information usable in detecting developing diseases, disorders, or disease precursors. Phenotypic detection platform 160 can thus supplement phenotypic and medical data from client devices 170, 180 and 182 with medical and other data from provider systems 190 when determining whether a user exhibits a developing disease, disorder, or disease precursor.

Phenotypic detection platform 160 includes datastore(s) 161 and engine 162. Datastore(s) 161 may include databases and/or other physical and logical storage structures. Datastore(s) 161 store users' medical data, phenotypic data already provided by client device(s) 170, 180, and 182, and identification/administrative information regarding users of client device(s) 170, 180, and 182. Datastore(s) 161 may also store medical data relating to diseases that is used by phenotypic detection platform 160. Medical data includes information generated from clinical studies, or generated in the medical setting, such as molecular detection measures, statistics relating to the data, and other data accepted in the healthcare industry for clinical diagnosis of diseases and disorders. Such medical data can be statistically correlated to phenotypic data by phenotypic detection platform 160.

In the implementation shown, engine 162 includes a pre-processing module 164, analytics module 166 that may include a neural network or other mechanism for performing deep learning or some other form of automated representation learning and classification, and output module 168. Although described in the context of modules 164, 166, and 168, one of ordinary skill in the art will recognize that engine 162 may perform its functions in another manner with another number of modules. Pre-processing module 164 may decompress, change the format of, or otherwise process phenotypic and other data for use by analytics 166. For example, filtering, noise reduction, aggregation, deduplication, and enhancement of certain features of the data may be performed using pre-processing module 164.

In some implementations, weights based on the sensor used to capture the phenotypic data, the type of phenotypic data, and/or the disease with which the phenotypic data can be correlated are applied by pre-processing module 164. For example, active data may be given a higher weight than passive data because active data are generally captured in response to health application 174 directing a user to perform specific activities. Temperature data from client devices 180 may be given a lower weight because individuals other than the user may have access to the thermostat controlling temperature.

In some implementations, some or all of the weights described herein may be applied by analytics 166. The choice of which machine learning features and weights to use for the detection of each disease type is made during the representation learning and classifier training (optimization) steps. These features are automatically identified using general purpose statistical methods such as cross-validation.

Analytics 166 utilize medical and other data from datastore(s) 161 and phenotypic data in order to detect developing diseases, disorders, or disease precursors. To do so, analytics 166 detects digital markers. A digital marker is a feature or combination of features in the user's data that are associated with a disease or disorder and observable in phenotypic data, but may not be considered a full-blown sign of the disease or disorder. For example, the disease or disorder may not produce signs or symptoms typically associated with the disease state or readily observable by a physician in a medical setting. For example, development of neurologic diseases, such as Alzheimer's disease, may result in a change in the pupil size velocity of a user. However, such a change may be too rapid for a physician's human eye to detect or process. Presence of the requisite change in pupil size velocity may be present in the user's phenotypic data and, therefore, may be considered a digital marker of Alzheimer's disease or Dementia.

Alternatively, a developing disease, disorder, or disease precursor may result in a change in walking speed or hand tremors that takes place over time scales longer than an average medical examination. For example, such a change may occur over days, weeks, or months. Such a change may not be observable in a normal medical setting, but may be present in active and/or passive phenotypic data. Thus, such a change may have an associated digital marker in the user's data.

A developing disease, disorder, or disease precursor may also be correlated with how specific physiologic or behavioral expressions change. For example, indicators of some diseases may develop slowly over months and, once a critical period is reached, develop significantly faster into full blown symptoms. Many diseases express a signature dynamic pattern of progression that can be better identified though continuity/increase frequency of measured features. Such a signature may also be used in determining whether the disease or disorder is present or developing. Stated differently, such a signature may be result in a digital marker of the disease in the user's data.

To perform detection of developing diseases, disorders, or disease precursors, analytics 166 may utilize a data model. The data model specifies diseases covered, various decision functions for the phenotypic data used to identify the digital marker(s) for the disease, other features in the phenotypic data corresponding to the developing diseases, disorders, or disease precursors, and disease signatures indicating the probable progression of phenotypic data for each disease. In addition to individual slices of phenotypic data captured at specific times being used in digital marker detection, how the phenotypic data changes over time is also modeled and utilized in determining whether a digital marker exists and to which disease the digital marker corresponds.

In some implementations, the data model compares phenotypic data not only to information for the population, but also to previous medical and phenotypic information for the user. System 150 may also aggregate phenotypic and other data from multiple users (in some implementations after identifying information has been removed) and employ this information in determining whether a digital marker is present in phenotypic data for a user. For example, such information may be used in training analytics 168.

Further, state-of-the-art medical information, analogous to that which a physician can have, can also be used by analytics 166 to determine whether a digital marker exists. For example, such medical information may be used in training analytics 168. Thus, in addition to the phenotypic data for the user, the user's own baseline, the user's own physical condition, and the user's own medical history, other knowledge in the medical or other fields and data related to other individuals may be considered by the model in determining whether the digital marker exists. For example, deviations of at least one or two standards of deviations from the user's baseline may indicate that the digital marker for a disease is present in the user's data.

The decision functions described herein may be input to or discovered by analytics 166. To discover the decision functions, analytics 166 may use medical data, phenotypic data, and other data not only for the user, but for the population (including other users). For example, analytics 166 may use clinical studies, state-of-the-art in knowledge, data aggregated for multiple users of health application 174, and other related data that may reside in datastore 161.

The digital marker is also sufficiently associated with a disease or disorder to warrant intervention. For example, phenotypic data including a single cough detected by microphones on client 170 may be correlated with pneumonia, but the association is not sufficiently close (i.e. not statistically significant) to warrant intervention such as scheduling an examination or x-ray. Analytics 166 do not detect a digital marker for pneumonia in such a case. However, numerous coughs detected by microphones on client 170 that worsen (e.g. in length and/or volume) over several days and/or have a particular characteristic waveform in conjunction with a fever detected by sensors 172 over the same time period may be sufficiently associated to pneumonia or another disease to warrant scheduling a physical examination. Analytics 166 may then detect a digital marker for a respiratory issue.

Similarly, a single mole on the face of a user captured in an image by a camera of sensors 172 of client 170 may not be sufficiently associated with melanoma for analytics 166 to detect a digital marker for melanoma. However, if the phenotypic data indicates that the mole has a statistically significant growth/change in size and/or shape over several weeks, then analytics 166 may detect a digital marker associated with melanoma. Thus, the degree of association between the phenotypic data and the digital marker can become strong enough to change the value of the corresponding skin decision function for analytics 166. In some implementations, the phenotypic data meeting one or more decision conditions is considered to be a statistically significant correlation.

Analytics 166 may determine that although the association between the phenotypic data and disease/disorder is insufficient to detect a digital marker, further tests are warranted. For example, analytics 166 may determine that the phenotypic data does not meet a decision threshold for detection of the digital marker, but does meet other, additional test criteria that are less stringent. In such implementations, additional tests are performed.

In general, such tests are active measures performed via health application 174. For example, passive phenotypic data obtained by sensors 172 over a particular time period such as a month may indicate the possibility of a neurologic condition. Such phenotypic data can include GPS data from client device 170 or 180 that indicates the user's travel patterns have changed such that longer routes, for example at least one or two standards of deviation longer, are taken between the user's home and work place.

If the new pattern triggers a change in the value of the appropriate decision function, based on extracted features such as frequency of occurrence or increase in the length of routes, the user may be prompted to take part in active tests. For example, health application 174 may provide three items for the user to remember via a speaker, wait a specified time (e.g. fifteen minutes), and request that the user repeat the items. Analytics 166 can add this active phenotypic data captured by the microphone (the user's responses) to other phenotypic data in performing additional analysis.

Each type of test is associated with its own set of optimized features, automatically selected by analytics to minimize the appropriate balance between type I and type II errors for each disease type and test recognized by the system. This optimization process occurs in a scalable way, allowing additional disease types and tests to be added. The same ground truth dataset for a given disease can be reused for optimizing different test types, allowing for flexibility in the design and improvement of the best set of tests to use for each type of disease. Analytics may then determine that a sufficient association exists to detect a pre-diseases condition for a neurologic disorder such as Alzheimer's disease or dementia.

Output module 168 may provide recommendations based on the results of analytics 166. For example, output module 168 may provide to health application 174 instructions to obtain active data as described in the neurologic case above. If a digital marker is detected by analytics 166, output module 168 not only provides a detection alert for the associated disease, but may also provide suggestions. For example, scheduling an examination with a physician may be suggested. In some implementations, output module 168 may also provide an analogous pre-disease detection alert to provider systems 190. Further assistance to the user, such as a link to the user's physician's site, can also be provided.

Using system 150, individuals' health can be improved. System 150 can supplement the wellness/disease prevention and disease diagnosis of traditional health care. Sensors 172 on client devices 170, 180, and, in some cases, 182 can capture passive data almost continuously and/or over longer periods of time than a typical medical visit. This passive data can be supplemented with active data. The sensor data captured may also be not readily observable by the unaided human physician. Because the data are captured by sensors, the data are also objective and less subject to interpretation.

Moreover, a significant amount of data may be captured for a user and compared to the user's baseline instead of an average for the population. Using passive and/or active, objective phenotypic data, phenotypic detection platform 160 can detect developing diseases, disorders, or disease precursors. Consequently, accuracy of detection may be improved. Once a digital marker is detected, earlier intervention is possible. Treatment can commence before the corresponding disease or disorder has an opportunity to progress. This early treatment may be less expensive, less disruptive to people's lives, and result in better health outcomes.

In some implementations, system 150 may target diseases for which early intervention and treatment have a significant positive effect on individuals' health. Thus, the capabilities of system 150 may be leveraged to situations in which detection of developing diseases, disorders, or disease precursors optimizes a user's health. As client devices 170 become more ubiquitous, the ability of system 150 to obtain phenotypic data may increase over time. As a result, performance of system 150 can continue to improve.

Thus, the method and system described herein allow for continuous, convenient, contextual, and objective monitoring of physiological and behavioral signs which can lead to more timely disease detection, and timelier diagnoses. By analyzing phenotypic data, the method and system can detect developing diseases before a patient enters the medical setting, advancing the treatment paradigm and avoiding the clinical and financial consequences of late diagnoses.

Example Disease Markers and Detection Mechanisms

Figure 3:
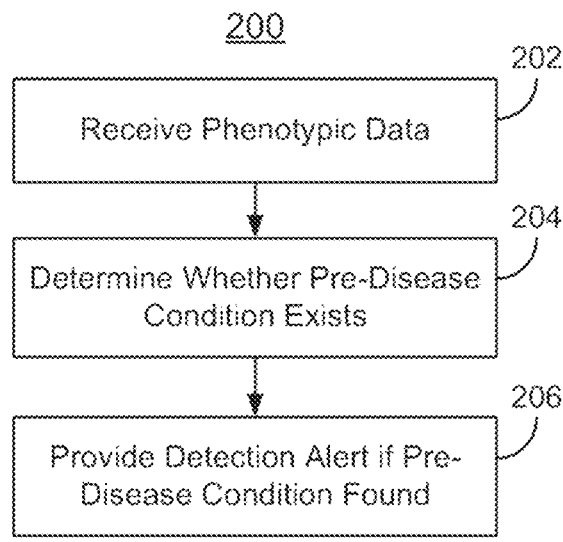
FIG. 3 is a flow chart depicting a method for detecting developing diseases, disorders, or disease precursors using digital phenotypic data, according to some implementations of the present disclosure.

FIG. 3 is a flow chart depicting a method 200 for detecting developing diseases, disorders, or disease precursors using digital phenotypic data. For simplicity, method 200 is described in the context of system 150. However, method 200 may be used in conjunction with other architectures. In addition, the flow of method 200 is described in a particular order. However, other orders are possible and may be performed at disparate times. For example, some steps are performed substantially continuously or over long periods of time, while others are performed at specific times or in response to certain criteria being met.

Phenotypic data from one or more of client devices 170, 180, and 182 are received by phenotypic detection platform 160, at 202. The phenotypic data includes sensor data captured by sensors 172 of one or more of client devices 170, 180 and 182. The phenotypic data may include passive and/or active data from multiple sensors 172 from multiple client devices 170, 180, and 182. For example, audio data from a microphone and position data from a gyroscope on a client device 170, audio data from a microphone and temperature data from a thermostat on client 180, and video data from client 182 can be part of the phenotypic data received at 202.

Reception of data at 202 may take place over long time scales, such as days, week, or months. For example, passive data may be captured by a gyroscope while the user goes about her routine. This data capture may take place continuously or semi-continuously (e.g. only when the user is walking). The corresponding phenotypic data may be streamed to the phenotypic detection platform 160, temporarily stored on client device 170, 180, and/or 182, and sent to phenotypic detection platform 160 in batches, or in another manner.

In some implementations, analytics 166 uses optimized decision functions to determine whether a digital marker exists based on the phenotypic data and medical data from datastore(s) 161, at 204. In some implementations, the user's own medical data and prior phenotypic data are also used. As discussed above, analytics may determine whether a statistically significant association exists between the phenotypic data and markers of diseases. This may take the form of analyzing phenotypic data to investigate whether decision function-based criteria are met, using machine learning, and/or in another manner to define the specific form of the decision functions.

The threshold criterion used for each decision function is optimized to improve its overall performance in terms of false positive (type I) and false negative (type II) errors, e.g. by using ROC curve analysis, or some other combined measure of overall performance. Analytics may determine the optimal threshold for each decision function by using each patient's baseline and ground-truth data, in a scalable way.

As additional ground truth and patient baseline information is collected, these thresholds may be automatically adjusted for each user in a personalized way, in order to optimize the overall performance of the decision function in terms of the balance of type I and type II errors made. For each disease and test type, the appropriate setting for overall performance can be chosen manually at the system level, in order to fulfill the design requirements for each test. For example, there may be two test types for a given disease such as dementia, one for very early warning signs and another for more serious concerns.

The earlier test could be designed for high sensitivity, and its overall performance would be measured to allow a larger number of type I errors compared to the more discriminating test for serious concerns, which may be of lower sensitivity and may only be selected for the analysis after the earlier test predicts that early warning signs exist. Therefore, the overall performance for second test would be set to allow a lower number of type I errors, raising the probability of a type II error being made. In this example, the earlier test is designed for higher sensitivity and lower specificity, to minimize the number of false negative (type II) errors, and the later test is designed for lower sensitivity but higher specificity, to minimize the number of false positive (type I) errors.

The overall performance measures for each test is set to the appropriate value to meet these design requirements. Analytics automatically adjust the thresholds used by the corresponding decision functions for these tests for each user in a personalized way, relative to their individual baselines. As additional baseline and ground truth data are made available, analytics automatically re-optimize these thresholds in a scalable way, providing maximum overall performance of detection for each user compared to conventional systems.

If it is determined that the digital marker exists, then a detection alert for the disease corresponding to the digital marker is provided via output 168, at 206. Thus, the detection alert is sent from phenotypic detection platform 160 to health application 174, which presents the detection alert to users. For example, a graphic can be rendered on the display (not shown in FIG. 2) of client device 170 and an alert sound provided via speakers. The identity of the disease and/or digital marker may also be provided from phenotypic detection platform 160 to client device 170.

Finally, advice such as to contact a physician for an examination, may be provided to client 170, which presents the advice to the user. In addition, appropriate action may be facilitated. For example, a link to the physician's office or to articles regarding the disease may be sent to client 170 and displayed to the user. At 206, alerts and other information may be sent not only to client device 170 but also to client devices 180 and/or 182.

Using method 200, passive and active phenotypic data can be used to determine whether a digital marker is present in phenotypic data for a user. Once a digital marker is detected, earlier intervention is possible. Consequently, treatment can be started earlier, before the corresponding disease or disorder has an opportunity to progress. This early treatment may be less expensive, less disruptive to individuals' lives, and result in better outcomes. Individuals' health may be improved.

Cholesterol

For example, in addition to being expressed in the blood and measured via lipid panels, cholesterol can result in a ring around an individual's iris. Analytics 168 can be trained to recognize such a ring in an image of the user's eye. Using images of individuals' eyes having cholesterol levels determined using conventional lipid panels, analytics 168 can also be trained to map features of a ring around a user's pupil to the corresponding molecular measure—e.g. the cholesterol level in a lipid panel.

In some implementations, a user captures an image of the eye, for example as described herein with respect to pupil velocity. The image is provided to platform 160 at 202 in method 200. The image can be analyzed for the presence and characteristics of such a ring (e.g. continuity and size), at 204. For example, the existence of a ring and features of the ring correspond to the pupillary feature discussed herein, and these features could be tracked overtime using the systems and methods disclosed herein to determine a cholesterol trend.

The characteristics of such a ring can be mapped to a cholesterol level in a lipid panel. In some implementations, the cholesterol level can be considered the digital marker described herein, and corresponds to the health status. In some implementations, the digital marker (cholesterol level to which the ring characteristics are mapped) can be presented to the user, at 206. In addition, based on the digital marker, recommendations can be made. For example, if the user's digital marker indicates that the user's cholesterol level is above a decision threshold, the user can be suggested to obtain a lipid panel and/or schedule a physical examination. As such, a user is better able to track and maintain a healthy cholesterol level and intervene earlier in the event of digital marker(s) for a high cholesterol level.

Figure 4:
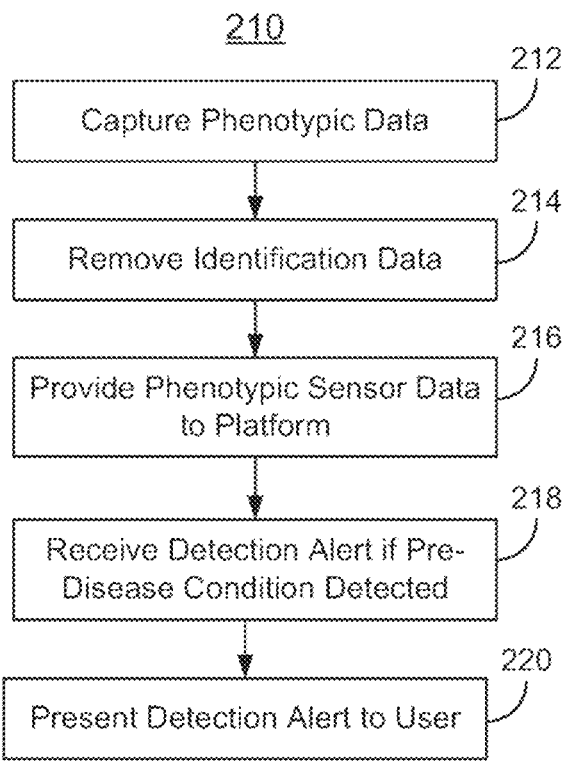
FIG. 4 is a flow chart depicting a method for measuring digital phenotypic data, according to some implementations of the present disclosure.

FIG. 4 is a flow chart depicting a method 210 for detecting developing diseases, disorders, or disease precursors using digital phenotypic data and/or pupillary features. For simplicity, method 210 is described in the context of system 150. However, method 210 may be used in conjunction with other architectures. In addition, the flow of method 210 is described in a particular order. However, other orders are possible and may be performed at disparate times. For example, some steps are performed substantially continuously or over long periods of time, while others are performed at specific times or in response to certain criteria being met.

Sensor data are captured using one or more sensor(s) 172 on client device 170, at 212. At 212, sensor and/or other data may also be captured via client devices 180 and 182. The sensor data captured may be passive or active, as described herein. If the data capture is passive, then 212 may take place over the course of hours, days or months. For example, passive data may be captured daily for multiple hours over the course of days, weeks, or months (e.g. up to six months or more). If active data are captured, health application 174 may lead the user through process(es) used in capturing data.

Capturing Iris Deposits

The present disclosure further provides for capturing iris deposits. An example methodology first provides for iris recognition. For example, iris recognition includes automatic detection of pixel-based eye and tip-of-nose locations (e.g., FIG. 8). This automatic detection of reference locations ensures trigonometric and spatial consistency of measurements. In some implementations, the alignment is moderately-facilitated by a user, with machine-algorithmic assistance (e.g., providing prompts to the user to re-orient the camera).

The example method then provides for segmentation, which includes first demarcating a region of interest (ROI) (e.g., separating inner iris pixels from the limbus, or the outer-boundary iris). Segmentation then includes determining threshold iris circle parameters, such as a radius and center coordinates. Segmentation then includes determining threshold pupil circle parameters, such as a radius and center coordinates. In some implementations, a Hough Transform is used.

For example, this segmentation (localization) process serves to search for the center coordinates and radius of the pupil/iris. In some implementations, these coordinates are marked ci, cp where ci is represented as the parameters [xc, yc, r] of the limbic and iris boundary, cp is represented as the parameters [xc, yc, r] of the pupil boundary. An example method for selecting the center coordinates consists of selecting threshold coordinates and then checking if additional selected points (near the threshold points) correspond to a local minimum in their immediate neighborhood; if so, these points serve as the possible center coordinates for the iris. In some implementations, $r_{min}$ and $r_{max}$ of the iris are set manually, or selected from a database. Therefore, this method provides the value of ci and cp which is the value of [xc, yc, r] for the pupillary and limbic/iris boundaries and the segmented image. As discussed above, this process uses The Hough Transform.

The method then provides for normalizing the image data, to identify an incidence of Arcus Senilis (iris cholesterol deposit). For example, the deposit appears as a yellow-white ring around the cornea, occurring from the limbus up to 30% through iris towards the pupil. For example, the ring around the cornea is separated from the limbus by a clear zone, which is typically 0.3 to 1 mm in width. The normalized image, for example is cropped to retain only the region of interest. For example, the image is cropped based on iris radius value, so the unwanted area is removed (e.g. sclera and limbic). Because the area of the ring occurs from the sclera/iris up to 20-30% toward to pupil, this is the only the area that must be analyzed.

The method then provides for a quantitative assessment of the ring to determine a severity of the disease state. In some implementations, to determine whether the eye has the ring, an image histogram is plotted. An example algorithm assumes the image contains two classes of pixels (e.g. foreground and background) and finds the optimum threshold separating the two classes so that their combined spread (within-class variance) is minimal. In some examples, these features could be tracked overtime using the systems and methods disclosed herein to determine a trend and therefore a progression of the disease state.

Sclera Vasculature

Figure 29:
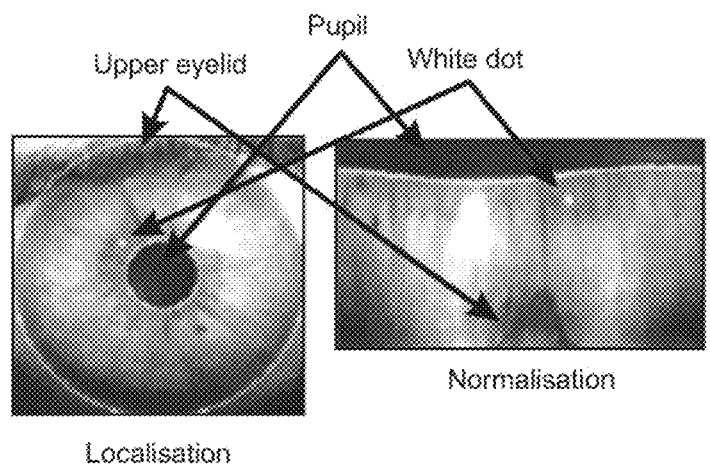
FIG. 29 depicts example iris recognition, according to some implementations of the present disclosure.

The present disclosure further provides for identifying sclera vasculature. An example method includes first providing iris recognition. Iris recognition can be as discussed herein with respect to the method for capturing iris deposits. For example, FIG. 29 depicts example identifications of the upper eyelid, the pupil, and a white dot, according to some implementations of the present disclosure.

Figure 30:
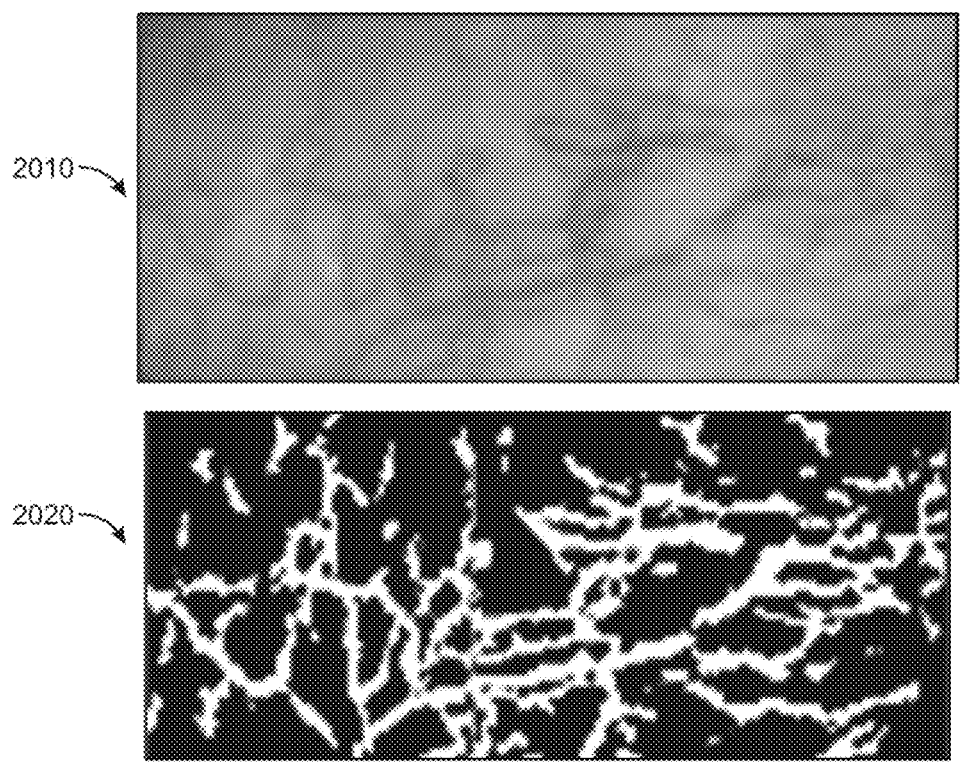
FIG. 30 depicts example normalization data when identifying sclera, according to some implementations of the present disclosure.

The example method then provides for segmentation, which includes a rectangular demarcation of the sclera area from the iris. For example, sclera, skin, and a reference color (e.g., white patch) pixel coordinates are identified in an image viewer. Segmentation then includes classifying pixels into foreground (e.g., blood vessel) and background (e.g., white sclera). Segmentation then includes normalizing the iris from a circular approximation to a rectangular approximation. In some implementations, segmentation includes color balancing, where RGB color indexes are produced for sclera, skin and reference color. In some implementations, a binary image is produced with a block background and white veins. For example, 2020 of FIG. 30 depicts the binary image while 2010 shows the original, non-binary image.

In some implementations, the method further provides for remapping all points within the iris region to a pair of polar intervals [0,1], rescaled depending to the angle around the pupil and iris. The method further provides for color identification and analysis using sclera and skin pixel coordinates (for comparison). A reference color, manually identified in an image viewer, is represented by a white patch in the color chart. Three indexes, Red (R), Green (G) and Blue (B), are calculated by averaging 900 neighboring pixels (30×30 region) centered on pre-defined pixel coordinates. These color indexes result: $R_{eye}$, $G_{eye}$ and $B_{eye}$ for sclera, $R_{skin}$, $G_{skin}$ and $B_{skin}$ for skin, and $R_{ref}$, $G_{ref}$ and $B_{ref}$ for reference color. Normalized color indexes are also calculated for sclera and skin (e.g., $R_{eye,nor}=R_{eye}/R_{ref}$ is the normalized sclera red color index. In some implementations, the variation in measures relative to a retrospectively established longitudinal baseline is calculated in order to indicate a disease state or provide a performance measure for the disease.

Measuring and Determining Pupillary Features

For example, the pupillary light reflex may be measured to determine pupil size velocity as a reflex response to a stimulus such as light. To do so, health application 174 renders a template having alignment marks for the user's key facial parts on the display for client device 170. Health application 174 instructs the user to align key facial parts with alignment marks represented on a smart phone screen. The user's facial parts are selected for alignment to ensure trigonometric consistency in depth and angle given these facial parts remain fixed over time in three dimensional space and cannot be voluntarily or involuntarily changed by the user.

Client device 170 may provide an indicator, such as a green light, when the measurement is about to be taken. Health application 174 flashes a light on client device 170 and captures a video of the user's eye with a high definition camera that is one of sensors 172. Using the video, health application 174 determines the pupil diameter reflex velocity—the speed at which the pupil diameter of the user's eye contracts in response to the light and subsequently dilates back to its normal baseline size. Thus, active phenotypic data for the pupil velocity is captured at 212.

The pupil velocity may be used to determine whether developing diseases, disorders, or disease precursors for certain neurologic disorders exist. In addition, other phenotypic data may be captured because of the use of the camera. For example, the color of the sclera of the eye is visible. The color of the eye sclera may be used to determine whether various developing diseases, disorders, or disease precursors are present in the user. The eye sclera having a yellow color may be indicative of jaundice. Redness color of the eye sclera may indicate cardiovascular issues due to constriction of blood vessels in the eye. Similarly, redness of the sclera considered in the context of frequency and time of day may be indicative of substance abuse.

Other phenotypic features in the ring around the pupil of the eye may be indicative of cholesterol deposits typically associated with cardiovascular issues. Changes in pigmentation or growth of moles on the user's face may be indicative of dermatologic conditions such as melanoma. Thus, a single active test can generate data as quantified measures of multiple phenotypic features related to multiple diseases.

Identification information is optionally removed from the sensor data at 214. Stated differently, features of interest for phenotypic data may be extracted from the data. In the example above, pupil velocity (e.g. magnitude and direction), sclera color, a measure of tissue inflammation, and/or other characteristics may be represented as scalar numbers or using another mechanism after extracting relevant metrics from the underlying raw data. However, the image of the user that may be identifiable is not utilized. The remaining data in the absence of the identifying information is included in the phenotypic data that is sent to phenotypic detection platform 160, at 216. Analytics 166 uses the phenotypic data to determine whether a digital marker exists in the user's data.

If a digital marker is detected, then an alert is provided from phenotypic detection platform 160. Thus, the pre-disease detection alert is received by client device 170, at 218. The alert is then presented to the user of the client, at 220. For example, the alert may be rendered on a display of client device 170, 180, or, 182. In some implementations, an audio alert can supplement or replace the graphical alert. The user is thus made aware of developing diseases, disorders, or disease precursors and can take further action. Other information described herein, such as a suggestion to contact a physician for a physical examination, may also be received at 218 and presented to the user at 220.

Using method 210 user's health may be improved. Sensors 172 on client devices 170 and sensors on client devices 180 and 182 can capture passive data almost continuously and/or over longer periods of time than a typical medical visit. These passive data can be supplemented with active data. Using passive and/or active, objective phenotypic data, phenotypic detection platform 160 can detect developing diseases, disorders, or disease precursors. Once a digital marker is detected, earlier intervention is possible. This early treatment may be less expensive, more successful, and less disruptive to people's lives. As client devices 170 and 180 become more ubiquitous, the ability of method 210 to obtain and utilize phenotypic data over time increases. As a result, performance of method 210 can further improve through a self-improving feedback loop.

Figure 5:
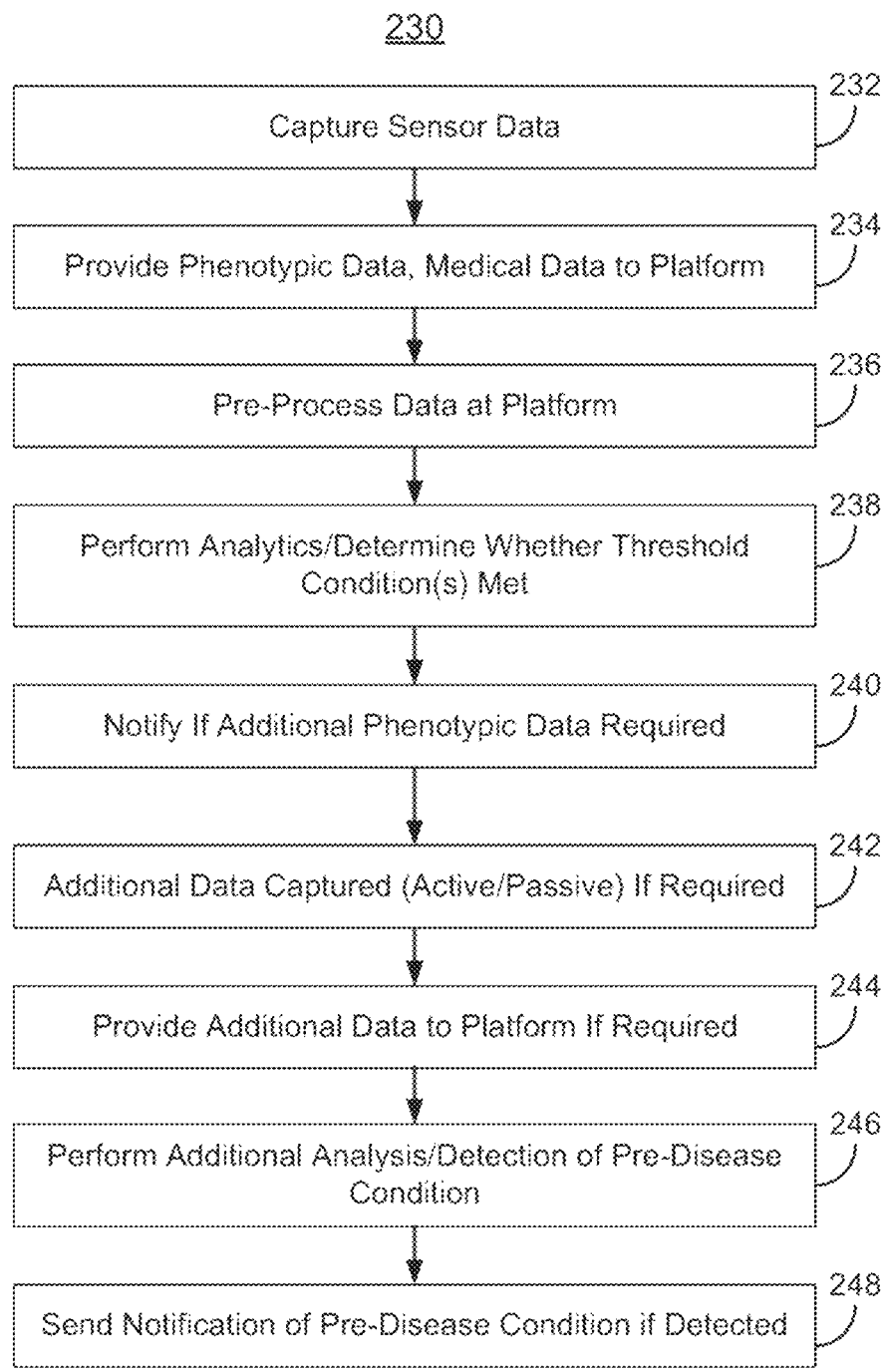
FIG. 5 is a flow chart depicting a method for detecting developing diseases, disorders, or disease precursors using digital phenotypic data, according to some implementations of the present disclosure.

FIG. 5 is a flow chart depicting a method 230 for detecting developing diseases, disorders, or disease precursors using digital phenotypic data. For simplicity, method 230 is described in the context of system 150. However, method 230 may be used in conjunction with other architectures. In addition, the flow of method 230 is described in a particular order. However, other orders are possible and may be performed at disparate times. For example, some steps are performed substantially continuously or over long periods of time, while others are performed at specific times or in response to certain criteria being met.

Sensor data are captured using one or more sensor(s) 172 on client device 170, at 232. The sensor data captured may be passive and/or active. The data capture may take place over the course of hours, days, or months. Consequently, 232 is analogous to 212, described herein.

Phenotypic data, including data captured by the sensors (e.g., image data indicative of pupillary features), is sent to phenotypic detection platform 160, at 234. In some implementations, additional medical data for the user is provided to phenotypic detection platform 150 at 234. For example, the user's medical history or updates from a recent physical exam, at-home health related devices such as glucose monitors, consumer related tests such as genetics tests, or molecular test that can be conducted at home or in a medical or commercial setting may be provided to phenotypic detection platform 160 from client device 170, provider system(s) 190 or from another source. Molecular tests may include those performed within a healthcare setting or without, including tests performed for non-diagnostic purposes.

The phenotypic data are optionally pre-processed by pre-processing module 164, at 236. In some implementations, pre-processing phenotypic data, medical data, or other data can be used to create a digital biomarker, as discussed above. For example, weights may be applied based on the sensor capturing the data or the disease/disorder for which the data are used. Analytics 166 use the phenotypic data in conjunction with other data such as medical data or the user's prior medical data to determine whether one or more developing diseases, disorders, or disease precursors exist, at 238. In some implementations, it is determined whether threshold conditions are met.

In some cases, analytics 166 does not determine that a digital marker is present. However, the phenotypic data are sufficiently correlated with a disease or disorder that further action is taken. For example, it may be determined at 238 that decision conditions for further active tests are met. If the decision conditions for further testing are met, then client devices 170, 180, and/or 182 are notified that additional phenotypic data are required, at 240. This notification may include phenotypic detection platform 160 sending a command to client device(s) 170, 180, and/or 182 to perform additional active tests, to take passive data more frequently or for longer time intervals, and/or to perform active tests more frequently. Such additional phenotypic data are captured at 244. In some implementations, capture of other data as in 232 also continues. The resulting phenotypic data may have identifying information removed and features extracted, as in 214, and is provided to phenotypic detection platform 160, at 244.

Additional analysis is performed using data provided at 244, data previously provided, medical data, and clinical data, at 246. Thus, analytics 166 determine whether a digital marker exists based on the phenotypic data, at 246. If it is determined that the digital marker exists, then a detection alert for the disease corresponding to the digital marker is provided via output 168, at 248. Thus, the detection alert may be sent from phenotypic detection platform 160 to health application 174, which presents the detection alert to users. Other information may also be provided at 248. For example, the identity or description of the disease and/or digital marker, advice such as to connect with a physician for a physical examination, or links to the physician's office or to articles regarding the disease may be sent to client 170 and presented to the user.

Using method 230, passive and active phenotypic data can be used to determine whether a digital marker is present in data for a user. Once a digital marker is detected, earlier intervention is possible. Consequently, treatment can be started earlier, before the corresponding disease or disorder has an opportunity to progress. This early treatment may be less expensive, less disruptive to people's lives, and result in better outcomes. Users' health may be improved.

The following are examples in which method 200, 210, and/or 230 may be utilized to detect developing diseases, disorders, or disease precursors for Alzheimer's disease, sleep apnea, Parkinson's disease, generalized anxiety disorder and pneumonia using particular sensors 172 and measures. Other methods and systems may be used to detect developing diseases, disorders, or disease precursors for such diseases in other implementations. Further, developing diseases, disorders, or disease precursors for other diseases and/or disorders may be detected using the method and system described herein. For simplicity, detection of the diseases and disorders below are described in the context of method 230.

For Alzheimer's disease, passive and active sensor data are captured at 232. Passive data includes gyroscopic data captured while the user walks, for example using a gyroscope on a smart watch. Active data are also captured at 232 using a microphone and the camera. Using the microphone, the user's responses to a cognitive test are recorded. For example, heath application 174 can administer a test similar in nature and purpose to Wechsler Memory Scale, such as subtest I (recall) and record the user's responses on a microphone. This test may be administered periodically, such as once a week, once every two weeks, or once per month. During phone calls, the user speaking into the microphone can be part of the phenotypic data collected by the microphone.

The temporal patterns in the user's spontaneous speech, such as speech tempo, number of pauses in speech, and the pause length, may be extracted as part of 232. Thus, the substance or content of the user's conversation is not stored. As discussed above, the pupil size velocity can also be captured using the camera of client device 170 at 232. In addition to velocity, the magnitude of the change in pupil sizes may also be collected at 232. This measure of pupil velocity may also be carried out periodically, such as once a week, once every two weeks, or once per month.

The phenotypic data collected at 232 are provided to phenotypic detection platform 160. Pre-processing of the phenotypic data may then be performed at 236. For example, a higher weight is given to the active data collected by the microphone and camera (corresponding to the cognitive test for the Weshsler Memory Scale and to the pupil velocity, respectively). A lower weight is given to the gyroscopic data. For example, a weight of 1 may be applied to the pupil velocity and cognitive test, a weight of 0.5 may be applied for pupil size velocity, while a weight of 0.3 may be applied to the gyroscope data.

Analytics are performed at 238. For example, the threshold for the average speed (in m/s) for the user over ten meter increments from the gyroscope phenotypic data is 1.21 m/s. If the user's speed averages not more than 1.21 m/s then this feature in the user's phenotypic data is considered a digital marker for Alzheimer's disease. User input may be provided to ensure that a decrease in walking speed is not the result of other factors (such as injury or fatigue) by alerting the user of this drop in speed and requesting input as to the reason (if the user is aware of any) and if necessary providing the user with an adaptive symptom checker with probability weighted values associated with each answer to increase statistical confidence of the resulting analytics. The threshold for the user's score on the cognitive test (for subtest I-recall) in the Weshsler Memory Scale is 15.9. If the user's score on this test is not more than 15.9 on multiple occasions, then this phenotypic data includes a digital marker indicative of Alzheimer's disease.

For pupil size velocity, if a trend toward a smaller amplitude in the change in pupil size and a statistically significant lower maximum pupil velocity is observed, the pupil size velocity phenotypic data exhibits a digital marker that indicates Alzheimer's disease or Dementia. Although each of the above results is described as a digital marker for Alzheimer's disease, in some implementations, it is a combination including the requisite speed, scores and/or velocity measurements that is together considered to be the digital marker for Alzheimer's disease.

In some implementations, analytics may take into account the user's medical history. For example, the thresholds, or decision conditions, may be changed or the weights may be increased to make detection of a digital marker more likely if the user's family history includes Alzheimer's disease. If some combination of these thresholds and trends are met, then either additional data capture may be triggered at 246 or the digital marker for Alzheimer's disease detected at 248. The user may then be directed to consult a physician.

Similarly, developing diseases, disorders, or disease precursors for sleep apnea may be detected using method 230. During sleeping, a person's oxygen saturation level ($SpO_2$) may be passively measured using a PPG sensor on client device 170 such as a smart watch, snoring may be passively monitored using a microphone on client device 170 such as a smart phone, and, in some implementations, ECG readings can be passively obtained using a smart watch. Although described as passive monitoring because the user is not being instructed to perform specific tasks, these data may also be considered active data because the monitoring may commence only in response to a user desiring to test for sleep apnea. These data are captured at 232 and provided to phenotypic detection platform 160.

Pre-processing at 236 may include providing a weight to the data. In such a case, the weights may be: 0.5 for the PPG data, 0.5 for the microphone data, and 0.2 for the ECG data. Analytics 166 process the data and determine whether a digital marker exists and/or more data are required at 238 and 246. For example, if the oxygen saturation level is less than ninety percent during sleeping, particularly if this occurs at least fifteen times and for at least three minutes or longer during sleeping, this phenotypic data indicates that the user suffers from sleep apnea. A snoring intensity of at least 47.4 dB (a possible threshold for sleep apnea) indicates that the digital marker for sleep apnea is detected at 238 or 246.

In addition, a mean apnea-hypopnea index (AHI) can be determined by analytics 166 based on the phenotypic snoring data. ECG readings indicative of sleep apnea, such as a shift in the electrical axis, may also be used by analytics 166 to detect the digital marker for sleep apnea. Although described in the context of each of the above data (oxygen saturation, showing intensity, mean AHI) detecting a digital marker for sleep apnea, in some implementations, it is a combination of one or more of these features that is used in detecting the digital marker for sleep apnea. If the threshold criteria above are met, then phenotypic detection platform 160 indicates that the user's data includes the digital marker for sleep apnea. The user may also be directed to undergo a sleep study in a medical environment.

The digital marker for Parkinson's disease may also be detected using method 230. For example, phenotypic data may be collected at 232 using a gyroscope. Health application 176 can direct a user to walk a particular distance unaided, with a cane and with a roller walker. In such an implementation, the data collected are active data. The gyroscope, for example on a smart watch, may be used to determine whether the user is walking unaided, with a cane, or with a roller walker based on the user's hand position. The test may be repeated periodically, such as once per week, once every two weeks, and/or once per month. During such tests, phenotypic data may also be collected using an accelerometer to determine the number of steps per minute a user takes. Thus, the cadence of the user's walk may be measured.

The phenotypic data are provided to phenotypic detection platform 160 at 234 and, if required, 244. At 236 the data are pre-processed and may be weighted. For example, gyroscopic data for walking speed may be accorded a weight of 1 while accelerometer data for cadence may be given a weight of 0.5. A threshold for the reduction in walking speed of ten percent when using a cane and fifteen percent when using a roller walker can be used by analytics 166 at 238 and 246. Thus, if it is determined at 238 and 246 that the user's walking speed decreased by at least ten percent when using a cane and/or at least fifteen percent when using a roller walker, the walking speed data indicates that the digital marker for Parkinson's disease is present.

In some implementations, analytics 166 may also utilize an overall decrease in walking speed over time as further indication of Parkinson's disease. Similarly, a threshold for the reduction in steps per minute of ten percent when using a cane and five percent when using a roller walker can be used by analytics 166 at 238 and 246. Thus, if it is determined at 238 and 246 that the user's cadence decreased by at least ten percent when using a cane and/or at least five percent when using a roller walker, the cadence indicates that the digital marker for Parkinson's disease is present. Analytics 166 may also utilize an overall decrease in the cadence (steps per minute) over time as further indication of Parkinson's disease. Thus, the walking speed and/or cadence, optionally in conjunction with other data, may be used to detect the digital biomarker for Parkinson's disease.

In some implementations, body tremors detected with a gyroscope and finger tapping speed as captured by a camera may also be detected at 232/242 and used by analytics 166. Health application 160 can instruct users to tap the index finger against the thumb as big and as fast as possible. Finger taps that are in smaller amplitude (hypokinesia) and lower in frequency (bradykinesia) may be used by analytics as an indicator for the presence of a digital marker for Parkinson's disease. Similarly, freezing of the gait, as measured by a gyroscope, that increases over time can be considered in 238 and 246 to be indicative of Parkinson's disease.

In some implementations, voice patterns can also be captured by a microphone at 232 and potentially used as part of the analysis for Parkinson's disease at 238 and 242. Using the data described herein, it can be digital marker(s) for Parkinson's disease may be detected in the user's data. In response to a detection of a digital marker of Parkinson's disease at 248, a user can be directed to consult a physician.

The digital marker for generalized anxiety disorder can also be detected using method 230. Heart rate and ECG can be passively monitored using PPG and ECG sensors. Microphones can be used at 232 to monitor changes in speech and tone. Usage of client device 170 that is a smart phone can also be detected at 232. For example, the amount of time the touch screen is active (as opposed to locked) during a day may be passively monitored.

An increase of ten points to the heart rate can be determined at 238 and 246 to be an indicator of stress and/or generalized anxiety disorder. Similarly, an increased frequency of T-wave inversion for the ECG is associated with depressive symptoms, while a reduced frequency of T-wave inversion is associated with anxiety. Also as part of the ECG data, a decreased QT interval from the user's baseline is an indicator of anxiety or stress.

Similarly, changes in vocal tone and speech as well as increased smartphone use may be utilized by analytics 166 to determine whether the digital marker for generalized anxiety disorder is present. In response to a detection of the digital marker for generalized anxiety disorder, for example in response to a combination of a daily increase in heart rate of at least ten points, increased time using the smartphone, and reduced T-wave inversions as compared to the user's baseline, analytics 166 determine at 246 that the user suffers from generalized anxiety disorder.

The digital marker for pneumonia can also be detected using method 230. A person's oxygen saturation level and heart rate may be passively measured using a PPG sensor on client device 170 such as a smart watch. The smart watch may also passively monitor heart rate. Coughing and/or wheezing may be passively monitored using a microphone on client device 170 such as a smart phone. In some implementations, temperature may be monitored by client device, input by the user after the user checks their temperature using a thermometer, or electronically communicated by a smart thermometer. The temperature data may thus be data from a health-related device (thermometer). These data are captured at 232 and provided to phenotypic detection platform 160.

Pre-processing at 236 may include providing a weight to the data. In such a case, the weights may (for example) be as follows: 0.5 each for the oxygen saturation and heart rate data, 1.0 for the temperature data and 0.2 for the microphone data. Analytics 166 process the data and determine whether a digital marker exists and/or more data are required at 238 and 246. For example, if the average oxygen saturation level is less than ninety-four percent and is at least three percent lower than a baseline over forty-eight hours, then this phenotypic data are determined at 246 to indicate a digital marker for pneumonia.

In some implementations, a temperature of greater than one hundred degrees Fahrenheit and a heart rate greater than one hundred beats per minute over the same time period are also determined at 238 and 246 to be indicators of pneumonia. In the absence of asthma, crackles and decreased breath sounds, if detectable by the microphone and a sufficient signal-to-noise ratio is present, can also be used by analytics 166 to indicate that pneumonia is present. However, cough frequency, intensity, and/or characteristic wave form may be preferred to be used instead.

Analytics automatically selects the optimal features to use for each disease type and test according to the overall performance measure set for that test in terms of the appropriate balance between type I and type II errors specified in the design requirements for each test. In some implementations, the extracted features may include learned features using a representation learning method such as deep learning.

In some implementations, the extracted features may include manually specified statistical measures such as the average value over an interval, a standard deviation, a measured slope of a curve, etc. The system allows for a plurality of features to be specified as inputs for analytics by combining the same set of statistical measures with different sets of parameters such as the length of a sliding time window, the type of filter or transformation to apply such as finite differencing, discrete Fourier transform, and median filtering, and all possible combinations thereof. This allows for thousands of features to be tested for each sensor or data type, resulting in hundreds of thousands of total features to be selected from.

For each disease and test type, the feature selection process globally optimizes all of the feature extraction parameters in order to achieve the best overall performance of that test for a given measure of performance in terms of type I and type II errors in a scalable way, relative to each user's individual baseline information, resulting in a set of decision functions with thresholds optimized to maximize the overall performance of the detection of each disease for each user in a personalized manner.

If some combination of the criteria above is met, then phenotypic detection platform 160 indicates that the user's data exhibits the digital marker for pneumonia. The user may also be directed to seek treatment immediately. Thus, developing diseases, disorders, or disease precursors for the above and other diseases may be detected using methods 200, 210, and 230. Consequently, individuals' outcomes may be improved.

Figure 6:
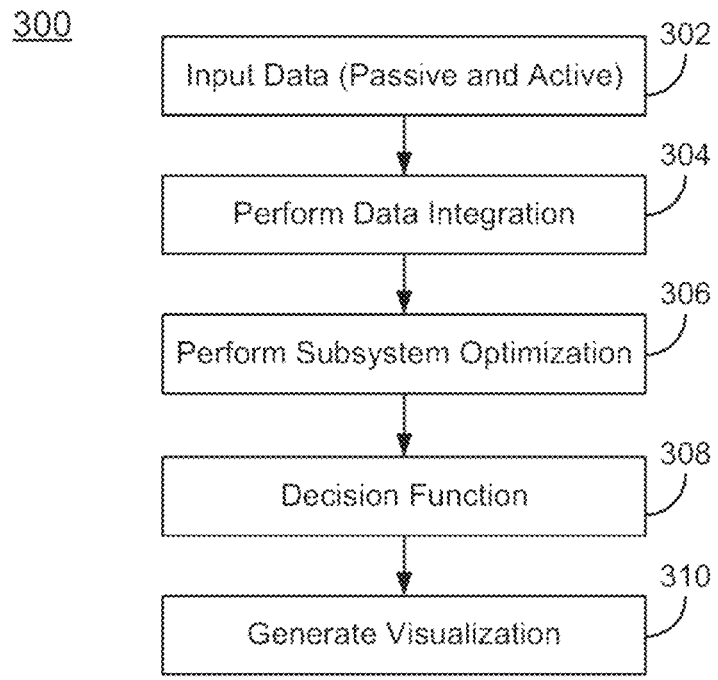
FIG. 6 is a diagram depicting a method for using computational architecture for a system for detecting developing diseases, disorders, or disease precursors using digital phenotypic data, according to some implementations of the present disclosure.

FIG. 6 is a flow chart depicting a computational architecture flow 300 of a system for detecting developing diseases, disorders, or disease precursors using digital phenotypic data. An analogous pipeline would be provided for each user. However, the specifics of such a pipeline may differ in other implementations.

Data are input at 302. The data includes phenotypic data. Passive and/or active data may be provided. The input data be formatted and integrated, at 304. This operation standardizes each user's dataset and converts the dataset into a format appropriate for analysis with statistical and machine learning algorithms. Subsystem optimization is performed, at 306. Subsystem optimization is described herein in FIG. 7. The result of the subsystem optimization can represent the results of all tests for all disease types in each pathophysiological category. These results may vary in terms of their precise content, depending on which tests have been selected to run for this user. A decision function is applied at 308 and visualizations associated with results for display are provided, at 310.

Figure 7:
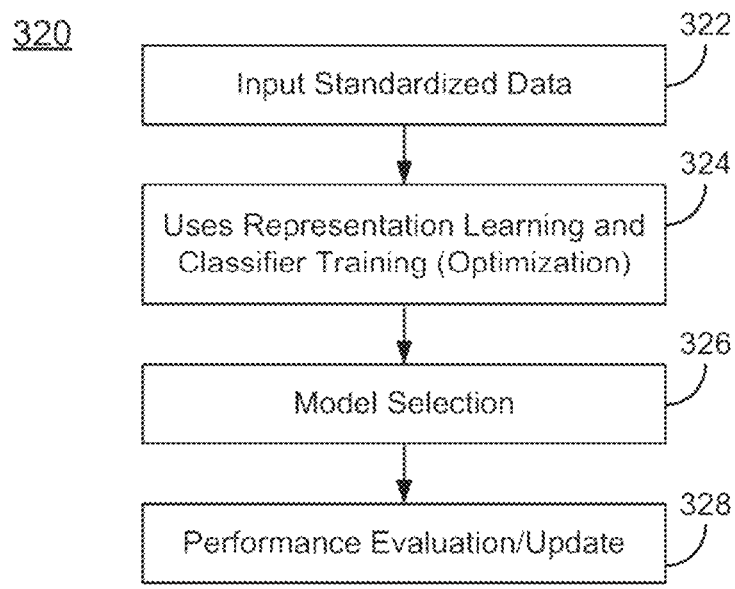
FIG. 7 is a diagram depicting a method for performing subsystem optimization for a system for detecting developing diseases, disorders, or disease precursors using digital phenotypic data, according to some implementations of the present disclosure.

FIG. 7 is a diagram depicting a method for performing subsystem optimization in a system for detecting developing diseases, disorders, or disease precursors using digital phenotypic data. Thus, FIG. 7 depicts an example implementation of method 320 for performing subsystem optimization at 306.

Standardized data output after data integration (at 304) is input, provided 322. Representation learning and classifier training is applied, at 324. Thus, statistical training and/or model fitting is performed. The feature extraction and classifier parameters are optimized for maximum overall performance on each test, using ground-truth training information. In some implementations, 324 is optimized for maximum overall performance on each test, using ground-truth training information.

In addition, 324 may be iterated over all disease types and tests selected for this user, applying the same optimization algorithm each time. Based on these results, the trained models are compared and a determination is made as to which model to use for each test (i.e. model selection), at 326. The models that are selected can be evaluated and updated automatically as additional user baseline and ground truth data are collected, at 328. In addition, the decision functions for each selected model are tuned to set their thresholds relative to the overall performance requirements set at a system level for each test, in order to balance their type I and type II error rates.

For example, consider the case of detecting one respiratory and two neurological diseases, using two tests for each disease, for a total of six tests. Suppose the data were acquired over a six-week time period, with one week of missing passive respiratory data and two weeks of missing active neurological data. The data are integrated at 304. Thus, the data are processed and a set of summary statistics that are not sensitive to the missing information are derived. The data are ready to send to the statistical analysis subroutine at 306. This "subsystem optimization" process can run the same sequence of procedures on this integrated data set as many times as there are tests, in this case six.

All of the processes described herein for "subsystem optimization" are performed for each of these six tests. In this example, the models for two respiratory and four neurological tests each go through the same fitting and evaluation process. Next, a decision function would be created for this user, at 308. The decision function can be used to notify the user if a digital marker for a health issue has been detected, by integrating the set of models output during the subsystem optimization step. From this output, a visualization can be generated at 310 in order to convey the results of the analysis and decision function output.

System for Measuring Pupil Metrics

Figure 13:
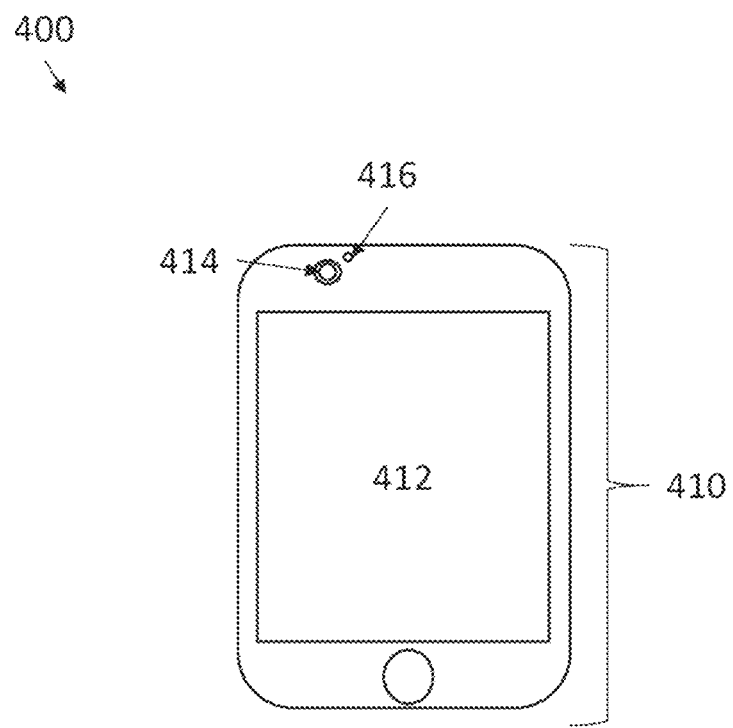
FIG. 13 depicts a system for measuring pupillary response, according to some implementations of the present disclosure.

FIG. 13 provides depicts a system 400 for measuring pupillary response, according to some implementations of the present disclosure. In some examples, system 400 is a smart phone, a smart watch, a tablet, a computing device, head gear, head set, virtual reality device, augmented reality device, or any other device capable of receiving and interpreting a physical signal. System 400 includes a housing 410, a display 412, a camera 414, a speaker 418, a vibration motor 420, and a sensor 416. Alternative or in addition to the sensor 416, the system 400 can include a distance detector. Examples of distance detectors are described in U.S. Pat. No. 8,150,142, which is hereby incorporated by reference herein in its entirety.

FIG. 13 shows a front side of the system 400. The system may also include a camera (e.g., the same as, or similar to, the camera 414) on the back side of the housing 410. The housing 410 provides a case for the display 412, the camera 414, the speaker 418, the vibration motor 420, and the sensor 416. The housing 410 further includes any computing components (not shown) of the system 400, including, for example, a processor, a memory, a wireless communication element, and any other elements as readily contemplated by one skilled in the art. The computing components further include any software configured to complete any of the processes discussed further herein.

The housing 410 includes a front and a back. The camera 414 is located on the front of the housing 410. In some implementations, the sensor 116 is a distance detector including an emitter and a receiver. The distance detector is also located on the front of the housing 410. In some implementations, a first field of view of the camera 414 is similar to a second field of view of the distance detector.

In some implementations, the receiver of the distance detector includes an image capture assembly. In some implementations, the camera 414 includes the receiver of the distance detector. In some implementations, the camera 414 includes the distance detector. In some implementations, a mobile device includes the camera 414 and the distance detector.

In some implementations, the emitter of the distance detector includes a visible light emitter. In some implementations, the emitter of the distance detector includes a light source configured to transilluminate a transparency with optical radiation to project an uncorrelated pattern of spots onto the at least one eye of the user, the transparency containing the uncorrelated pattern of spots.

The display 412 is, for example, the screen of a smartphone, a smart watch, an optical headset, or any other device. In some implementations, the display 412 is an LCD screen, an OLED screen, an LED screen, or any other type of electronic display, as known in the art, which shows images, text, or other types of graphical display. For example, the screen provides a plurality of light-emitting diodes or other means for generating a plurality of pixels. Each pixel displays a light stimulus.

In some implementations, the display 412 is configured to emit visual light. In some implementations, the display 412 emits light on a portion of a surface area of the display 412; in other implementations, the display 412 emits light on all of a surface area of the display 412. The light emitted by the display 412 can be controlled to automatically emit light, and increase or decrease the visible stimulus. In some implementations, the display 412 shows image data captured by the camera 414. The display 412 can also display text and messages to a user. In some implementations, the display 412 may display a live feed of image data output from the camera 414. In some examples, the display 412 may provide a mental stimulus to the user in the form of a memory test, math problems, images that evoke a mental response, or other mental stimuli.

The camera 414 (or cameras 414) receives image data of a field of view in front of the camera 414. In some implementations, the camera 414 receives photographic and/or video data. In some implementations, the camera 414 receives continuous photographic data (e.g., at intervals of seconds, milliseconds, or microseconds). In some implementations, the camera 414 is a visual light camera. In some implementations, the camera 414 is an infrared camera and includes an infrared light emitter. In some implementations, the camera 414 automatically initiates image data capture based on detecting certain stimulus (for example, a face of a user, an eye of a user, a pupil of a user, and/or an iris of a user). In some implementations, the camera 414 is multiple cameras.

The sensor 416 includes, for example, any of a light sensor, a proximity sensor, an ambient sensor, and/or an infrared sensor. In some implementations, the sensor 416 is communicatively coupled to the camera 414 and is configured to initiate and/or terminate image data captured by the camera 414. As shown, the sensor 416 is on the same side of the system 400 as the camera 414. In some implementations, the sensor 416 is placed proximally close to the camera 414.

Figure 14:
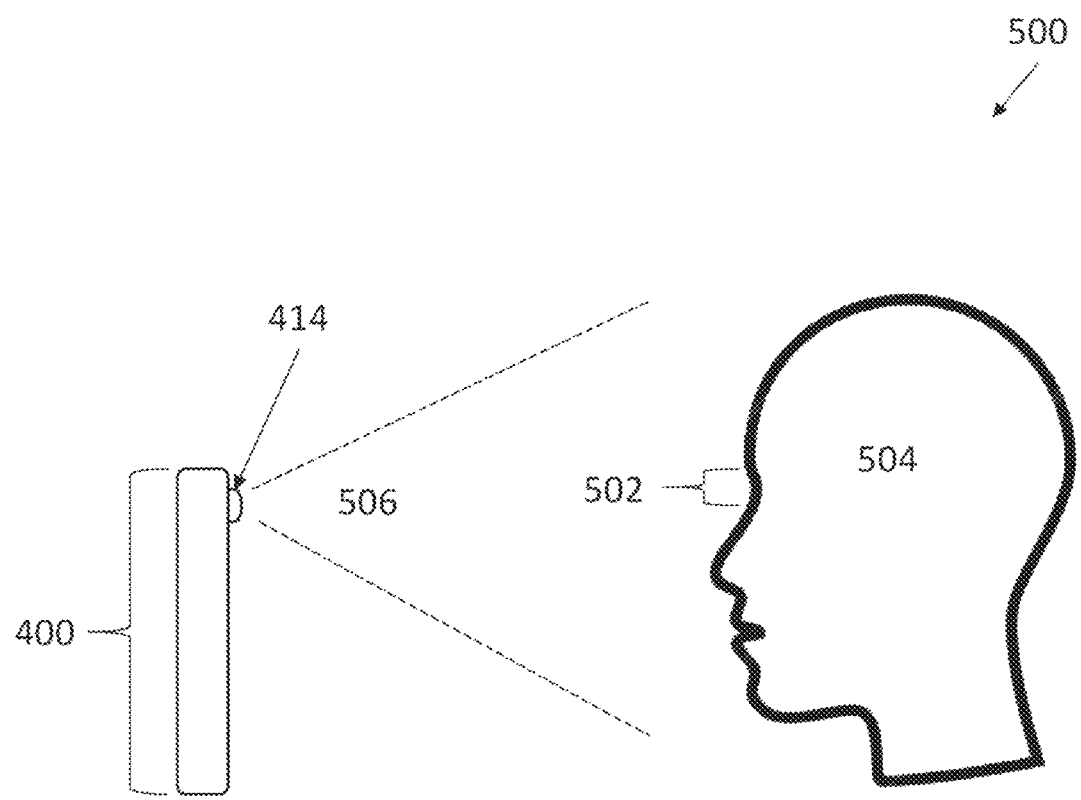
FIG. 14 depicts a system for measuring pupillary response, according to some implementations of the present disclosure.

FIG. 14 depicts a system 500 for measuring pupillary response, according to some implementations of the present disclosure. In some implementations, the system 500 is configured to receive image data of a user's face. The system 500 includes system 400, camera 414, a user's eye 502, a user's head 504, and a camera field of view 506. System 400 and camera 414 can be as discussed above with respect to FIG. 13. FIG. 14 shows that system 500 can be positioned such that the camera 414 faces a user 504. For example, the eye 502 of the user 504 can be with in the field of view of the camera 506. Various embodiments of the present disclosure can be performed when a user 504 positions system 400 in front of his or her face.

Methodology for Analyzing Pupil Response

Pupillary Light Reflex (PLR) describes the constriction and subsequent dilation of the pupil in response to light, which can serve as an important metric of autonomic nervous system function. The measurement of PLR can be used as an indicator of abnormalities with various nervous system pathways in the neurological system (and potentially other systems) and subsequently for detection of developing disease purposes. For example, alcoholism, mental health disorders such as seasonal affective disorders, schizophrenia and generalized anxiety disorder, Alzheimer's and Parkinson's diseases, autism spectrum disorders, as well as glaucoma and autonomic neuropathies associated with diabetes may result in anomalies in PLR, including changes and trends in PLR over time including, in some examples, with respect to a baseline measurement. The methodology described herein describes one such measure of one component of the PLR, performed via the use of a smartphone or analogous device.

In some implementations, the smartphone may not only capture the phenotypic data for the PLR measurement, but also process the data locally and in real-time. Similarly, other quantifiable feature extractions measured from the eye/face (such as sclera color and deposit density) can also be processed locally. This avoids sending a video or image of a user's face to the cloud/platform 160 for feature extraction. Thus, the user's privacy may be better preserved and the time taken for the measurement may be reduced. In other implementations, some or all of the analytics for the measurement may be performed at platform 160. The method and system described may have reduced noise, for example by using the ambient light sensor and the user taking measurement just before bedtime.

The method and system may also allow for the calculation of dynamically changing diameter of pupil. For example, PLR measurements may be done over time (e.g. once per week over a number of months) to be able to discover changes in a user's PLR. The method and system may generate a more robust baseline upon which to detect real-time detect statistical deviations. Such deviations may be a sign of an anomaly in the physiologic system from which the measure is causally connected.

The PLR measure described herein can be temporally and spatially coupled with other measures including, but not limited to: the voluntary reflex of a user's blink speed in response to the word "blink" projected on a screen, read by the user, neuronally processed through the motor cortex to then result in a measurable blink of the eye or eyes (which could be a measure of physiologic changes taking place in the voluntary nervous system pathway), sclera (white of the eye changing its gradients of color to red or yellow) other eye features and the iris and corneal ring (e.g. cholesterol deposits and cardiovascular risk), and several other measured features extracted from the face/eye.

These features can be measured within spatial and temporal proximity by a user, providing a more efficient user experience, can be quantitatively and longitudinally (throughout time) measured and baseline-established on an individual basis convenient, affordable, and accessible from a users' life setting (e.g. home, or non-medical). Such data may generate insights into various physiologic systems (e.g. neuro, cardio, etc.)—prior to entering a Medical setting—and on a mass, statistically significant scale, as described herein.

Pupillary light reflex (PLR) can be measured by a smart/mobile/handheld device, such as a smart phone. Although sometimes described in the context of a smartphone, the methods described herein may be implemented using other technologies including other mobile computing devices such as a camera with a flash or other light emitting source.

Training a smartphone having a high definition camera and light source to take a PLR measurement involves the following steps: imaging, image processing, and image sequence analysis. In some implementations (e.g., the system 100 of FIG. 1A, the system 130 of FIG. 1B, the system 150 of FIG. 2, the system 400 of FIG. 13 and the system 500 of FIG. 14), a smartphone is held in hand in and in a natural controlled viewing spatial distance from a user's face (e.g. within 6-24 inches horizontally from the user's face, within 6 inches vertically from the eye level and within 6 inches horizontally (right to left on the user) of the user's nose, though other distances may be possible), indoors with controlled ambient light.

Figure 15:
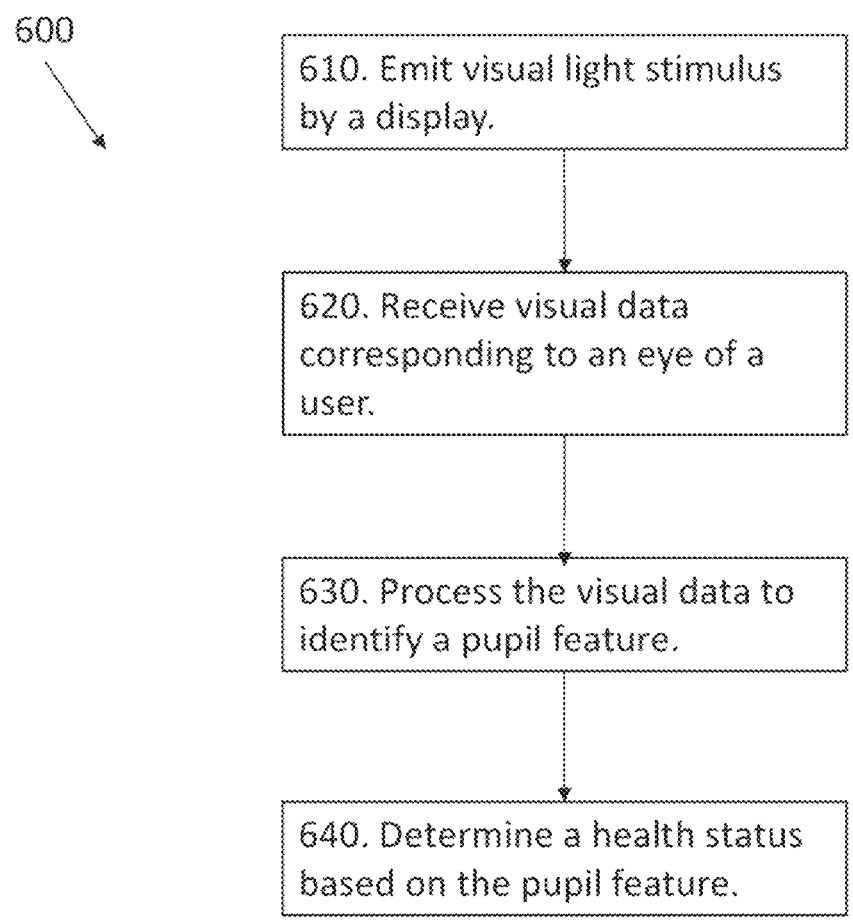
FIG. 15 depicts a method for identifying and analyzing pupillary features, according to some implementations of the present disclosure.

FIG. 15 shows an example methodology 600 that can be performed according to the various implementations of the present disclosure. For example, the methodology 600 can be performed on the system 100 of FIG. 1A, the system 130 of FIG. 1B, the system 150 of FIG. 2, the system 400 of FIG. 13, and/or the system 500 of FIG. 14. In some implementations, methodology 600 is performed in a dark room, a dimly lit room, a room with natural light, or any other setting. In some implementations, methodology 600 is performed repeatedly, including, for example, performed at night or before bedtime by a user when external variables such as light are at a minimum and controllable.

Methodology 600 begins at 610 by, in some implementations, emitting a visible light stimulus by a display (e.g., display 412 or sensor 416 of FIG. 13) or providing a light stimulus by providing an indication on a display that the user should close their eyes for a predetermined amount of time, or by providing a mental stimulus. The light stimulus, for example, causes pupil constriction. In some implementations, the pupil constriction increases as a contrast increases between the visible light stimulus and an ambient light level. The amount of visible light stimulus provided can be as determined by methodology 1400 of FIG. 24, discussed further herein.

In some implementations, the visible light stimulus is automatically emitted when a camera (e.g., camera 414 of system 400 of FIG. 13) detects that a user's face (e.g., user 504 of FIG. 14) is at an appropriate spatial distance. In other implementations, the screen may display a message to the user to close their eyes once their face is detected. In some implementations, the display first emits a notification that there will be an imminent display light stimulus.

Figure 8:
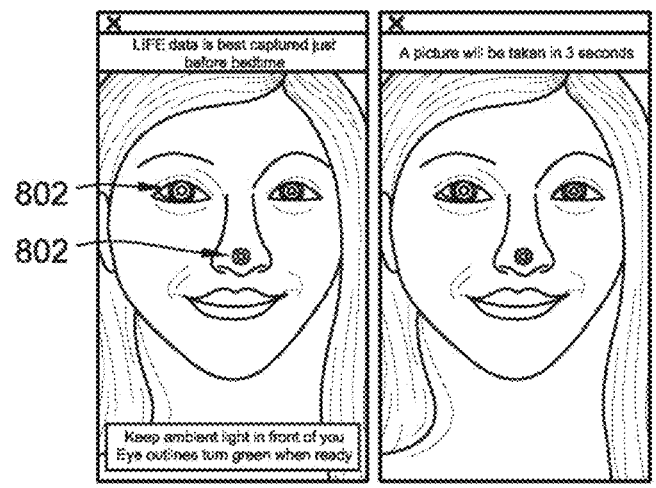
FIG. 8 is a diagram depicting an alignment for a pupillary light reflex measurement, according to some implementations of the present disclosure.
Figure 10:
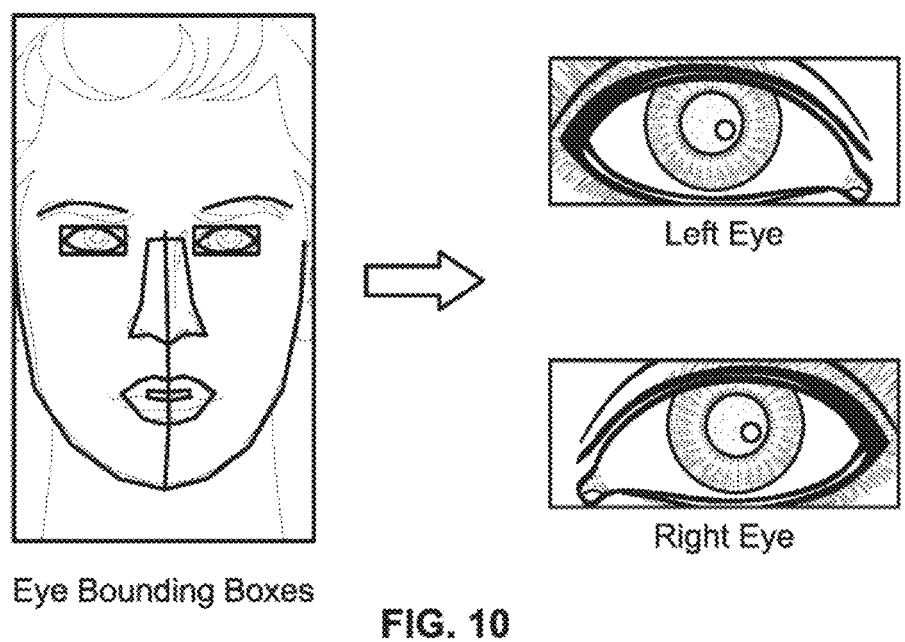
FIG. 10 is a diagram depicting a use of bounding boxes, according to some implementations of the present disclosure.

Turning briefly to FIG. 8, for example, the display can show real-time captured image data of the user's face and provide a visual graphic that a user's features are properly detected. In some implementations, the display is the display 412 of FIG. 12. For example, circles 802 can be placed on the user's eyes or nose in FIG. 8. Turning briefly to FIG. 10, the display shows exemplary bounding boxes for the user's eyes, mouth, and nose.

Referring back to FIG. 15, in some implementations, step 610 provides for first detecting a pupil. In some implementations, if the pupil is not detected, the user is notified that the setting does not meet the criteria for methodology 600. In some implementations, the visible stimulus is provided based on external health data, collected from a database holding information related to the user.

Methodology 600 then provides for receiving image data corresponding to an eye of a user at 620. Example image data includes video and/or photographic data. In some implementations, the image data is collected (e.g., collected by camera 414 of FIG. 12) over a period of time. In some implementations, a video is recorded between 30-60 frames/sec, or at a higher frame rate. In some implementations of 620, a set of still images are produced by a camera. In some implementations of 620, the image data is captured as a gray-scale video/image set, or is converted to grayscale after being received. In some implementations of the step 620, certain visual stimuli are included, such as a reflection of red eye, a pupil response, iris and sclera data, eye tracking data, and skin data.

Methodology 600 then proceeds to process the image data to identify a pupillary feature, at 630. In some implementations, the received image data is first pre-processed to clean the data. Example types of data pre-processing are discussed further below. In a brief example protocol for pre-processing data, the image data of 620 is cropped and filtered to obtain a region of image. For example, the image is filtered based on set thresholds for brightness, color, and saturation. The image data is then converted to gray scale to improve contrast between a pupil and an iris, and the pupil-iris boundary is demarcated. In some implementations of 630, shape analysis is performed to filter the image data based on a pre-selected circularity threshold. For example, the pixels are scanned for contour and convex shapes to perform the shape analysis. In some implementations of 630, a baseline image is compared to the received image data of 620 to aid in pre-processing.

In some implementations, methodology 600 further includes receiving distance data associated with the at least one eye of the user from the distance detector. The distance data is processed to determine a distance of the at least one eye of the user from the distance detector. As such, in some implementations, step 630 includes processing the distance data and the image data to determine at least one pupillary feature.

In some implementations, the at least one pupillary feature includes a diameter of a pupil of the at least one eye of the user. In some implementations, the at least one pupillary feature includes an absolute measurement. The absolute measurement can be an actual measure in millimeters, such as a baseline pupil diameter. In contrast to some other metrics, such as velocity, a relative change is determined such that an absolute measurement is not required. In some implementations, the at least one pupillary feature is determined based at least in part on a preexisting measurement of a diameter of a corresponding iris of the at least one eye of the user.

In some implementations, step 630 of methodology 600 further provides for determining a surface area of pupil and iris regions, as detected in the image data. For example, imaging analysis software algorithms determine pupil size parameters across a series of recorded images by evaluating the elapsed time between each image to determine the rate at which the pupil size changes over time.

In some implementations, identification information is optionally removed from the sensor data at step 630. Stated differently, the most relevant key phenotypic features of interest may be extracted from the raw image data. Example features include: pupil velocity (e.g. magnitude and direction), sclera color, a measure of tissue inflammation, and/or other characteristics. These features can be represented as scalar numbers after extracting relevant metrics from the underlying raw data. The image of the user that may be identifiable is not utilized.

In some implementations, step 630 provides for determining whether additional data is needed. For example, an alert is provided at a display to identify the type of measurement that is needed and user instructions for capturing the appropriate type of measurement. Alternatively, or additionally, some implementations of step 630 provide for interpolating or extrapolating pupillary measures based on the trajectory observed of the collected image data.

In some implementations of step 630, the features include: (1) pupil response latency, which includes the time taken for a pupil to respond to a light stimulus measured, for example, in milliseconds; (2) maximum diameter, which is the maximum pupil diameter observed; (3) maximum constriction velocity (MCV), which is the maximum velocity observed over the constriction period; (4) average constriction velocity (ACV), which is the average velocity observed over the total constriction period; (5) minimum pupil diameter, which is the minimum diameter observed; (6) dilation velocity, which is the average velocity observed over the total dilation period; (7) 75% recovery time, which is the time for the pupil to reach 75% of its initial diameter value; (8) average diameter, which is an average of all diameter measurements taken in a time series; (9) pupil escape; (10) baseline pupil amplitude; (11) post-illumination pupil response; (12) maximum pupil diameter; (13) any other pupillary response measurements, as known in the art; or (14) any combination thereof. In some implementations of 330, similar metrics are determined of the iris.

In some implementations, constriction latency is measured as constriction($t_{flash}$) minus constriction($t_{initial}$). In some implementations, constriction velocity is a measure of the rate at which the pupil constricts in millimeters/second. For example, constriction amplitude is measured as (Diameter$_{max}$ prior to light exposure)–(Diameter$_{min}$ following light exposure). For example, constriction percentage is measured by taking the constriction amplitude as a percentage of Diameter$_{max}$. For example, dilation velocity is a measure of the rate at which the pupil dilates in millimeters/second. Many of the features listed above can be derived by evaluating the diameter of the pupil at a first image, the diameter of the pupil at a second image, and a length of time between the two images, as would be readily contemplated by a person skilled in the art. Furthermore, a person skilled in the art would readily understand that dilation latency, dilation velocity, dilation amplitude, and dilation percentage can be similarly calculated based on the data provided at step 620.

Additional features can include, for example: the voluntary blink reflex speed in response to screen projected word "blink" (which could be a measure of the voluntary nervous system pathway), sclera (white to yellowing of the eye) color features, iris and corneal ring features (cholesterol deposits and cardiovascular risk), and several other measured features extracted from the face/eye.

Methodology 600 then provides for, at step 640, determining a health status based on the pupillary feature identified in step 630. In some implementations of 640, the features, as determined at 630, are compared to corresponding values of healthy individuals in order to identify abnormalities. In some implementations, the features are compared to longitudinal data of the user; variations in currently-measured values from an established longitudinal baseline (individual) can be indicative of a disease state or a performance measure for disease. In some implementations of 640, an individual user baseline is established over longitudinal use of a system 500 and a notification is provided when the pupillary feature identified in 630 deviates from the established individual baseline by 1.5 standard deviations or by another, pre-determined threshold deviation. For example, the threshold deviation varies according to disease state. In some implementations, 640 relies on a universal, or external, database of healthy individuals until the individual user has provided twenty separate PLR measures according to methodology 600. For instance, in some examples this may include a progression of a neurologic disease, such as Alzheimer's, Dementia, Parkinson's, depression, anxiety, or schizophrenia. For instance, the progression in Alzheimer's or Dementia may be based on a trend in change of MCA or MCA. In some examples, the progression of Alzheimer's may be based on a trend in the change of PPR in response to a mental task. In some examples, the mental task may be administered through the display or screen of a mobile device that is also utilized to capture the eye features using its camera and determine the PPR. Accordingly, in that instance, the screen could display a multitude of mental stimuli or aid in administering mental tasks while the front facing camera of a smart phone or handheld device capture eye features to measure PPR.

In some implementations of methodology 600, the image data includes data of both eyes of a user. At step 630, each pupil's reflex is analyzed separately; but, at step 640, the features of the two are analyzed together to determine a health status, as varying pupillary light reflexes between each eye can be telling of a diseased state (e.g. stroke).

In some implementations of methodology 600, an alert is provided based on the received data. For example, if a digital marker for a disease is detected, then a pre-disease detection alert is received by system 400, and presented, for example, on display 412. In some implementations, an audio alert can supplement or replace a graphical alert. The user is thus made aware of developing diseases, disorders, or disease precursors and can take further action. Other information described above, such as a suggestion to contact a physician for a physical examination, may also be received and presented to the.

In some implementations, holding the smartphone in this position for a controlled amount of time (e.g. at least 5 seconds), will activate an App (via sensors and software) to video record a subject's face (particularly the eye and reflex of the pupil) at 60+ or 120+ frames per second in HD upon being catalyzed by a stimuli of a brief intense flash of light provided from the touchscreen or other light source on the smartphone during recording. This flash of light is focalized and of known intensity from both its origin and can the intensity of light reaching the pupil can also be determined by the square of the distance from the source and the pupil.

Thus, images of the user's face are captured before, during and after the brief flash of intense light. In some implementations, the recording starts at least 1 second and not more than 5 seconds before the flash of light and continues for at least 3 seconds and not more than 8 seconds after the flash of light. Of note, the intensity that reaches the pupil can be inferred by the square of the distance between pupil and light source.

Pupil Response Curves

Figure 16A:
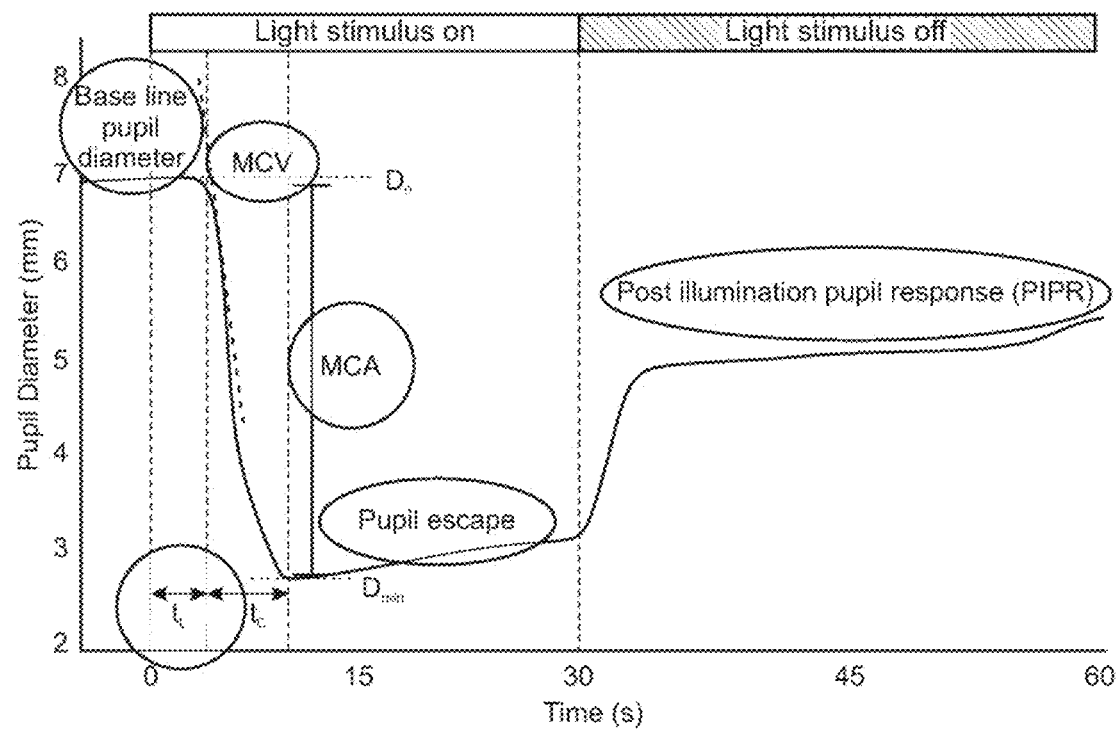
FIG. 16A depicts a pupillary response separated into sub-phases, according to some implementations of the present disclosure.

FIG. 16A depicts an example pupil response curve and the various features that can be identified at different points in the curve. For example, these features are analyzed with respect to methodology 600, discussed above. FIG. 16A demonstrates that when a light stimulus is on, a baseline pupil diameter is first detected; MCV, MCA, and pupil escape are subsequently evaluated. When the light stimulus is turned off, a post-illumination pupil response (PIPR) can be evaluated.

Figure 16B:
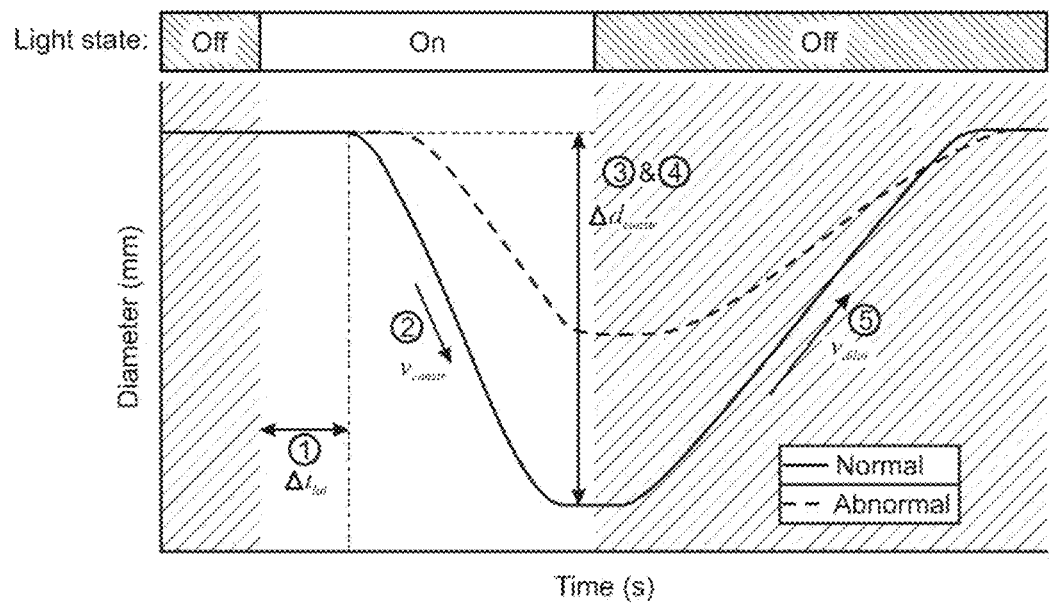
FIG. 16B depicts example pupillary responses as compared between a healthy and unhealthy subject, according to some implementations of the present disclosure.

FIG. 16B depicts another example PLR curve, including: (1) latency, (2) constriction velocity, (3) constriction amplitude, (4) constriction percentage, and (5) dilation velocity. The dashed line shows an abnormal PLR curve with increased latency, slower velocities, and diminished amplitude than the normal PLR curve shown by the solid line.

Automatic Facial Detection

Automatic facial detection is possible using the tip of the nose and two pupils. In some implementations, the controlled spatial distance mentioned above is achieved by the user aligning their face with the 3 red triangular dots on the viewfinder (2 for the pupils, 1 for the tip of the nose). Via machine vision, the pupils are recognized as aligned with the red dots and the nose tip (based on RGB color of the nose skin) is aligned with nose tip. Then ambient light sensor is used to check for any ambient light (noise) that would add confounding variables to the measure. If alignment (e.g., depth and/or angle) and/or lighting are sufficient, then the red dots turn green and the user is notified that measure ready to be taken in a certain amount of time. FIG. 8 indicates this process.

A flash is provided and video is captured. Facial detection may be accomplished using one or more frames of the video. Thus, after capture of the video above, with machine vision based algorithmic assistance, the smartphone automatically detects the pixel-based locations of the tip of the nose, as well as the two pupils (which may also be projected on the screen), to ensure measurements are trigonometrically and spatially consistent. The spatial geometry and distance of these three reference points are cannot be voluntarily nor involuntarily changed over time by the facial muscles, further ensuring control and consistency.

The facial detection/machine vision portion of this measure may be accomplished using open-source and/or proprietary software. Consequently, faces and eyes can be detected. The input video/video frames are in grayscale in some implementations. If a face is detected in the video, the system will proceed to detect eyes within the coordinates of the face. If no face is detected, the user will be notified that the given video does not meet the criteria for effective detection.

A face recognition algorithm to guide the user during a Pre-Capturing phase in real time may be used. In some implementations, this could be achieved by using the OpenCV (Open Source Computer Vision Library), ARKit (Augmented Reality Kit), or other facial recognition mechanisms. Using face recognition, the eye position on the image can be identified and the user directed to manipulate the device to situate the camera in the desired position. Once the camera is situated—the image data capturing phase may occur. Modern smartphones may have the capacity to emit over 300 nits (1 candela/m2). Video footage can be as short as 10-20 seconds may be sufficient to capture enough data for PLR analysis. Modern smartphone camera(s) (e.g. camera 114 of FIG. 1) are used to capture the video before, during and after the screen flash.

In some implementations, face capture in combination with face and eye recognition can also be used in performing a PLR measurement. Some facial recognition frameworks, such as Vision Framework, can detect and track human faces in real-time by creating requests and interpreting the results of those requests. Such tool may be used to find and identify facial features (such as the eyes and mouth) in an image. A face landmarks request first locates all faces in the input image, then analyzes each to detect facial features.

In some implementations, face tracking, for example via an augmented reality session, can be used. An example of one such mechanism is ARKit. Using such a mechanism the user's face may be detected with a front-facing camera system. The camera image may be rendered together with virtual content in a view by configuring and running an augmented reality session. Such a mechanism may provide a coarse 3D mesh geometry matching the size, shape, topology, and current facial expression and features of the user's face. One such mechanism may be used to capture and analyze images or multiple mechanisms can be combined. For example, one can be used to capture images, while another is used to analyze the images.

Following detection, information not used in PLR and other detection described herein may be eliminated by establishing cropping bounds, excluding information such as the pixels around the eye socket, and the pixels above the eyelid towards the eyebrow. Each pupil's reflex will be analyzed separately, but a subject's two pupils remain as a pair in the dataset. Measurement of both pupils may be useful because as PLR that varies between an individual's eyes can be indicative of a diseased state (e.g. stroke). In some implementations, varying pupillary reflexes relative to a retrospectively established temporally longitudinal baseline can also be indicative of a disease state (e.g. neurodegenerative diseases) and/or a performance measure for the disease.

Pre-processing & Processing the Data

In some implementations, the received image data is pre-processed. Example pre-processing techniques are discussed herein.

Frames in the sequence are smoothed to de-noise the system of natural fluctuations in the pupil, color variance in the irises, as well as variance caused by the device itself. A Gaussian smoothing operator can be used to slightly blur the images and reduce noise. The 2D Gaussian equation has the form:

$$G(x, y) = \frac{1}{2\pi\sigma^2} e^{\frac{-(x^2+y^2)}{2\sigma^2}}$$

where sigma is the standard deviation of the distribution, which may be given by:

$$\sigma = \sqrt{\frac{1}{N} \sum_{i=1}^{N} (x_i - \mu)^2}$$

where x is the $i^{th}$ PLR measurement, $\mu$ is the mean PLR, and N is the total number of PLR measurements. In some implementations, a particular measurement of PLR that is probabilistically significant, such as +/− one standard of deviation or +/− 1.5 standards of deviation, trigger an alert that an anomaly was detected in the neurological system. In some such implementations, the alert may be for a particular predisease condition. In other implementations, the alert may simply indicate that an anomaly was detected.

In some implementations of the present disclosure, PLRs are represented as Fourier transformations. In some such implementations, smoothing the Fourier transform can yield a more easily understood graph. For example, when using a histogram representation of the smoothed grayscale frames, a threshold function binarizes the images. This threshold function can be determined by the distinction between dark and light pixels on the histogram. Based on this, the images can be binarized in such a way that distinguishes the sclera from the pupil by labelling white parts of the image with a 1, and black parts of the image with a 0. This effectively generates a black square with a white circle representing the pupil clearly for analysis.

Pupils are generally shaped as ellipses, but can be represented as a circle by averaging the axes. Diameter can be measured in pixels between the two white pixels farthest away from each other. This pixel measurement can be converted to millimeters using a fiducial of known dimensions held near the eye. For example, depth of the smartphone from the face can be determined using a dot projector in a smartphone (e.g., recent iPhones). Other mechanisms for obtaining the fiducial may be utilized in other implementations.

The differential equation that describes a pupillary light reflex in terms of pupil diameter flux as a function of light can be written as follows:

$$\frac{dM}{dD}\frac{dD}{dt}(t) + 2.3026\tanh^{-1}\left(\frac{D-4.9}{3}\right) = 5.2 - 0.45\ln\left(\frac{\Psi[t-\tau\tau]}{4.8118*10^{-10}}\right)$$

$$M(D) = \tanh^{-1}\left(\frac{D-4.9}{3}\right)$$

D is measured as the diameter of the pupil (mm), and Φ(t−τ)r represents the light intensity that reaches the retina in time t. Thus, the using the data from the video (e.g. the diameter of the white circle representing the pupil in each frame, the time between frames and the conversion between pixels to millimeters), the differential equation above may be utilized to determine the pupil velocity. The pupil velocity both in reacting to the flash of light (decreasing in diameter) and recovery (increasing in diameter) can be determined. In some implementations, the PLR can therefore be measured.

Given the pupil diameter as a function of time, detection/diagnostics can focus on a number of important metrics. For example, in some implementations, the following may be of interest:

Constriction latency as measured as $t_{flash}-t_{initial}$ constriction.

Constriction velocity—the rate at which the pupil constricts in millimeters/second.

Constriction amplitude can be measured as ($D_{max}$ prior to light exposure)–($D_{min}$ following light exposure).

Constriction percentage can be determined by taking the constriction amplitude as a percentage of $D_{max}$, and dilation velocity is a measure of the rate at which the pupil dilates in millimeters/second. Thus, the PLR can be determined. In some implementations, the PLR may be provided to the user. These metrics can all be compared to PLR curves of healthy individuals in order to identify abnormalities. Thus, the user may be notified of any issues based on the PLR. Further, the PLR determined as described herein can be combined with other measures to determine whether markers for other conditions exist.

The light stimulus (the brief flash of light described herein that occurs after video capture starts) results in a rapid reduction in pupil diameter. Latency (tL) is calculated as the elapsed time between light onset and the start of constriction. The pupil rapidly constricts (maximal constriction velocity; MCV) from the baseline (D0) pupil diameter to the minimum ($D_{min}$) pupil diameter; the constriction time (tC) and maximum constriction amplitude (MCA) are calculated as the time interval and size difference between these two values, respectively. At offset of light stimulus or during sustained light stimulation the pupil undergoes a period of rapid redilation or pupillary "escape" to a partially constricted state. Subsequently, the pupil slowly returns to the baseline diameter In some implementations, data extracted from the video, such as the pixel data described herein, is provided to a server, such as platform 160 of FIG. 2. Platform 160 then determines PLR as discussed above. In other implementations, the video data is provided to platform 160, which extracts the pixels data and then performs the calculations for PLR. For example, the entire pupil size detection can be done on the smartphone in real time. Only a small amount of data can be sent to the platform 160 or other server for statistical analysis. The results of the analysis may be available in seconds. In other implementations, some or all of the calculations described herein are performed on the smartphone.

In implementations where the smartphone extracts some or all of the data, less personally identifiable information is transmitted from the smartphone and stored via platform 160. Further, as described herein, some or all of data processing may be performed on the smartphone. Consequently, even less personal information may be transmitted to platform 160. Thus, security may be improved. Such an implementation may also be cheaper at scale as most of the computation will happen on user devices 130 rather than in the Cloud/platform 160.

Other implementations of methods for performing a PLR measurement usable in detecting pre-disease conditions or for other purposes may also be used. In some implementations, a weekly bedtime measurement using a modern iPhone or analogous device (hereinafter "modern smartphone") in dimmed light setting of user's bedroom.

In some implementations, the phases of a PLR measurement can be: i) Pre-Capturing; ii) Capturing the footage; iii) Pre-processing; iv) Processing; v) Data Extraction; and vi) Analysis. While (i) and (ii) happen on the device 130 (e.g. a modern smartphone) (iii), (iv), (v) and (vi) may happen in the Cloud/on platform 160. In some implementations, some or all of (iii), (iv), (v) and (vi) may occur locally.

A face recognition algorithm to guide the user during the Pre-Capturing phase in real time may be used. In some implementations, this could be achieved by using the OpenCV (Open Source Computer Vision Library), ARKit (Augmented Reality Kit), or other facial recognition mechanisms. Using face recognition, the eye position on the image can be identified and the user directed to manipulate the device 130 to situate the camera in the desired position. Once the camera is situated—the capturing phase (ii) may occur. Modern smartphones may have the capacity to emit over 300 nits (1 candela/m$^2$). Video footage can be as short as 10-20 seconds may be sufficient to capture enough data for PLR analysis. Modern smartphone camera(s) (e.g. sensor 131) are used to capture the video before, during and after the screen flash.

Figure 9:
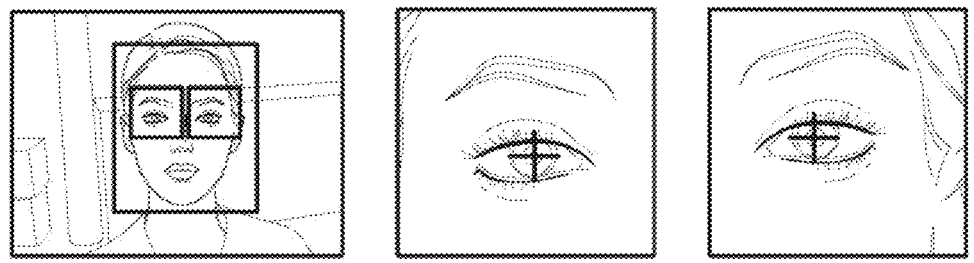
FIG. 9 is a diagram depicting cropping and pupil response, according to some implementations of the present disclosure.
Figure 9:
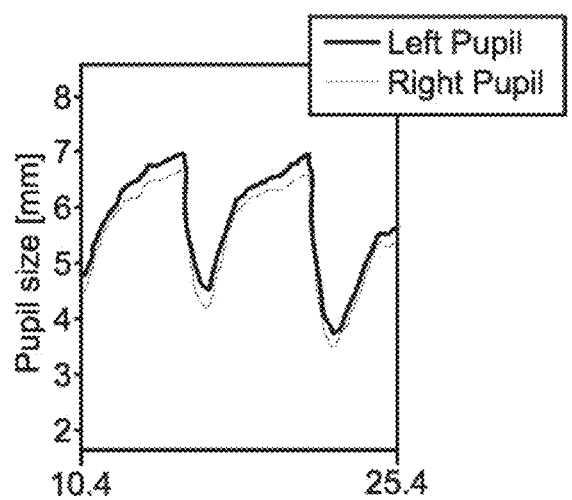

In some implementations, pre-processing (step (iii)) includes cropping the footage to include the region of each eye as shown in FIG. 9. This could be implemented by applying the simple heuristics of the known structure of the human face. In some implementations, the captured footage may be uploaded and stored via system 150. If so, the minimum amount of video footage of the most valuable area containing each pupil may be uploaded.

The footage will then be submitted for processing at stage (iv). At this stage the video is deconstructed into the series of images to be processed one by one. Images are manipulated to eliminate the aberrations of eye glasses, blinking and small hand movements. As such, in some implementations, frames with blinking associated with the at least one eye of the user are removed. In some implementations, aberrations with eye movements associated with the at least one eye of the user are removed.

Pupil Boundary Detection using Entropy of Contour Gradients may be used to extract the size of each pupil and create data series which could be visualized. The timing of the flash is known, allowing the response time of each pupil along with the amplitude of the reflex to be measured. Data for PLR measurements of a user are also shown in FIG. 9.

In some implementations, only the certain data (for example maximum and minimum pupil size and the corresponding times). Footage may be reconstructed from the processed images, leaving only the most valuable parts in long term storage. This long term storage could be used to re-calculate the PLR if adjustments are made to the calculation. The Analysis stage (vi) may apply the statistical analysis methods and use the newly acquired PLR measurements, for example to compare new data with established baseline, identify trends and possible artifacts.

The use modern smartphone tools and/or computing power, such as the TrueDepth IR Camera and ARKit in the iPhone X, may provide additional utility. In some implementations, the PLR calculation may happen in real time, allowing the user to receive the feedback from the system rapidly. If the entire pupil size detection is done on device 130 in real time—only a small amount of data may be sent to platform 160 for statistical analysis. The results of the analysis may be available in seconds. Less personally identifiable information will be stored in the cloud/on platform 160. This mechanism may also be more cost effective as most of the computation will happen on user devices rather than in the Cloud/on platform 160.

In other implementations, performing the majority of the data processing in the cloud/on platform 160 allows for a lean device application. In some implementations, an eye tracker may be used to capture frames of eyes with different levels of dilation. The user can manually tag the pupil diameters for each frame. Using the tagged data, a segmentation model can be trained using the tagged pupils. For example U-Net or an analogous service can be used to output shapes from which diameter may be inferred. A pipeline may be implemented to process recorded frames of video and graph the pupil dilation over time.

In some implementations of processing the data, hue, saturation, and brightness values are used to filter the received image data. For example, pixels may be filtered out if the pixels have a "V" value (which represents brightness) of greater than 60. In another example, the pixels may be filtered based on LAB values, where "L" represents a brightness of the pixel, and "A" and "B" represent color-opponent values. Because the pupil is the darkest feature of the eye, pixels may be filtered out which have an "L" value greater than 50, thereby leaving only the pixels which are relatively darker and more likely to include the pupil.

Additional example processing steps include (1) duplicating the filtered image, discarding what has been filtered out to just show the region of interest (ROI), (2) converting the filtered ROI pixels to grey scale, (3) filtering grey scale pixels based on brightness or intensity values, for example, by filtering pixels having an L value higher than 45, (4) scanning the remaining pixels for contours and convex shapes, (5) scanning the pixels for incremental gradients in grey scale values of pixels, (6) constructing shapes based on, or defined by, the contours, (7) filtering those shapes based on size and circularity, (8) determining a surface area of pupil region and iris region, and (9) determining a relative change in the two regions over time.

In some implementations of filtering based on circularity, the device filters out values which are not at or around a 1.0 circularity value. For example, circles have circularity values at or near 1.0, while an elongated ellipse may have a circularity value of around 0.25.

In some implementations, face capture in combination with face and eye recognition can also be used in performing a PLR measurement. Some facial recognition frameworks, such as Vision Framework, can detect and track human faces in real-time by creating requests and interpreting the results of those requests. Such tool may be used to find and identify facial features (such as the eyes and mouth) in an image. A face landmarks request first locates all faces in the input image, then analyzes each to detect facial features.

In other implementations, face tracking, for example via an augmented reality session, can be used. An example of one such mechanism is ARKit. Using such a mechanism the user's face may be detected with a front-facing camera system. The camera image may be rendered together with virtual content in a view by configuring and running an augmented reality session. Such a mechanism may provide a coarse 3D mesh geometry matching the size, shape, topology, and current facial expression and features of the user's face. One such mechanism may be used to capture and analyze images or multiple mechanisms can be combined. For example, one can be used to capture images, while another is used to analyze the images.

In such implementations, bounding boxes can be used to extract the eye images. Such a tool may provide cropped images of the eyes. This bounding box will be relative to the size and coordinates of the image from the camera. FIG. 10 depicts an example implementation of the use of bounding boxes.

Predicting Health Status Based on Pupillary Features

Figure 17:
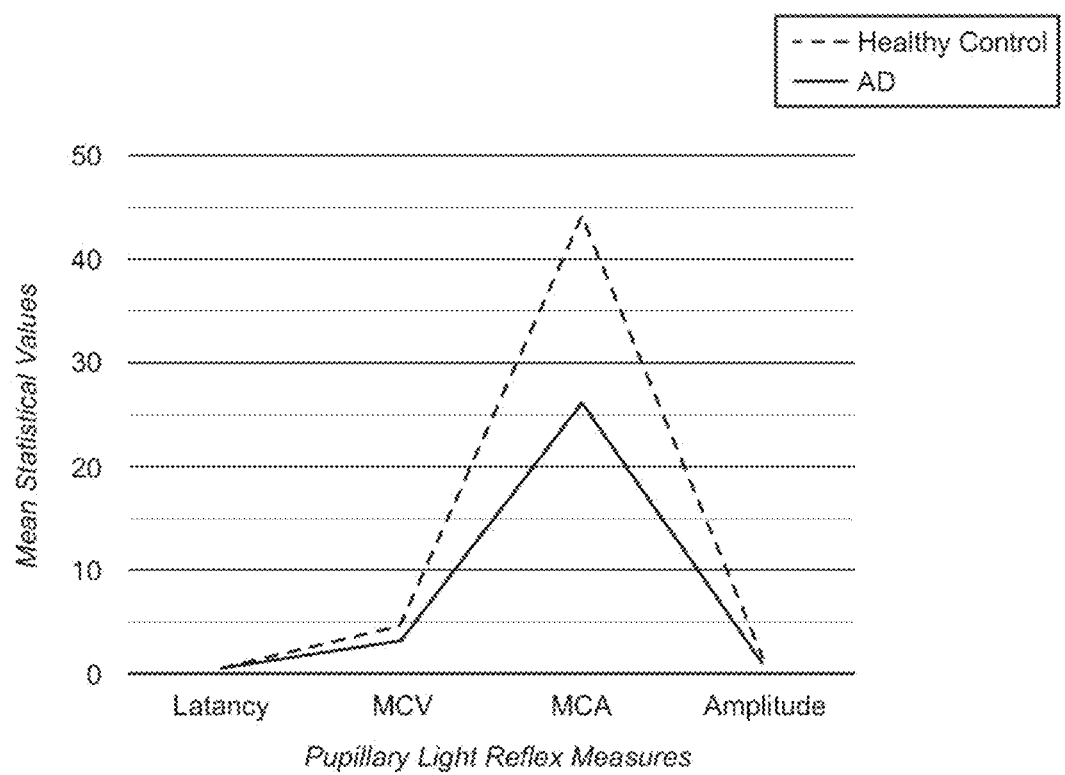
FIG. 17 depicts average measured pupillary responses, according to some implementations of the present disclosure.

Various aspects of step 640 of methodology 6600 of FIG. 15 can be used to identify whether the user has various disease states, disease severity, or other health ailments. FIGS. 17-20 herein demonstrate example data that corresponds to example health statuses. FIG. 17 depicts average measured pupillary responses correlate to Alzheimer's Disease. For example, FIG. 17 depicts that latency, MCV, MCA and Amplitude have significant differences between a group with cognitively healthy patients and a group with Alzheimer's Disease patients.

Figure 18:
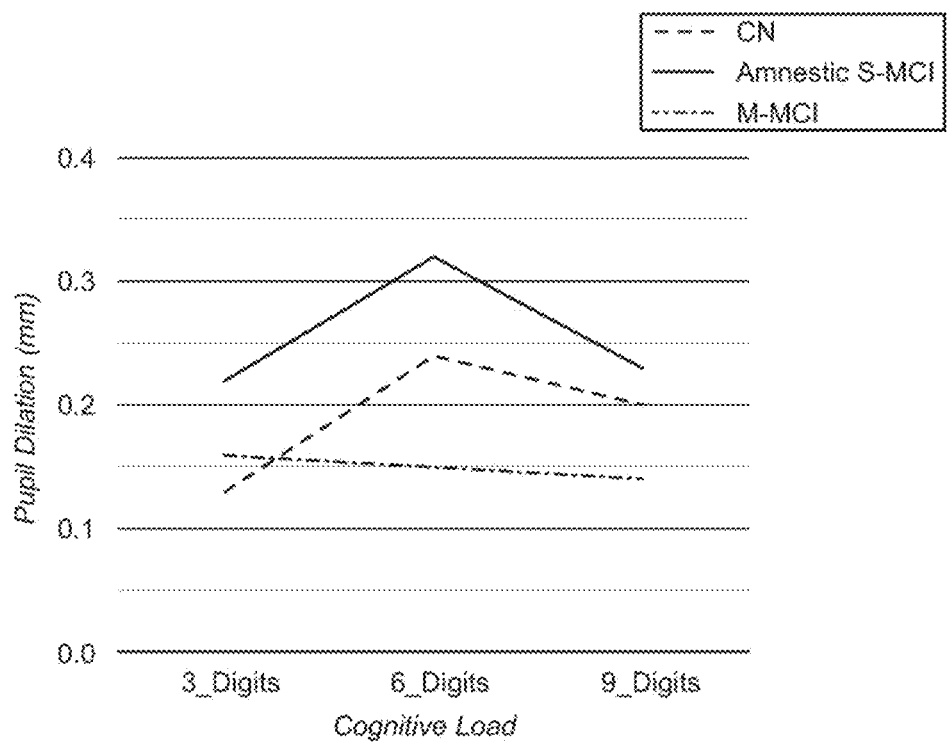
FIG. 18 depicts example pupillary responses to cognitive load, according to some implementations of the present disclosure.
Figure 19:
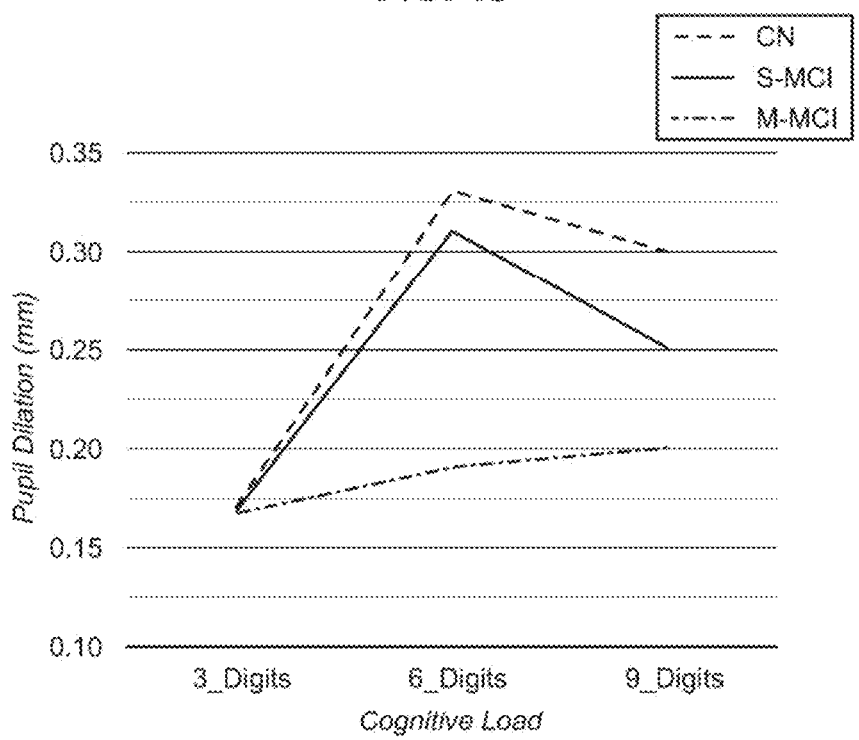
FIG. 19 depicts example pupillary responses to cognitive load, according to some implementations of the present disclosure.

FIGS. 18-19 show example pupillary responses to cognitive load, according to some implementations of the present disclosure. FIGS. 18-19 demonstrate that the psychosensory pupil response (i.e. "PPR") and Alzheimer's Disease are correlated. Cognitive load is measured by whether a subject can recall spans of 3, 6, or 9 digits. FIGS. 18-19 demonstrate that with increased cognitive load, the amnestic single-domain mild cognitive impairment (S-MCI) group showed significantly greater pupil dilation than a cognitively health control group (CN). Furthermore, at certain cognitive loads, the multi-domain mild cognitive impairment (M-MCI) group showed significantly less dilation than both the cognitively normal and S-MCI groups. This indicates a cognitive load well beyond the capacity of the group. Accordingly, as disclosed herein, PPR may be measured to determine cognitive load, and to determine a longitudinal progression of Alzheimer's over time by measuring the change in cognitive load in a recall test (such as describe above) or other mental tests over time. Accordingly, the systems and methods disclosed herein may determine a trend in cognitive load and therefore be able to determine an indication of progression of Alzheimer's or dementia.

Figure 20:
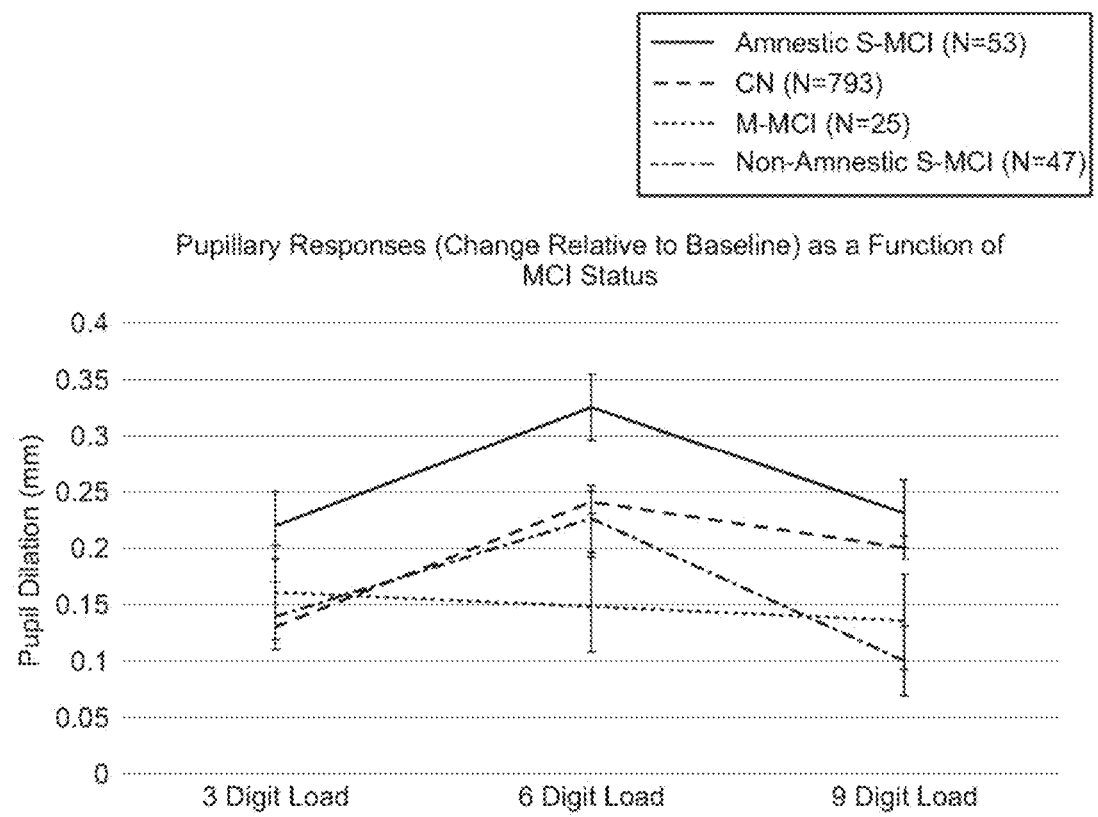
FIG. 20 depicts example pupillary responses as a function of mild cognitive impairment, according to some implementations of the present disclosure.

FIG. 20 depicts example pupillary responses as a function of mild cognitive impairment, according to some implementations of the present disclosure. For example, this data shows pupil dilation increases in response to a 6-digit load from a 3-digit load, but decreases once capacity is reached at a 9-digit load. Therefore, the present disclosure contemplates that individuals with lower cognitive ability would show greater pupil dilation under lower loads and less at higher loads.

Pupil Segmentation

The present disclosure provides for pupil segmentation methods. The images of the eyes may be segmented into three main parts: pupil, iris, and sclera. Image Segmentation Algorithms can be used to provide the desired segmentation. For example, a pupil segmentation process is disclosed herein. First, a greyscale image of an eye is received. Then, a balanced histogram is created based on a grey level of each of the pixels. For example, balanced histogram thresholding segmentation, K-means clustering, or edge detection and region filling can be used.

Figure 11:
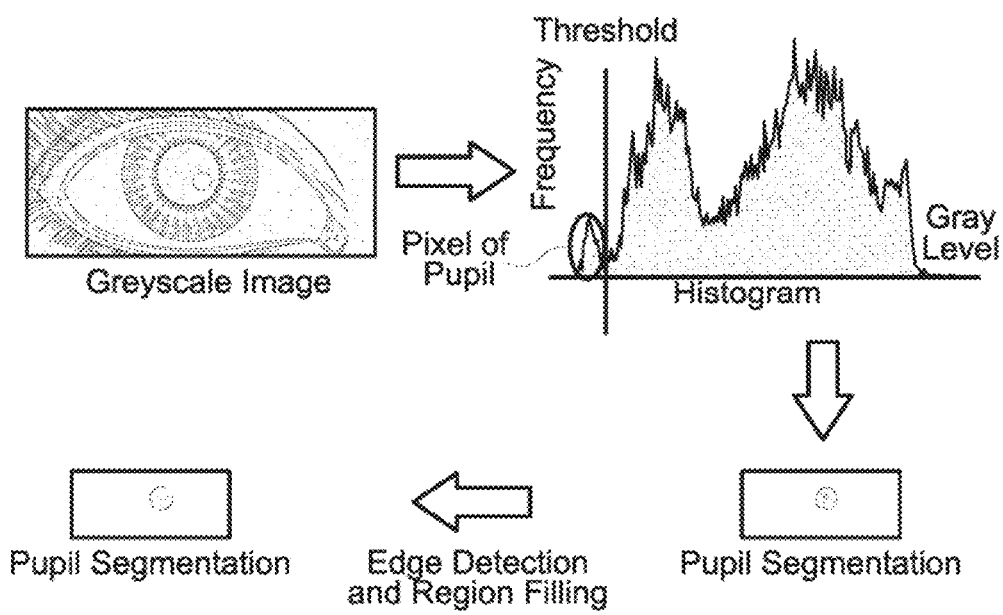
FIG. 11 is a diagram depicting image segmentation, according to some implementations of the present disclosure.

FIG. 11 depicts mage segmentation. Balanced histogram segmentation converts images to grayscale, analyzes pixels of eye images, creates histograms and sets the threshold for pupils, which will be the darkest pixels. In some implementations, K-means clustering chooses k (k is 4 in this example) data values as the initial cluster centers. The distance between each cluster center and each data value is determined. Each data value is assigned to the nearest cluster. The averages of every cluster are then updated and the process repeated until no more clustering is possible. Each cluster is analyzed to determine which cluster includes the pixels of pupil, getting the segmentation result. This method can be used to segment the interest area from the background based on the four main parts in the eyes having different colors: black pupil, white sclera, colored iris, and skin background.

The example implementations of FIG. 11 further provides for edge detection and region filling, which enhances the image and links the dominant pixels of the pupil. Holes of certain shapes and sizes are filled to get the final results of segmentation. After segmentation, the area of the pupil is determined, measured in pixels. This pixel measure is converted to a physical size (e.g. millimeters) based on a scale of the camera which collected the image data.

Red Eye Reflex

Figure 21:
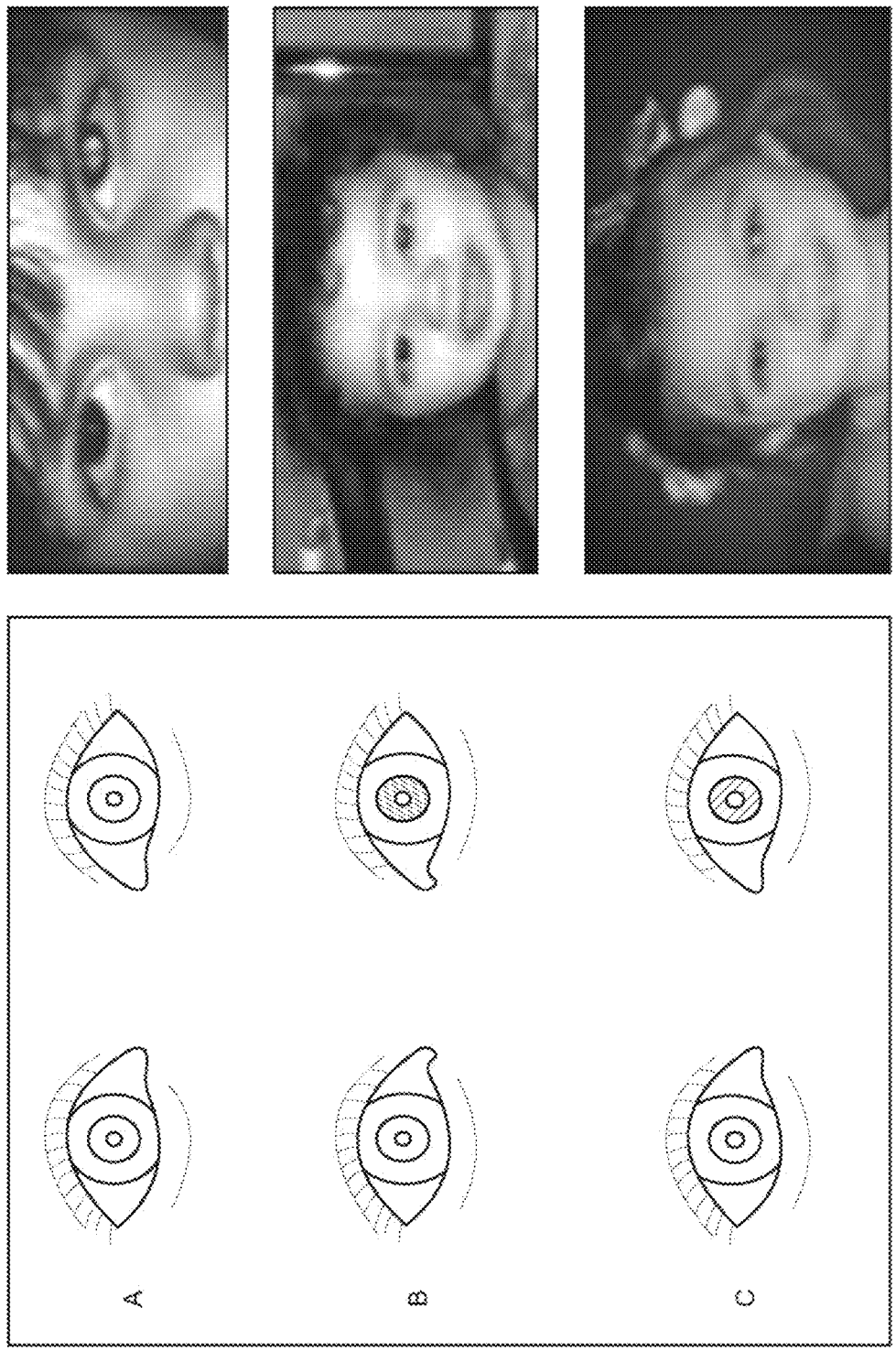
FIG. 21 depicts example red eye reflex, according to some implementations of the present disclosure.

Referring now to FIG. 21, which depicts example red-eye reflex data collection, according to some implementations of the present disclosure. For example, image data is collected which highlights the red reflection in the retina of a user's eye. The present disclosure then provides for determining whether the red reflection is dim (which can be a sign of Strabismus or retinoblastoma), whether the reflection is yellow (which can be a sign of Coat's Disease), and/or whether the reflection is white or includes eyeshine (which can be a sign of retinoblastoma, cataracts, retinal detachment, and/or an eye infection). These methodologies can accordingly provide features which are used to determine a health status, according to, for example, steps 630 and 640 of methodology 600 of FIG. 15.

Cornea Light Reflex

Figure 22:
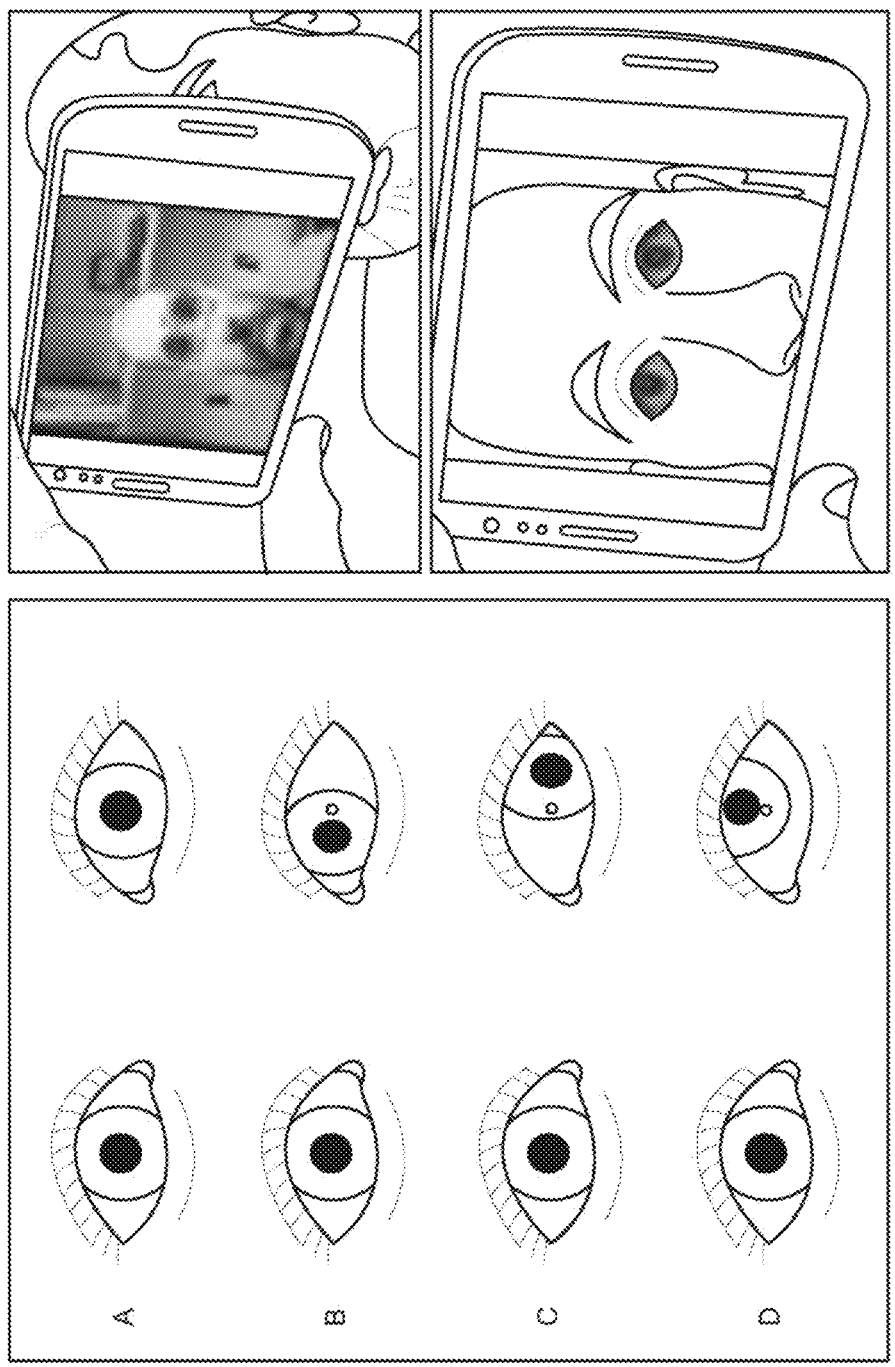
FIG. 22 depicts example cornea light reflex, according to some implementations of the present disclosure.

Referring now to FIG. 22, which depicts example cornea light reflex data collection, according to some implementations of the present disclosure. For example, image data is collected which captures the degree of strabismus (eye misalignment). The present disclosure then provides for determining whether the captured data includes any of: (A) a tiny light dot in the center of a pupil; and (B), (C) & (D)

deviations in dot placement from a center of the pupil, demonstrating eye misalignment. These methodologies can accordingly provide features which are used to determine a health status, according to, for example, steps 630 and 640 of methodology 600 of FIG. 15.

Measuring Pupil Diameter

Figure 23:
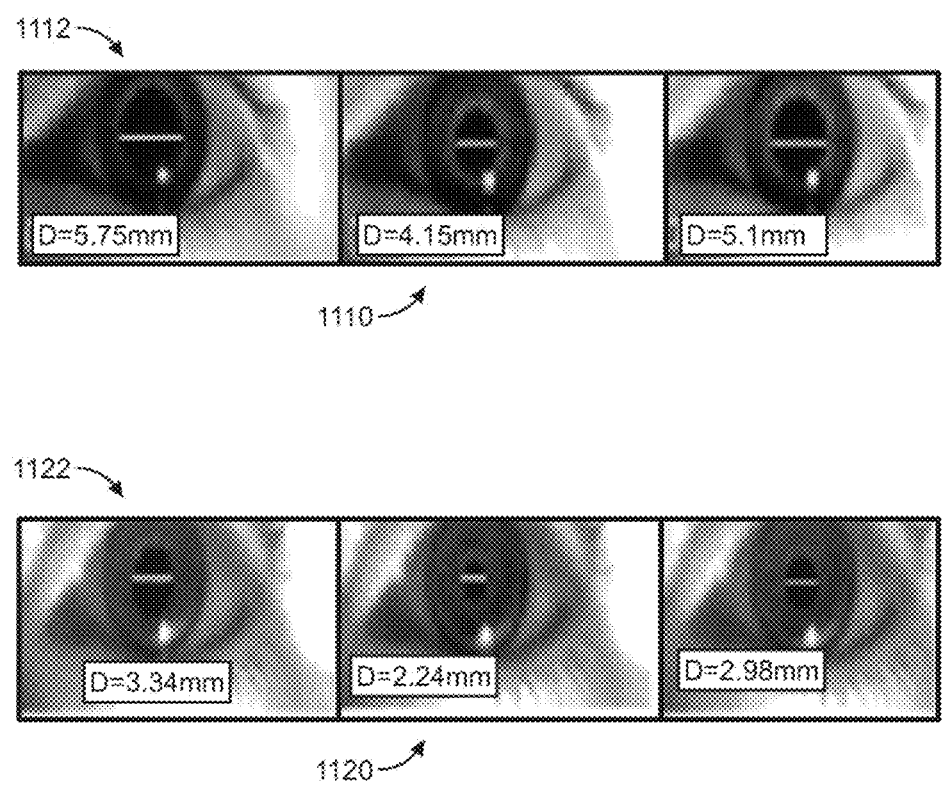
FIG. 23 depicts example pupillary constriction, according to some implementations of the present disclosure.

Referring now to FIG. 23, which depicts some example pupil diameter measurements, according to some implementations of the present disclosure. For example, 1112 and 1122 show a baseline pupil diameter for subjects 1110 and 1120, respectively. Subject 1110 is healthy and subject 1120 has Alzheimer's Disease. MCV and MCA can be calculated based on the methods discussed herein.

Determining Amount of Visual Stimulus

Figure 24:
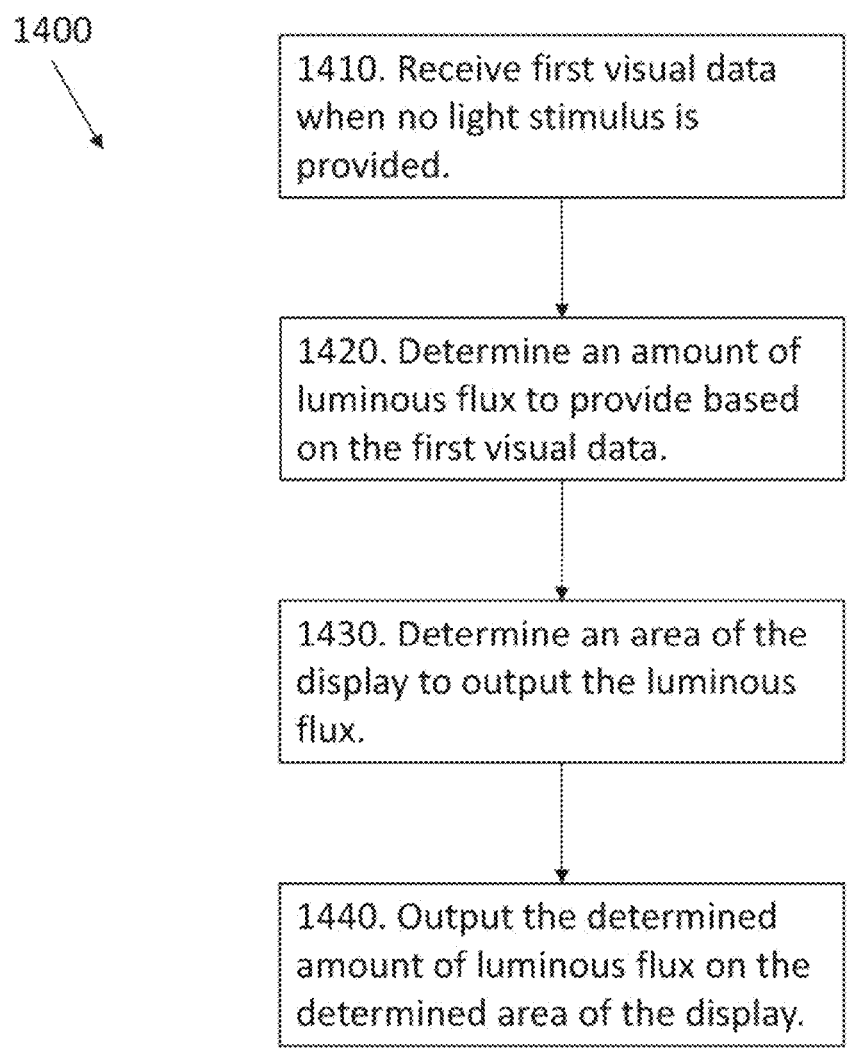
FIG. 24 depicts a method for determining luminous flux, according to some implementations of the present disclosure.

Referring now to FIG. 24, a method 1400 for determining luminous flux is disclosed, according to some implementations of the present disclosure. Methodology 1400 of FIG. 24 provides an example method for determining an amount of visual stimulus to provide at a display. For example, methodology 1400 can be performed as part of step 610 of methodology 600 of FIG. 15. In some implementations, methodology 1400 is performed on systems 400 and 500 of FIGS. 13 and 14, respectively.

Methodology 1400 begins by receiving first image data when no light stimulus is provided, at 1410. For example, camera 414 of system 400 receives image data of a user without providing light stimulus from the display 412 or sensor 416. Methodology 1400 then provides for determining an amount of luminous flux to provide, at 1420, based on the first image data received from 1410. In some implementations, the amount of luminous flux is additionally based on historical user health data, and/or based on a desired type of pupillary response. In some implementations, the amount of luminuous flux is determined to stimulate a maximum pupillary constriction of the user's pupil.

In some implementations of step 1420, the type of light output from the display is also determined. For example, a wavelength of light (or color of light within the visible light spectrum) to be displayed is determined. Each eye of a user has melanoptic receptors that are activated by different colors. Therefore, step 1420 provides for controlling the wavelength (or color) of light to activate certain melanoptic receptors in the user's eye and certain receptor pathways. In some implementations, these pathways allow delineation of diseases mediated by particular receptor pathways.

Methodology 1400 then provides for determining an area of the display to output the luminous flux, at 1430. In some implementations, an entire display surface area is used. In other examples, only a portion of the display surface area is used. In some implementations of methodology 1400, the amount of luminous flux and the area of the display to output the luminous flux (e.g., 1420 and 1430) are determined simultaneously, or in any order.

Methodology 1400 then provides for outputting the determined amount of luminous flux on the determined area of the display, at 1440. In some implementations of methodology 1400, additional image data of the eye is received after the luminous flux is output. In some implementations, the luminous flux is adjusted based on the received image data.

Identifying Multiple Pupil Responses

Figure 25:
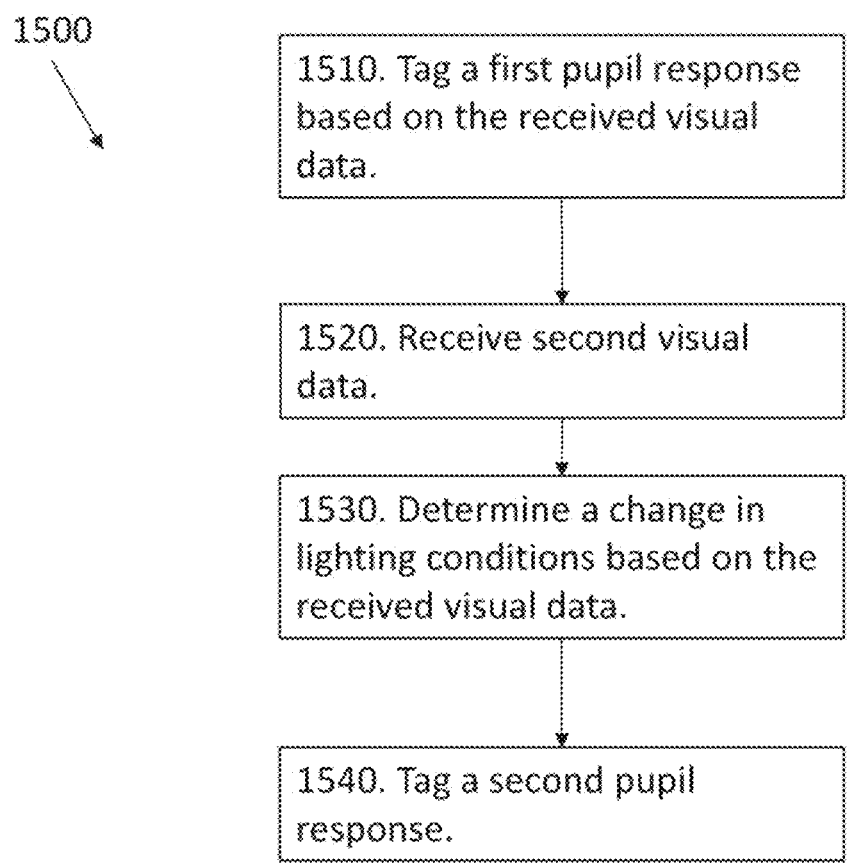
FIG. 25 depicts a method for identifying a second pupillary response, according to some implementations of the present disclosure.

In some implementations of the present disclosure, a method is provided to identify multiple pupillary responses. For example, such a method identifies whether an image data set is adulterated by unintentional pupil stimulation (e.g., during methodology 600 of FIG. 15). FIG. 25 depicts an example methodology 1500 for identifying and tagging unintentional pupil responses, according to some implementations of the present disclosure. For example, methodology 1500 can be performed before, during, and/or after methodology 600 of FIG. 15.

Methodology 1500 of FIG. 25 provides for first, at step 1510, tagging a first pupil response based on the received image data. For example, the first pupil response includes a change in any of the pupillary features as discussed herein. Methodology 1500 then provides for, at step 1520, receiving second image data, after the originally-received image data. Methodology 1500 then provides for, at step 1530, determining a change in lighting conditions. For example, the change in light conditions can be determined based on a brightness difference between the received image data from step 1510 and the received second image data from 1520.

Methodology 1500 then provides for tagging a second pupil response in the second image data, at step 1540. For example, if the second image data is a series of images, step 1540 provides for identifying the image or images which occur simultaneously, or close in time afterwards to the change in lighting conditions. In some implementations, the second pupil response is identified as any one of the pupillary features discussed herein.

Infrared Measurements Implementation

Figure 26:
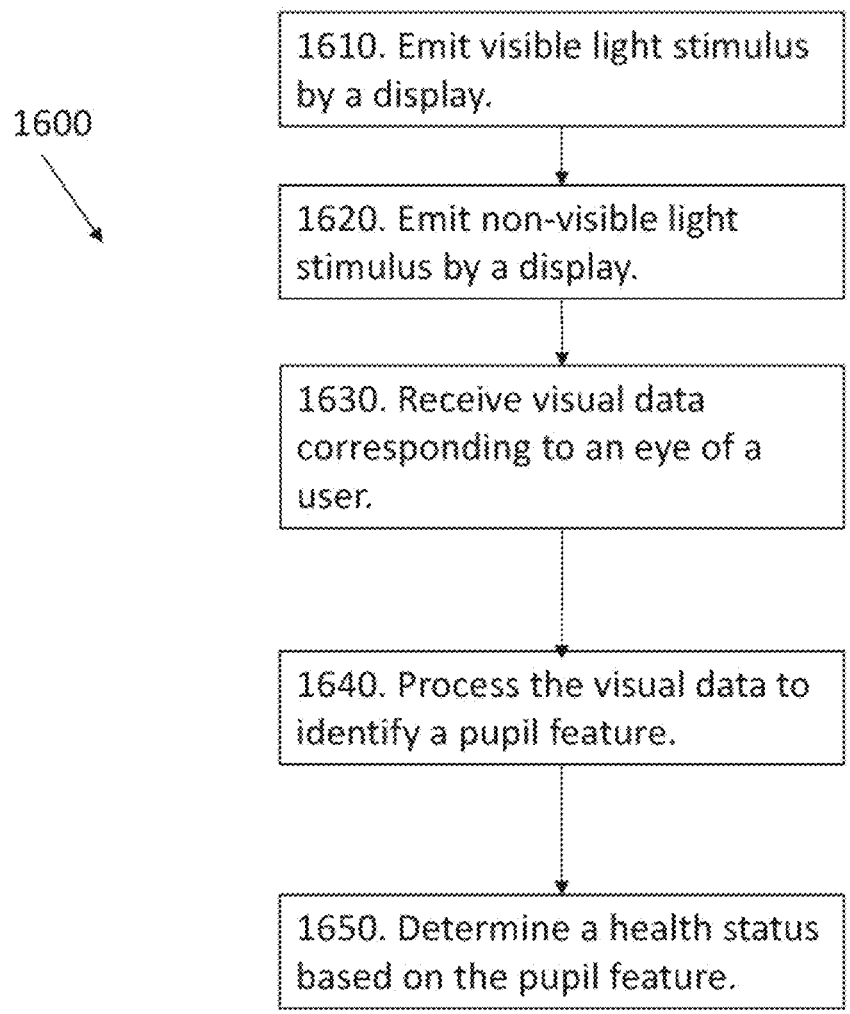
FIG. 26 depicts a method for measuring pupillary response with non-visible light, according to some implementations of the present disclosure.

The present disclosure further provides for image capture with non-visible light stimulus and/or an infrared camera. For example, the sensor 416, infrared emitter, and/or the display 412 of FIG. 13 can provide a non-visible light emission. In some implementations, the camera 414 is an infrared camera and includes one or more infrared light emitters. FIG. 26 depicts an example methodology 1600, which can be performed on systems 400 and/or 500 of FIGS. 13 and 14, respectively.

Methodology 1600 provides for, at step 1610, emitting a visible light stimulus by a display (e.g., the display 412 or the sensor 416 of FIG. 13). For example, the visible light stimulus has a wavelength greater than 1,000 nm. The visible light stimulus is directed towards the face of a user. This visible stimulus is configured to initiate a pupil response in an eye of the user.

Methodology 1600 then provides for, at 1620, emitting a non-visible light stimulus by a display (e.g., the display 412 or the sensor 416 of FIG. 13, e.g. an infrared emitter). The non-visible light stimulus is configured to illuminate the user's face sufficient to cause a high enough image contrast (sufficiently high enough for pupil-iris segmentation). Step 1620, therefore, makes use of the high-image contrast that is provided by infrared light generally. For example, the non-visible light stimulus provided at 1620 is a light stimulus with a wavelength between 600 nm and 1,000 nm.

Because step 1620 provides the illumination sufficient to provide high enough image contrast, methodology 1600 requires less visible stimulus at step 1610 than methodologies which rely only on visible stimulus (including, for example, methodology 600 of FIG. 15). Therefore, methodology 1600 is able to more accurately trigger pupil responses, because the visible stimulus provided at step 1610 does not need to illuminate the user's face.

Methodology 1600 further provides for receiving, at step 1630, image data corresponding to an eye of a user. In some implementations, the image data received is a set of images or a video. In some implementations, the set of images are collected at regular intervals (e.g., intervals measured in seconds, milliseconds, and/or microseconds) for a period of time (e.g., over one minute, two minutes, three minutes). In some implementations, the image data received at 1630 is received from an infrared camera.

Methodology 1600 further provides, at step 1640, for processing the image data to identify a pupillary feature. For example, the received image data is processed according to any of the methodologies discussed with respect to 630 of methodology 600 of FIG. 15. Methodology 1600 then provides for, at 1650, determining a health status based on the identified pupillary feature. For example, the health status is determined according to any of the methodologies discussed with respect to 640 of methodology 600 of FIG. 15.

Therefore, methodology 1600 avoids confounding pupillary response results with additional, unintentional stimulus.

Identifying Appropriate Lighting Conditions

Figure 27:
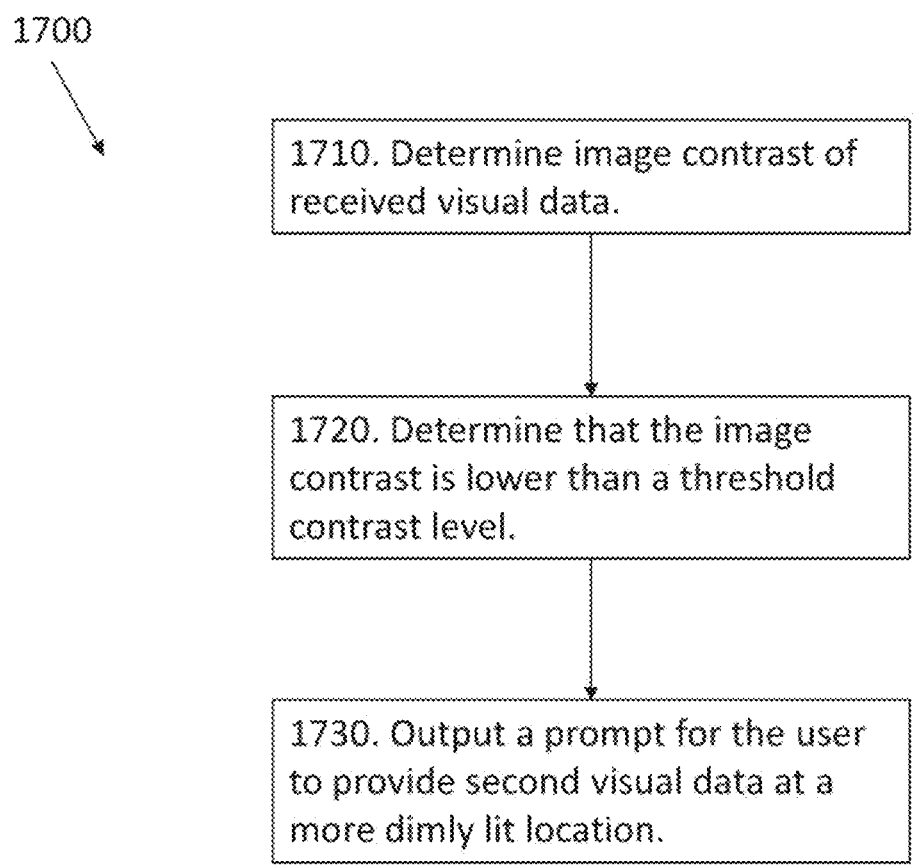
FIG. 27 depicts a method for determining proper image contrast, according to some implementations of the present disclosure.

Some implementations of the present disclosure provide for automatically detecting whether lighting conditions are sufficient to provide image data of adequate quality to determine the various pupillary features discussed herein. According to some implementations of the present disclosure, FIG. 27 depicts an example methodology 1700 for evaluating lighting conditions, according to some implementations of the present disclosure. Methodology 1700 can be performed by systems 400 and/or 500 of FIGS. 13 and 14, respectively. In some implementations, methodology 1700 is performed before, after, and/or during methodology 600 and/or methodology 1600 of FIGS. 15 and 26, respectively.

Methodology 1700 provides for, at step 1710, determining an image contrast of received image data. For example, the image contrast is determined with respect to brightness, color, saturation, and/or any other visual picture analysis means, as known in the art. Methodology 1700 then provides for, at step 1720, determining whether the image contrast is lower than a threshold contrast level. For example, step 1720 provides for determining whether pupil-iris segmentation can be performed based on the image data provided. In some implementations, step 1720 provides for determining whether pupil-iris segmentation can be performed with a certain accuracy threshold and/or confidence measure.

Methodology 1700 then provides for, at step 1730, outputting a prompt for the user to provide second image data at a more dimly-lit location. When used in conjunction with methodology 1600, methodology 1700 provides for ensuring that the user is in a dimly lit enough location to provide high contrast for pupil segmentation.

Figure 28:
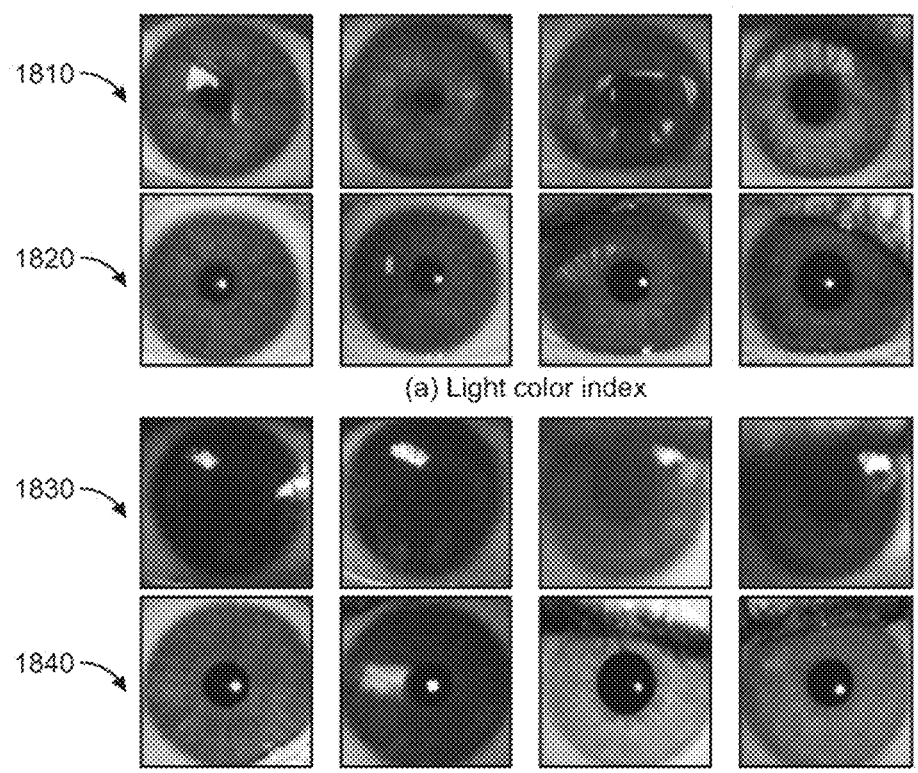
FIG. 28 depicts compares example data for pupil-iris segmentation between visible light and non-visible light, according to some implementations of the present disclosure.

According to some implementations of the present disclosure, FIG. 28 depicts example image data as compared between sets of images taken in visible light (image sets 1810 and 1830) and sets of images taken in infrared light (image sets 1820 and 1840). Image sets 1820 and 1840 show much clearer delineation between the pupil and the iris of the subject than the image sets 1810 and 1830, which are taken in visible light. In particular, image set 1830 is taken of a dark iris, and pupil segmentation is almost impossible due to the similarity of the colors of the pupil and the iris, and a low contrast between the two. Therefore, FIG. 28 demonstrates the utility of methodology 1600 of FIG. 26, which collects image data with non-visible stimulus, and methodology 1700 of FIG. 27, which ensures that the pupil-iris image contrast is sufficiently high.

Eyelid Mediated Response Implementation

Figure 31:
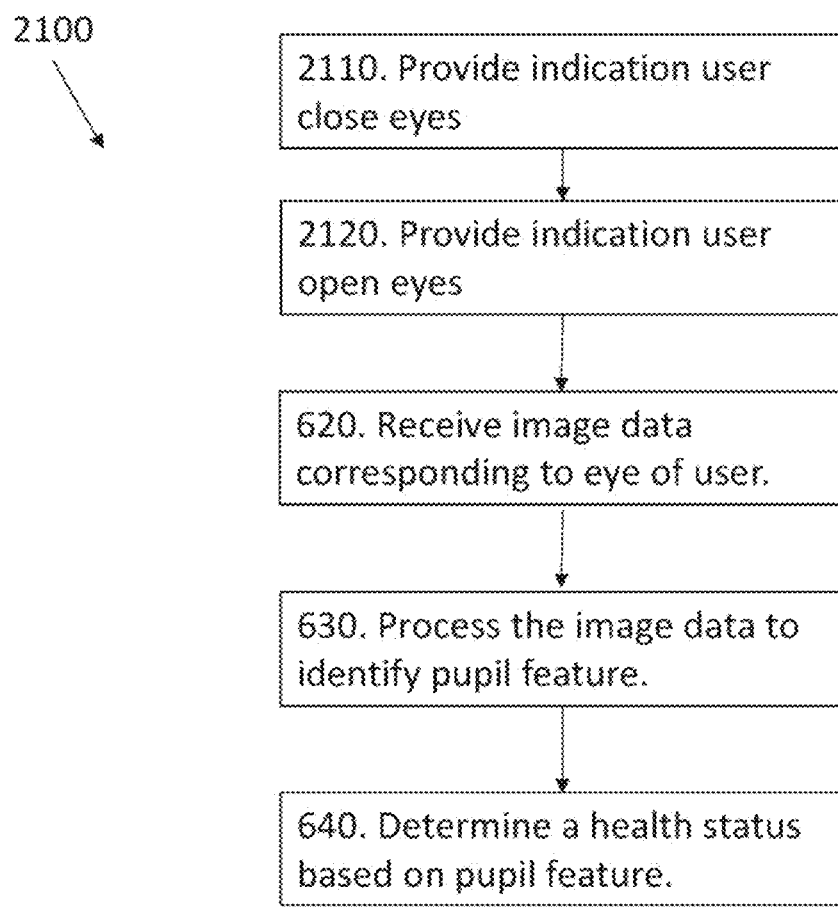
FIG. 31 shows an exemplary methodology for measuring pupillary response with an eyelid mediated stimulus, according to some implementations of the present disclosure.

FIG. 31 is a flow chart providing a detailed example of how to implement the disclosed systems and methods while utilizing the user's eyelids to dark-adapt the pupil and mediate the stimulus using ambient light (herein "eyelid mediated response"). Accordingly, when a user closes their eyelids the pupils will undergo the process of dark-adaptation in which the pupils become accustomed to darkness—effectively dilating the pupil. This will serve as a baseline before the light stimulus is applied (e.g., the user open's their eyes)—facilitating latency measurements and maximal construction.

For instance, in this example, the system may display instructions for the user to close their eyes for a predetermined amount of time, or until they hear a tone or feel a vibration. This is quite advantageous, because the contrast between the light entering the user's eyes when there are closed and when there are open (and thus allowing all of the ambient light of the room to enter the user's eyes) will likely be enough to trigger the pupillary reflex.

For instance, the typically maximum lux emitted from a display at a common viewing distance (e.g. 200 lux) may not be enough to trigger a sufficient pupillary light reflex. (e.g. 300 lux or greater may be required) However, the contrast between the light entering the eyes in their open and closed states during normal lighting conditions will be sufficient to trigger a pupillary light reflex. Otherwise, it is difficult to ensure sufficient contrast between ambient light and light stimulus to generate a pupillary light reflex as the ambient light may be too bright. Accordingly, the eyelid mediated implementation may circumvent the need for an additional light stimulus (e.g. a flash of light or brightened display). In other examples, the eyelid mediated stimulus may allow the display to provide enough additional stimulus to trigger the response when the baseline dilation starts from when a user has their eyes closed for a sufficient amount of time.

Thus, using this system, in some examples, there is no need for a light based stimulus to be provided by the device. Accordingly, the user may hold the phone with the display facing them (because the flash is not needed). Additionally, the display is not needed to provide a light stimulus to the user's eyes and in some examples a back facing camera may be utilized to assess the eyelid mediated pupillary response. Furthermore, utilizing an eyelid mediated response may be more desirable than flashing light in the user's eyes that is bright enough to trigger the pupillary reflex because it may be more comfortable for the user. In other examples, closing the user's eyes combined with a light stimulus from a display may be enough to trigger a pupillary light reflex.

Also, this method allows the user to easily implement the method in any sufficiently lit or bright room that has enough ambient light to trigger the reflex after the user opens their eyes from a closed and dark-adapted state. FIG. 31 provides an example of implementing this method. In some example, the system may first provide a live feed of image data on the display 412 so the user can line up their eyes properly in front of the camera 414 as described herein (for instance with circles or arrows displayed on the live image data for the user to line up their eyes inside). In other examples, the back facing camera may be utilized and the feedback to the user may be purely audio or vibrational to inform them when to open and close their eyes, and when their eyes are properly aligned with the back facing camera.

Next, the system may provide an indication that the user should close their eyes 2110. This may include a text based message displayed on the display 412. For instance, the display 412 may display the text "close your eyes for [3, 10, 15] seconds" or "close your eyes until you hear a tone [or feel a vibration]." The system may then start a timer for three seconds (or 4 seconds, 10 seconds, 15 seconds, or other suitable times sufficient to trigger a pupillary light reflex) and begin to record image data output from the camera 414 after the set time has elapsed. In other examples, the system will sound a tone or energize a vibration motor after the set time has elapsed notifying the user they can open their eyes

2120. In those examples, the system will start recording image data once the tone or vibration is initiated or just before.

In some examples, the system may process the image data until it determines that at least one of the user's eyes is open (e.g. computer vision to identify a pupil, iris, or other feature of the eyeball) and detected or filter frames where it determines the user's eye is closed. This may be important, because this will allow the system to identify the first frames where the user's eyes are open (by initiating recording of the camera 414 while the user's eyes are still closed) and therefore capture all or the majority of the pupillary light reflex.

In some examples, this may include determining pupil diameter based on a partial image of the pupil before the user's eyes are fully open or if the user's eyes do not open fully. For instance, the system may extrapolate or otherwise estimate the full diameter of the pupil from a partial diameter. For instance, if the circle angle of the visible pupil is below 360 degrees, known mathematical functions (e.g. trigonometry) can be utilized to estimate the full the pupil diameter. This may include determining the pupil diameter from a small portion of the pupil being visible (e.g. 90 degrees of visible circle angle). In some examples, the accuracy of the partial measurement's estimation of pupil diameter may be high enough to utilize in the calculation of the health status, including for instance a quantitative measure of the pupillary light reflex.

Additionally, the system may also identify the frames where the user's eyes are properly focused at the camera or a certain point on the screen and thus an accurate measurement of the pupil diameter can be performed. The system may include indications on the display of where the user should focus their gaze (e.g. arrows). In other examples, the system, may be able to determine the direction of the user's gaze and approximate the pupil diameter based on those measurements.

Additionally, the system may continue to monitor the frames to determine that sufficient frames where captured with the user's eye sufficiently open for a sufficient period of time (e.g. user closes their eyes too soon). If there are not a sufficient number of useable frames captured to determine a pupillary light reflex or other relevant pupil features, the process would start over. Next, the system may receive visual data corresponding to an eye of a user (step 520) and the system may process the image data in the same manner as described herein with respect to FIG. 15. This includes processing the image data to identify a pupil feature (step 630) and processing the pupil feature to determine a health status of the user (step 640).

Instructions to the User

Figure 12:
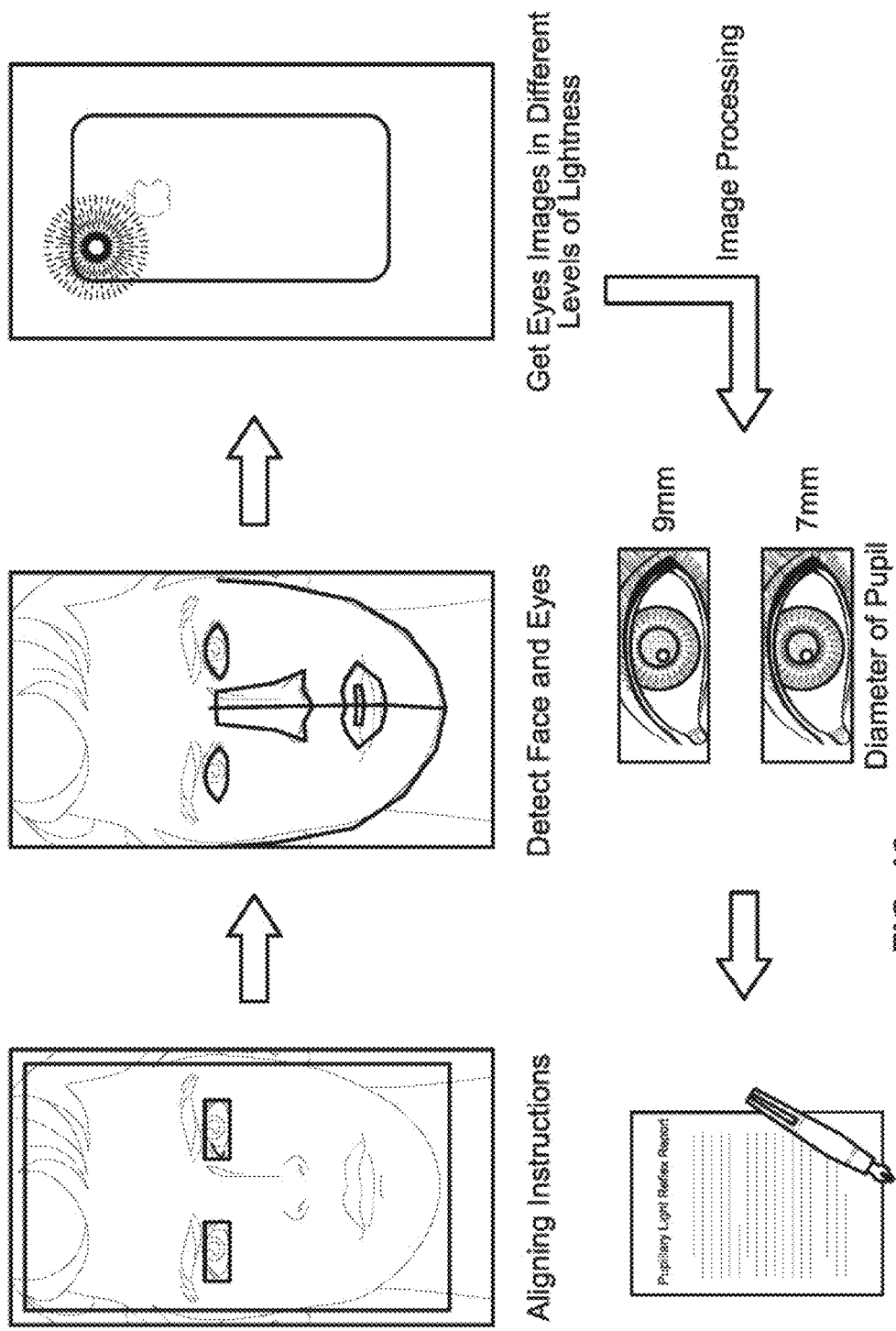
FIG. 12 is a diagram depicting a method for determining PLR, according to some implementations of the present disclosure.

To measure PLR, the user is given instructions for aligning their eyes in the camera. This provides the proper image size for further image processing and pupil measurement. The camera session is started to detect the user's face and obtain images of the user's eyes. The background color and phone brightness (if using front-facing camera) are adjusted (or torchLevel adjusted) to create various levels of lightness/darkness. The images may be processed in real-time including segmentation, obtaining the diameter of the pupil and tracking the time for measuring pupil contraction speeds. Finally, results of the measurements including reaction time for both eyes, contraction speeds, and the percentage of pupil closure may be presented to the user. An example implementation of this method is indicated in FIG. 12.

Although the foregoing implementations have been described in some detail for purposes of clarity of understanding, the present disclosure is not limited to the details provided. There are many alternative ways of implementing the present disclosure. The disclosed implementations are illustrative and not restrictive.

Additional Implementations

According to some implementations of the present disclosure, a system for evaluating pupillary features includes a device, a camera, a memory, and a control system. The camera is located on the device. The memory stores machine-readable instructions. The control system includes one or more processors configured to execute the machine-readable instructions. Image data corresponding to at least one eye of a user is received from the camera at a first time and at least one additional time. The image data is processed to determine at least one pupillary feature at the first time and the at least one additional time. Based at least in part on the at least one pupillary feature at the first time and the at least one additional time, a progression of a neurologic disease associated with the user is determined.

In some implementations, the neurologic disease includes Alzheimer's or Dementia, and the at least one pupillary feature includes MCA or MCV. In some implementations, the neurologic disease includes Parkinson's, and the at least one pupillary feature includes latency. In some implementations, the neurologic disease includes depression, anxiety, or schizophrenia.

In some implementations, the progression includes an improvement after the user has been subjected to a treatment. In some implementations, the determining the progression of the neurologic disease associated with the user includes determining a trend in the at least one pupillary feature based on the first time and at least one additional time. In some implementations, determining the progression of the neurologic disease associated with the user includes processing (i) both the at least one pupillary feature at the first time and the at least one additional time and (ii) a score on a cognitive test using a predetermined weighting of the at least one pupillary feature and the cognitive test.

In some implementations, the at least one additional time is on a different day, month, or year than the first time. In some implementations, the at least one additional time is once a month over a period of years.

According to some implementations of the present disclosure, a system for evaluating pupillary features includes a device, a camera, a memory, and a control system. The camera is located on the device. The memory stores machine-readable instructions. The control system includes one or more processors configured to execute the machine-readable instructions. Image data corresponding to at least one eye of a user is received from the camera at a first time and at least one additional time. The image data is processed to determine at least one pupillary feature at the first time and the at least one additional time. Based at least in part on the at least one pupillary feature at the first time and the at least one additional time, a progression of a disease associated with the user is determined. The disease may include cholesterol, iris deposits, neurologic diseases such as Dementia or Alzhiemer's. In some examples, the disease may include a progression of Alzheimer's based on the change in PPR over time.

According to some implementations of the present disclosure, a system for evaluating pupillary light reflex includes a device, a camera, a display, a memory, and a control system. The device includes a front and a back. The camera is located on the front of the device. The display is located on the front of the device. The memory stores machine-readable instructions. The control system includes one or more processors configured to execute the machine-readable instructions. At least three spatial markers are displayed on the display. Instructions to line two eyes and a nose of a user with the at least three spatial markers are displayed on the display. Image data corresponding to at least one of the two eyes of the user is received from the camera. The image data is processed to determine at least one pupillary feature. Based at least in part on the at least one pupillary feature, a health status associated with the user is determined.

In some implementations, the at least three spatial markers include outlines of shapes.

In some implementations, the processing the image data further includes: identifying the two eyes and the nose of the user in the image data; and modifying the image data based at least in part on a position of the two eyes and the nose of the user. In some implementations, the position is used to determine a depth and an angle the two eyes of the user from the camera. In some implementations, it is displayed on a screen for the user to change the depth or the angle, if the determined depth or the determined angle is not within a predetermined range.

In some implementations, the system further includes an ambient light sensor, wherein the one or more processors are further configured to process data output from the ambient light sensor to determine whether an amount of ambient light is sufficient.

According to some implementations of the present disclosure, a system for evaluating pupillary features includes a mobile device, a camera, a user interface, a memory, and a control system. The mobile device includes a front and a back. The camera is located on the front of the mobile device. The user interface is located on the front of the mobile device. The memory stores machine-readable instructions. The control system includes one or more processors configured to execute the machine-readable instructions. The user interface is caused to emit at least one visible light stimulus or a mental stimulus. Image data corresponding to at least one eye of a user captured during and after the emitting the at least one visible light stimulus or one mental stimulus is received from the camera. The image data is processed to identify at least one pupillary feature. Based at least in part on the at least one pupillary feature, a health status associated with the user is determined. In some implementations, the user interface includes a touchscreen. In this example, this advantageously allows the front facing screen act as the stimulus, while the front facing camera allows the user to self-capture their pupillary features using a smart device, which ultimately enables easier capturing of repeated measurements of the user to accumulate longitudinal data that can determine a trend and/or deviation from baseline.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present disclosure, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Conclusion

One or more elements or aspects or steps, or any portion(s) thereof, from one or more of any of the claims below can be combined with one or more elements or aspects or steps, or any portion(s) thereof, from one or more of any of the other claims or combinations thereof, to form one or more additional implementations and/or claims of the present disclosure.

While various examples of the present disclosure have been described herein, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

Although the disclosure has been illustrated and described with respect to one or more implementations, equivalent alterations and modifications will occur to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. A system for detecting developing diseases, disorders, or disease precursors, comprising:
 a first client device configured to be carried by a user, the first client device having including
  a front and a back;
  a camera located on the front of the first client device;
  a display located on the front of the first client device, the display configured to emit a light stimulus;
  a non-transitory memory storing machine-readable instructions; and a control system including one or more processors configured to execute the machine-readable instructions to:
    receive, from the camera, image data corresponding to at least one eye of a user; and
    process the image data to determine at least one pupillary feature;
a second client device configured to be home based, the second client device providing phenotypic data for the user; and
a phenotypic detection platform including a datastore and an analytics module;
the first client device, the second client device, and the phenotypic detection platform in electronic communication via a network;
the phenotypic detection platform including a second non-transitory memory storing second machine-readable instructions, and one or more phenotypic detection platform processors configured to execute the second machine-readable instructions to:
    receive the at least one pupillary feature from the first client device,
    receive the phenotypic data from the second client device,
    access medical data stored in the datastore, and
    based at least in part on the at least one pupillary feature, the phenotypic data, and the medical data, detect a digital marker indicative of a developing disease, disorder, or disease precursor for the user.

2. The system of claim 1, wherein the at least one pupillary feature includes pupil response latency, constriction latency, maximum constriction velocity, average constriction velocity, dilation velocity, constriction amplitude, constriction percentage, post illumination pupil response, a position of the center of the pupil of the user, a 75% recovery time, a pupil escape, a baseline pupil amplitude, or any combination thereof.

3. The system of claim 1, wherein the light stimulus comprises a predetermined amount of luminous flux.

4. The system of claim 1, wherein the light stimulus includes a mental stimulus to the user, the mental stimulus including a memory test, math problems, images that evoke a mental response, other mental stimuli, or combinations thereof.

5. The system of claim 1, wherein a first field of view of the camera is similar to a second field of view of the distance detector.

6. The system of claim 1, wherein the one or more processors are further configured to adjust a brightness and a contrast of the at least one eye of the user relative to a background including a region around the at least one eye of the user.

7. The system of claim 1, wherein the one or more processors are further configured to adjust a brightness and a contrast of the at least one eye of the user and a face of the user relative to a background including a region around the face of the user.

8. The system of claim 1, wherein the one or more processors are further configured to remove frames where the at least one eye of the user is blinking.

9. The system of claim 1, wherein the one or more processors are further configured to reduce artifact due to movements of the user.

10. The system of claim 1, wherein the health status is inferred from the at least one characteristic of a pupillary light reflex.

11. The system of claim 1, wherein the health status includes a level of impairment.

12. The system of claim 11, wherein the level of impairment includes a level of alcohol impairment.

13. The system of claim 1, wherein the health status includes a detection or progression of neurologic disease.

14. The system of claim 1, wherein the health status includes acute changes in autonomic nervous system function.

15. A system for detecting developing diseases, disorders, or disease precursors, comprising:
    a first client device configured to be carried or worn by a user, the first client device including first sensors for generating active phenotypic data and second sensors for generating passive phenotypic data for the user;
    a second client device configured to be home or automobile based, the second client device providing additional phenotypic data for the user; and
    a phenotypic detection platform including a datastore and an analytics module;
    the first client device, the second client device, and the phenotypic detection platform in electronic communication via a network;
    the phenotypic detection platform including a non-transitory memory storing machine-readable instructions, and one or more processors configured to execute the machine-readable instructions to:
        receive the at least one of the active phenotypic data and the passive phenotypic data from the first client device,
        receive the additional phenotypic data from the second client device,
        access medical data stored in the datastore, and
        based at least in part on the at least one of the active phenotypic data and the passive phenotypic data from the first client device, the additional phenotypic data from the second client device, and the medical data accessed from the datastore, detect a digital marker indicative of a developing disease, disorder, or disease precursor for the user.

16. The system of claim 15, wherein the active phenotypic data generated by the first sensors include a video capture of the user's eye, heart rate of the user when performing a specified task, position of the user's hands when performing the specified task, or any combination thereof.

17. The system of claim 15, wherein the passive phenotypic data generated by the second sensors of the first client include accelerometer data of the user walking, GPS data of where or how far the user has walked, heart rate data of the user as part of the user's daily routine, or any combination thereof.

18. A system for detecting developing diseases, disorders, or disease precursors, comprising:
    a first client device configured to be carried or worn by a user, the first client device including first sensors for generating active phenotypic data and second sensors for generating passive phenotypic data for the user;
    a second client device configured to be home or automobile based, the second client device providing additional phenotypic data for the user;
    a phenotypic detection platform including a datastore that stores medical data and further including an analytics module; and
    a healthcare provider system providing access to additional medical data in addition to the medical data stored in the datastore;

the first client device, the second client device, the phenotypic detection platform, and the healthcare provider system in electronic communication via a network;

the phenotypic detection platform including a non-transitory memory storing machine-readable instructions, and one or more processors configured to execute the machine-readable instructions to:

receive the at least one of the active phenotypic data and the passive phenotypic data from the first client device, receive the additional phenotypic data from the second client device, access the medical data stored in the datastore, access the additional medical data provided by the healthcare provider system;

based at least in part on the at least one of the active phenotypic data and the passive phenotypic data from the first client device, the additional phenotypic data from the second client device, the medical data accessed from the datastore, and the additional medical data accessed from the healthcare provider system, detect a digital marker indicative of a developing disease, disorder, or disease precursor for the user; and transmit the detection of the digital marker indicative of the developing disease, disorder, or disease precursor for the user to the healthcare provider system.

19. The system of claim 18, wherein the additional phenotypic data for the user include the user's home temperature, a log of changes to the user's home temperature, the time the user spends at home, the amount of sleep the user gets, the user's in-home movement patterns, or any combination thereof.

20. The system of claim 18, wherein the additional phenotypic data for the user include the user's automobile temperature, a log of changes to the user's automobile temperature, GPS data indicative of routes that the user takes, times at which the user is driving, or any combination thereof.

* * * * *